(12) United States Patent
Smith

(10) Patent No.: US 11,844,707 B2
(45) Date of Patent: Dec. 19, 2023

(54) ADJUSTABLE STIFFNESS PROSTHETIC FOOT

(71) Applicant: Otto Bock HealthCare LP, Austin, TX (US)

(72) Inventor: Justin R. Smith, West Jordan, UT (US)

(73) Assignee: OTTO BOCK HEALTHCARE LP, Minneapolis, MN (US)

( * ) Notice: Subject to any disclaimer, the term of this patent is extended or adjusted under 35 U.S.C. 154(b) by 202 days.

(21) Appl. No.: 16/137,881

(22) Filed: Sep. 21, 2018

(65) Prior Publication Data
US 2019/0015224 A1  Jan. 17, 2019

Related U.S. Application Data

(63) Continuation of application No. 14/686,460, filed on Apr. 14, 2015, now Pat. No. 10,098,762.
(Continued)

(51) Int. Cl.
*A61F 2/66* (2006.01)
*A61F 2/76* (2006.01)
(Continued)

(52) U.S. Cl.
CPC .......... *A61F 2/66* (2013.01); *A61F 2002/502* (2013.01); *A61F 2002/503* (2013.01);
(Continued)

(58) Field of Classification Search
CPC ..................................... A61F 2002/6657–6692
See application file for complete search history.

(56) References Cited

U.S. PATENT DOCUMENTS 5,030,239 A  7/1991  Copes
5,112,356 A *  5/1992  Harris .................. A61F 2/66
                                                    623/49
(Continued)

FOREIGN PATENT DOCUMENTS

EP   0884033 B1   9/2002
FR   2626463 A1   8/1989
(Continued)

OTHER PUBLICATIONS

"International Search Report and Written Opinion of the International Searching Authority," issued in connection with Int'l Appl. No. PCT/US2015/025724, dated Jun. 26, 2015 (9 pages).
(Continued)

*Primary Examiner* — David H Willse
(74) *Attorney, Agent, or Firm* — HOLLAND & HART LLP

(57) ABSTRACT

A foot prosthesis that includes at least one spring element, an attachment member, and a heel member. The at least one spring element has a toe end portion, a heel end portion, an upper surface, and a lower surface. The attachment member is mounted to the upper surface and is configured to connect the foot prosthesis to a lower limb prosthesis component. A position of the attachment member is adjustable along a length of the at least one spring element. The heel member is mounted below the lower surface of the at least one spring element, and a position of the heel member is adjustable along the length of the at least one spring element.

18 Claims, 45 Drawing Sheets

Related U.S. Application Data

(60) Provisional application No. 61/979,485, filed on Apr. 14, 2014.

(51) Int. Cl.
 *A61F 2/50* (2006.01)
 *A61F 2/60* (2006.01)

(52) U.S. Cl.
 CPC . *A61F 2002/509* (2013.01); *A61F 2002/5009* (2013.01); *A61F 2002/5021* (2013.01); *A61F 2002/5079* (2013.01); *A61F 2002/5083* (2013.01); *A61F 2002/607* (2013.01); *A61F 2002/665* (2013.01); *A61F 2002/6614* (2013.01); *A61F 2002/6642* (2013.01); *A61F 2002/6657* (2013.01); *A61F 2002/6664* (2013.01)

(56) References Cited

U.S. PATENT DOCUMENTS

| | | | |
|---|---|---|---|
| 5,290,319 A | | 3/1994 | Phillips |
| 5,376,141 A | * | 12/1994 | Phillips ............... A61F 2/66 623/38 |
| 5,944,760 A | | 8/1999 | Christensen |
| 6,099,572 A | * | 8/2000 | Mosler ............... A61F 2/66 623/53 |
| 6,767,370 B1 | | 7/2004 | Mosler |
| 7,060,104 B2 | | 6/2006 | Phillips |
| 7,520,904 B2 | | 4/2009 | Christensen |
| 7,686,848 B2 | | 3/2010 | Christensen |
| 2006/0069450 A1 | | 3/2006 | McCarvill et al. |
| 2006/0185703 A1 | | 8/2006 | Townsend et al. |
| 2009/0012630 A1 | * | 1/2009 | Mosler ............... A61F 2/66 623/55 |
| 2010/0042228 A1 | | 2/2010 | Doddroe et al. |
| 2012/0179274 A1 | | 7/2012 | Christensen |

FOREIGN PATENT DOCUMENTS

| | | | | |
|---|---|---|---|---|
| RU | 2 062 075 C1 | * | 6/1996 | ............... A61F 2/66 |
| WO | 9100070 A | | 1/1991 | |
| WO | WO 02/02034 A1 | * | 1/2002 | ............... A61F 2/66 |

OTHER PUBLICATIONS

PCT International Search Report for PCT International Application No. PCT/US2015/025734, dated Jun. 26, 2015 (4 pp.).

* cited by examiner

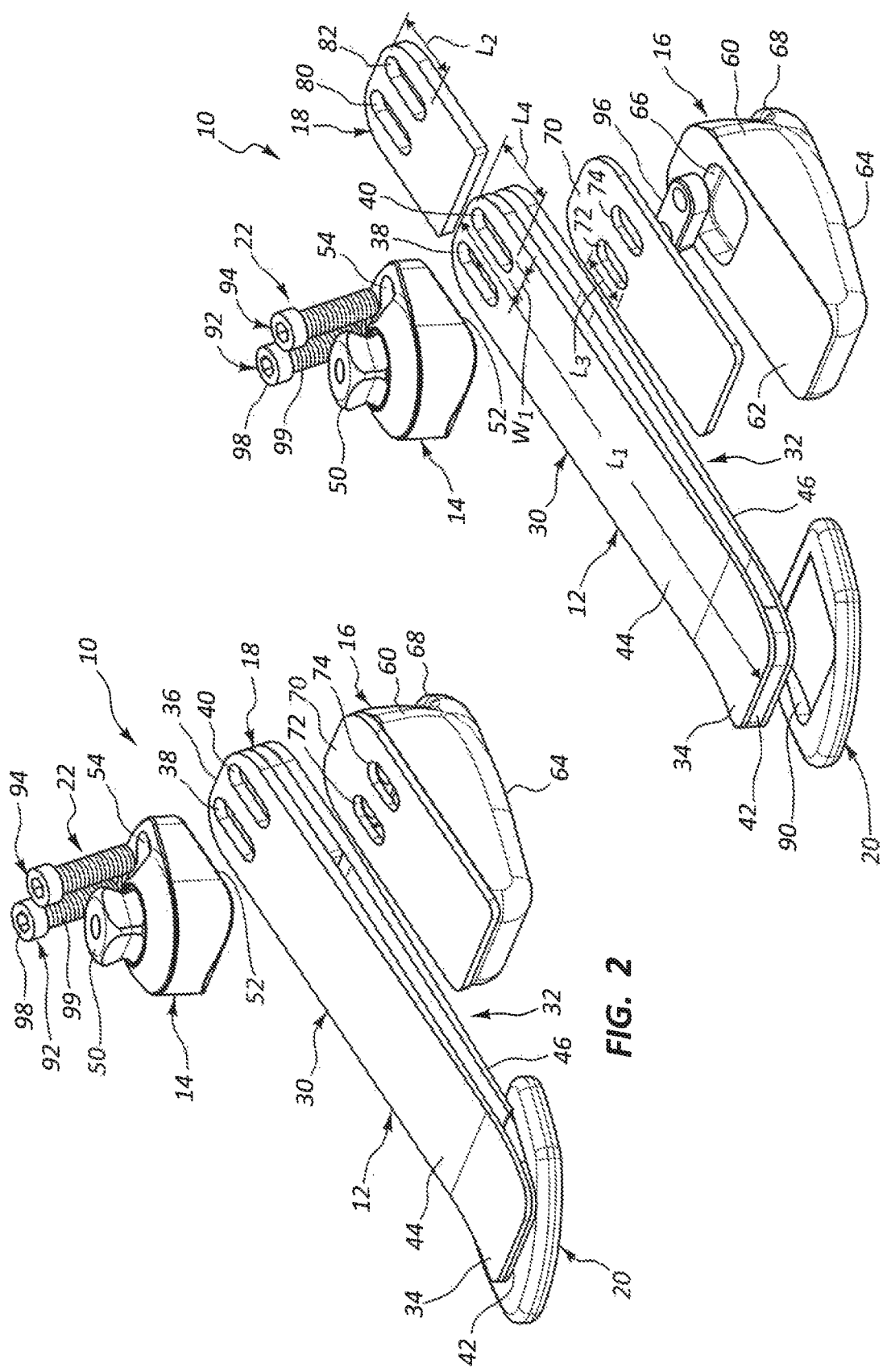

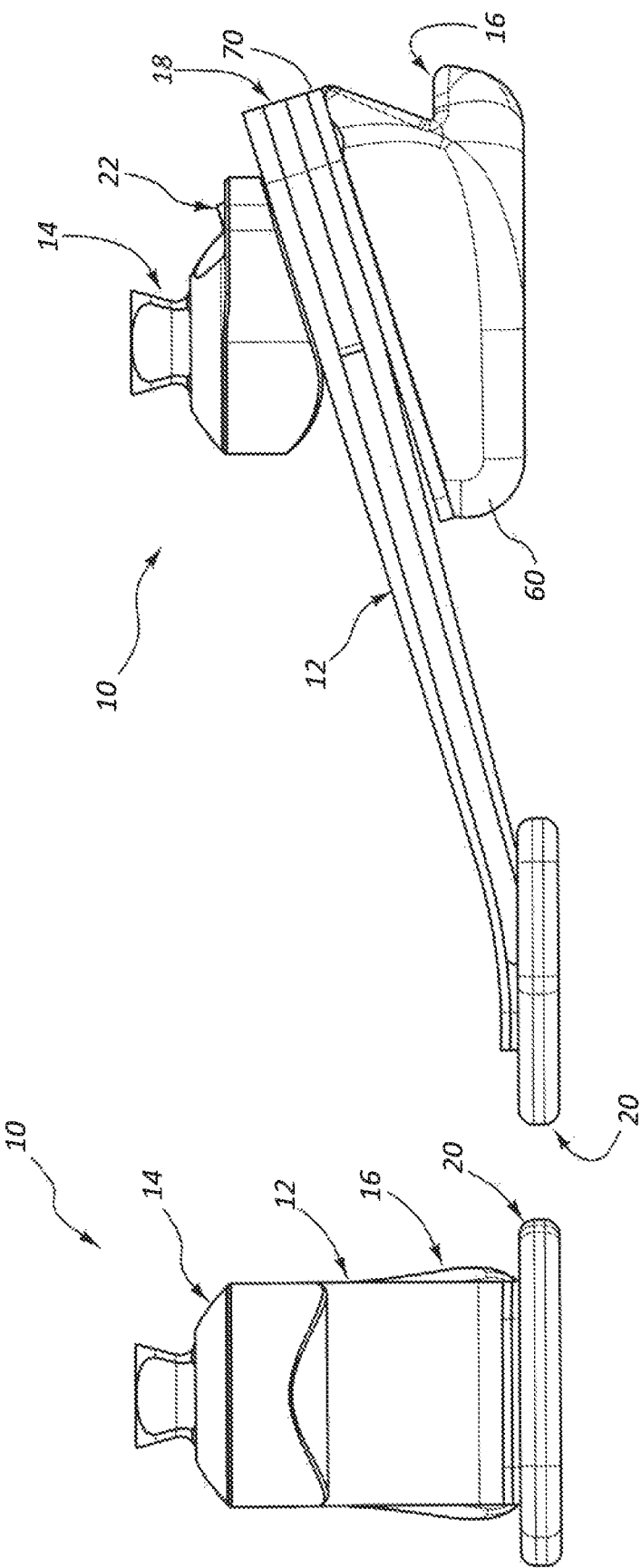

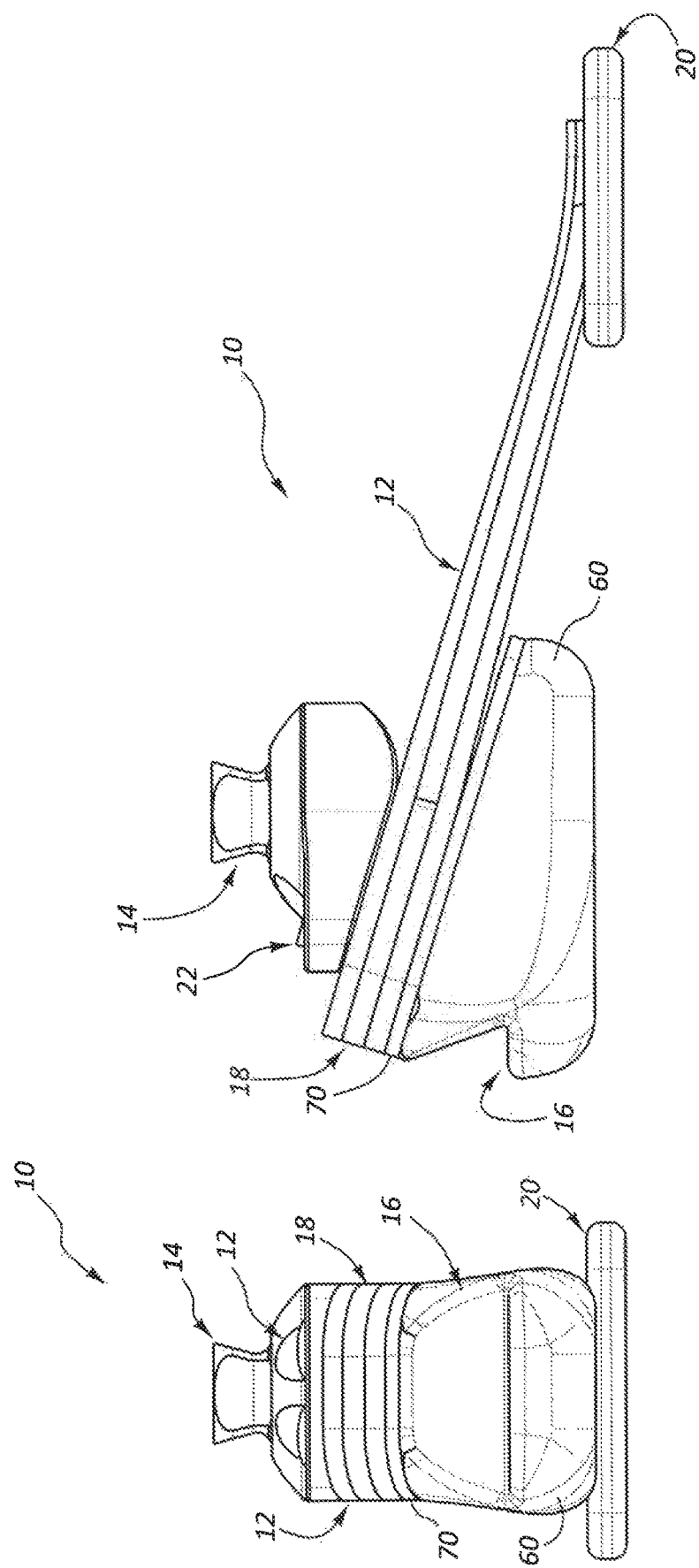

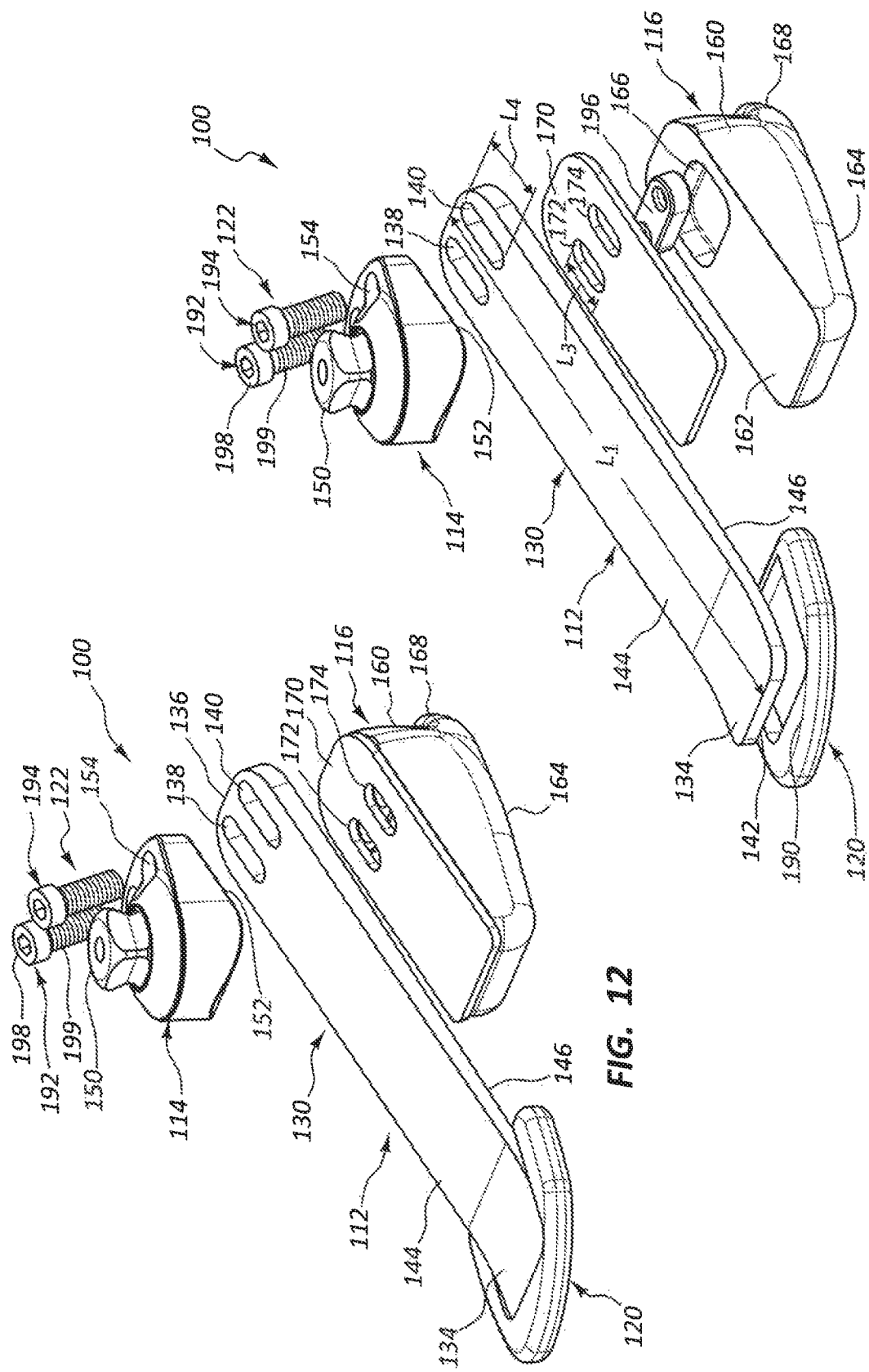

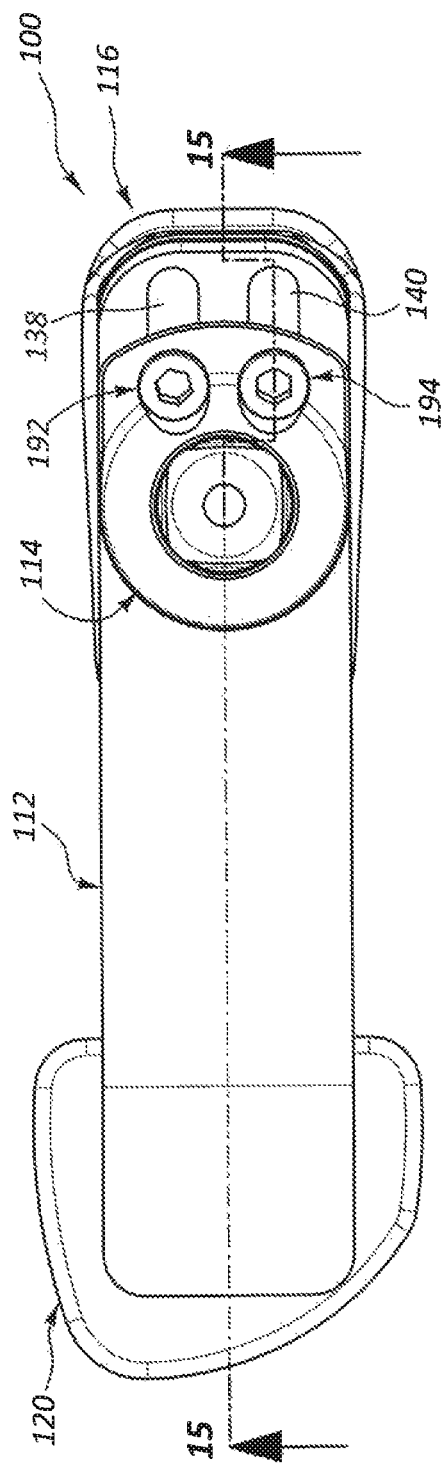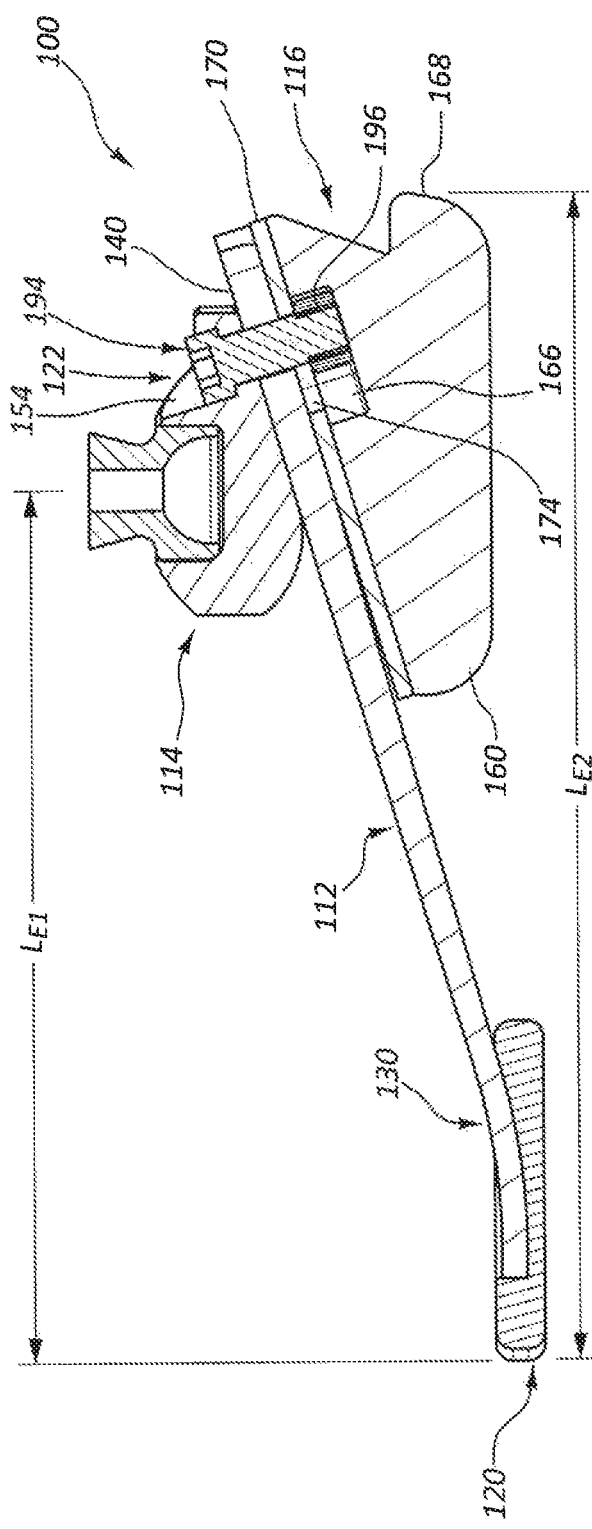

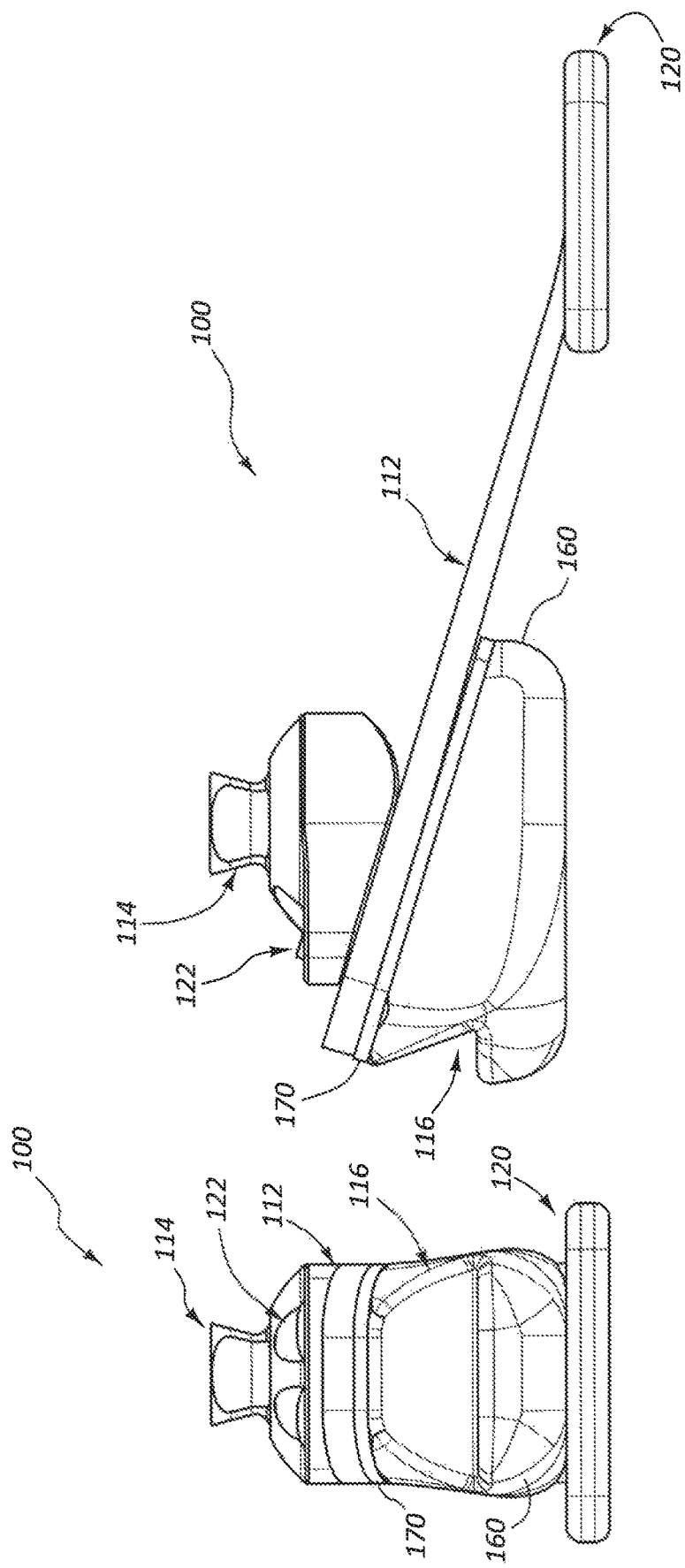

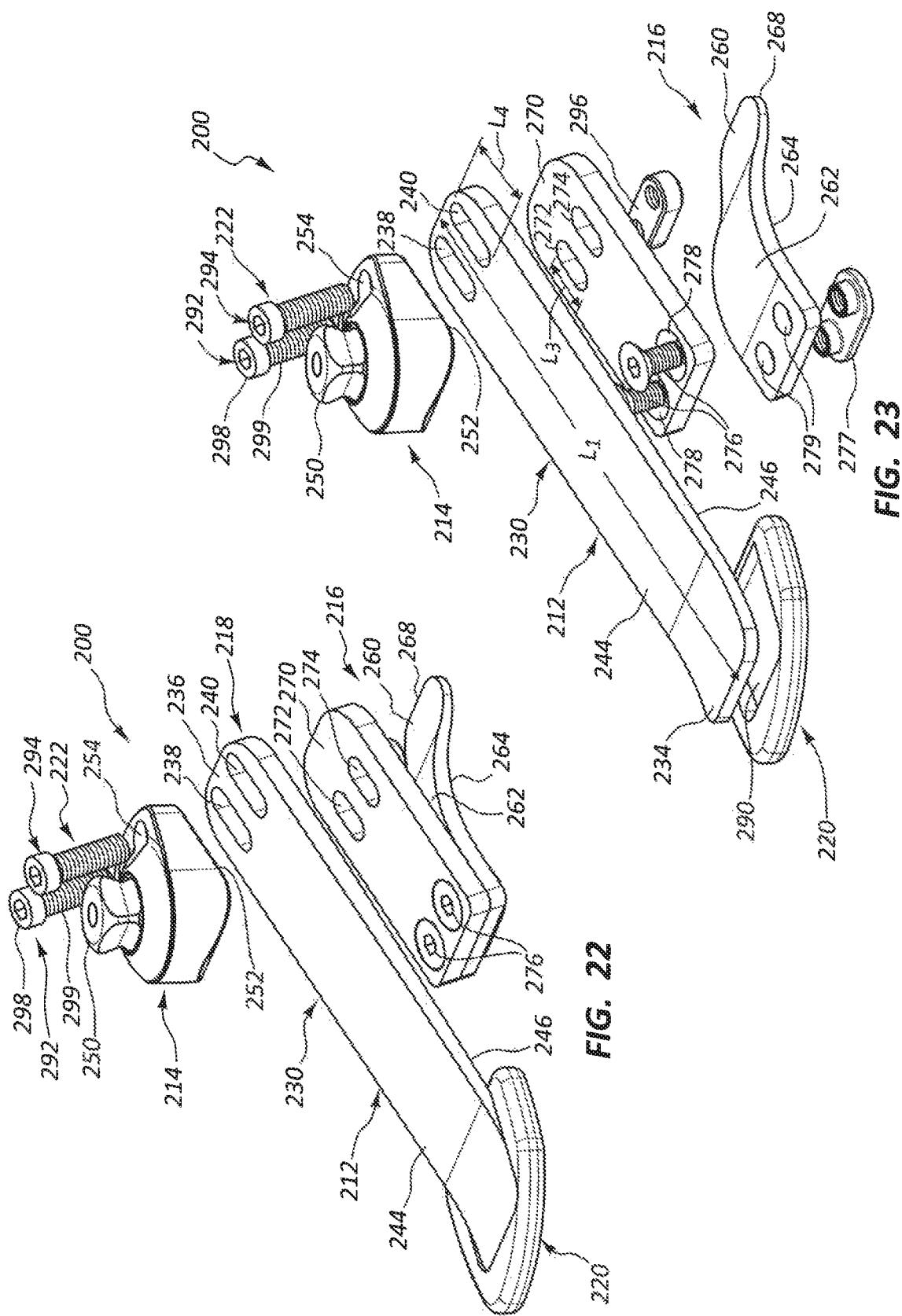

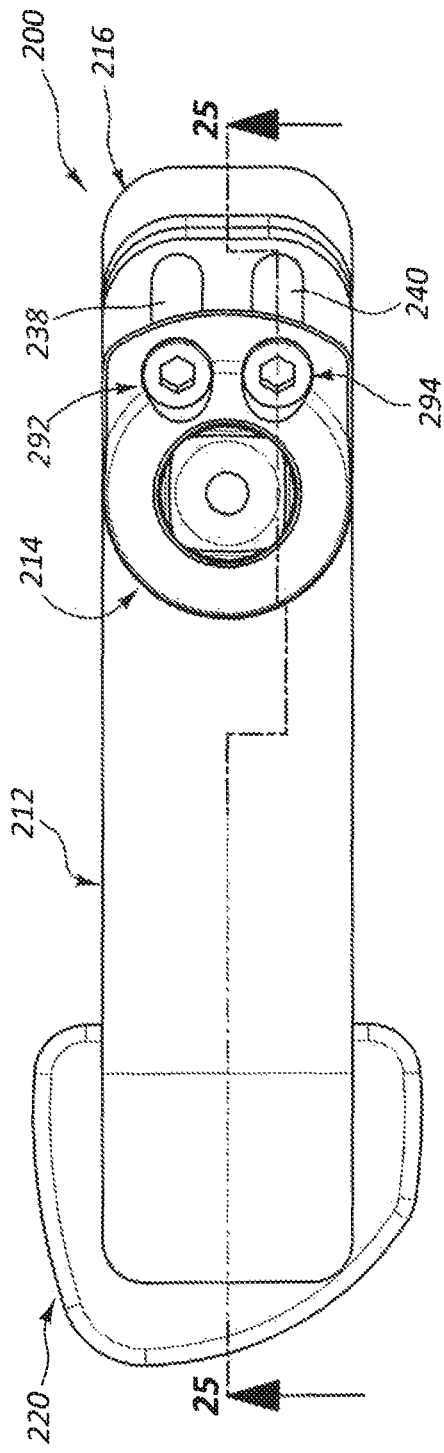
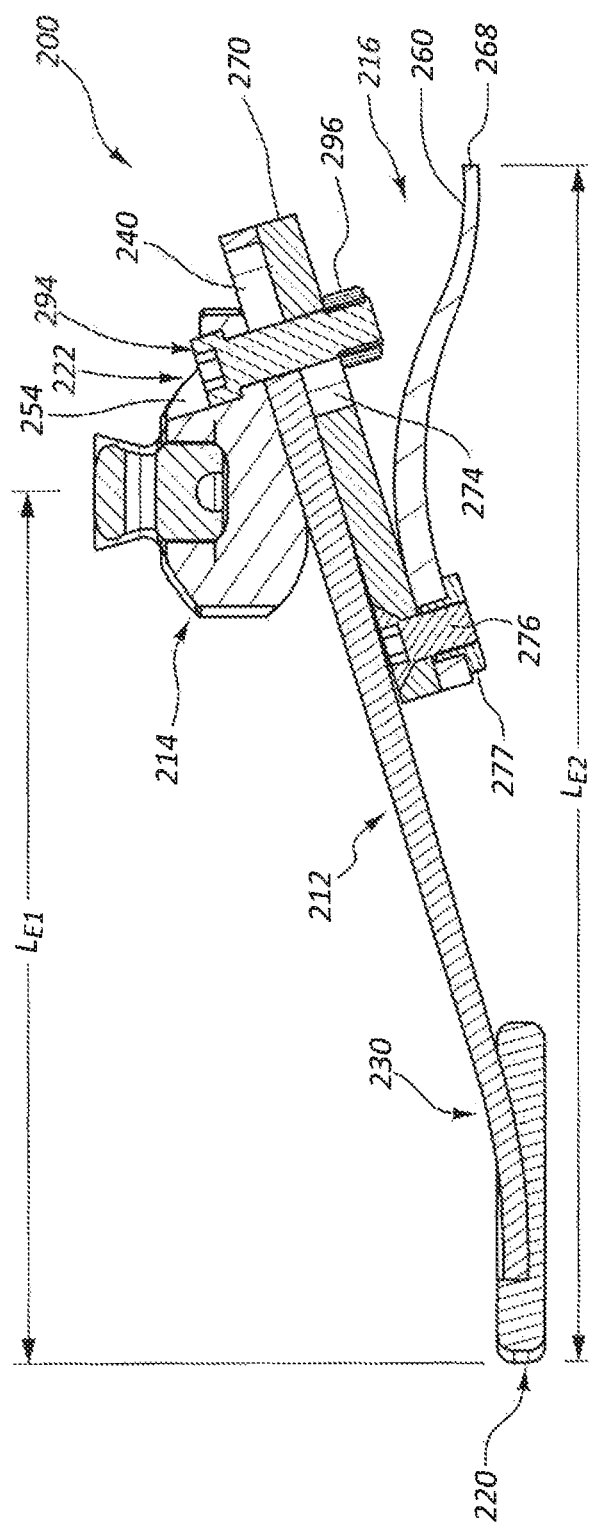
FIG. 24
FIG. 25

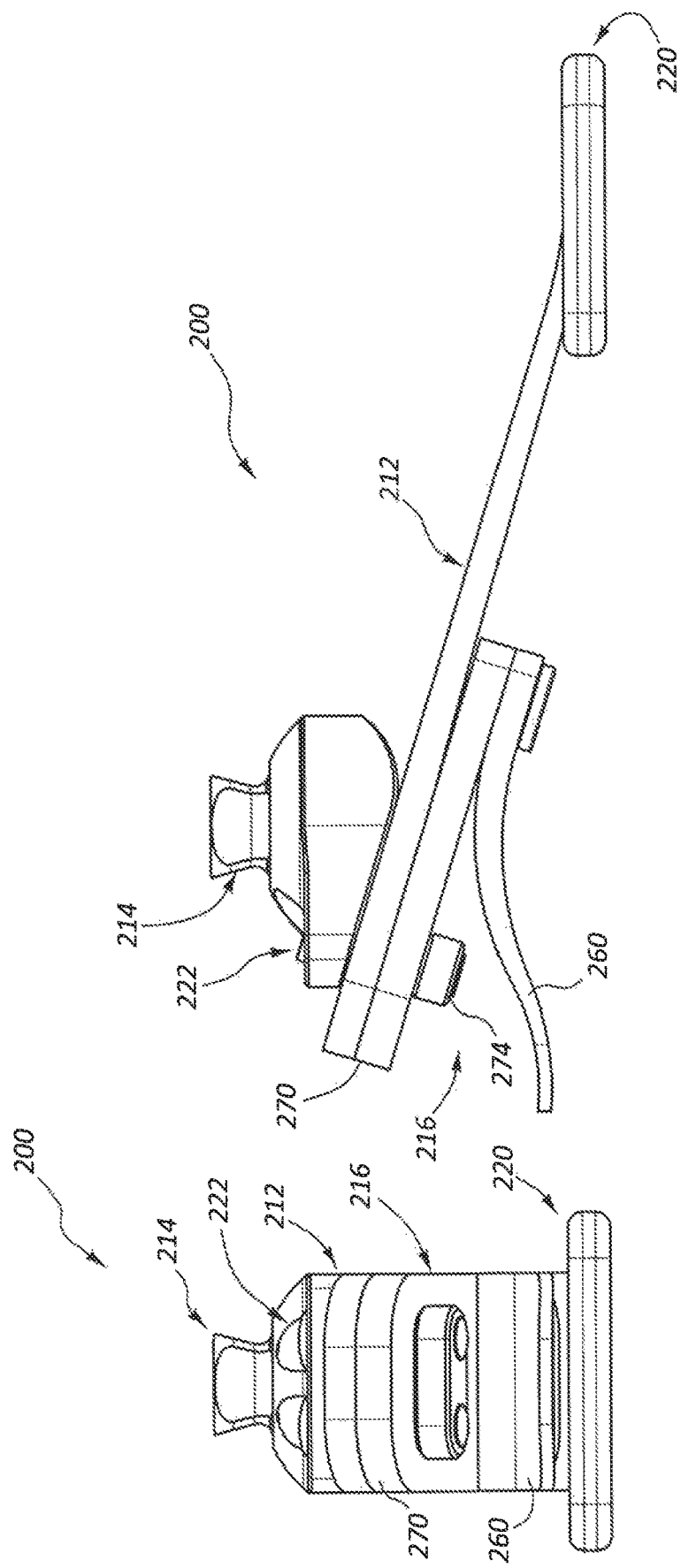

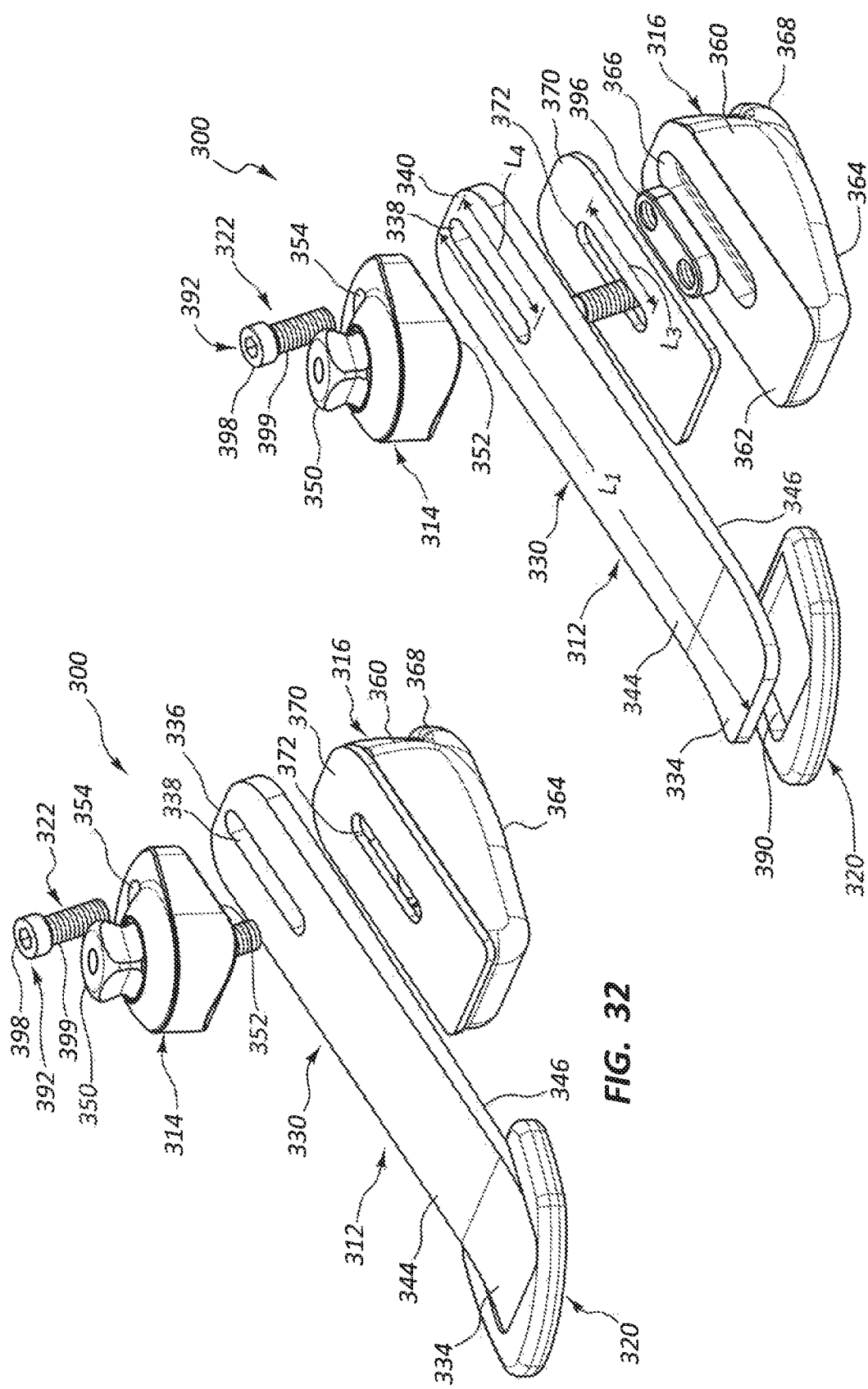

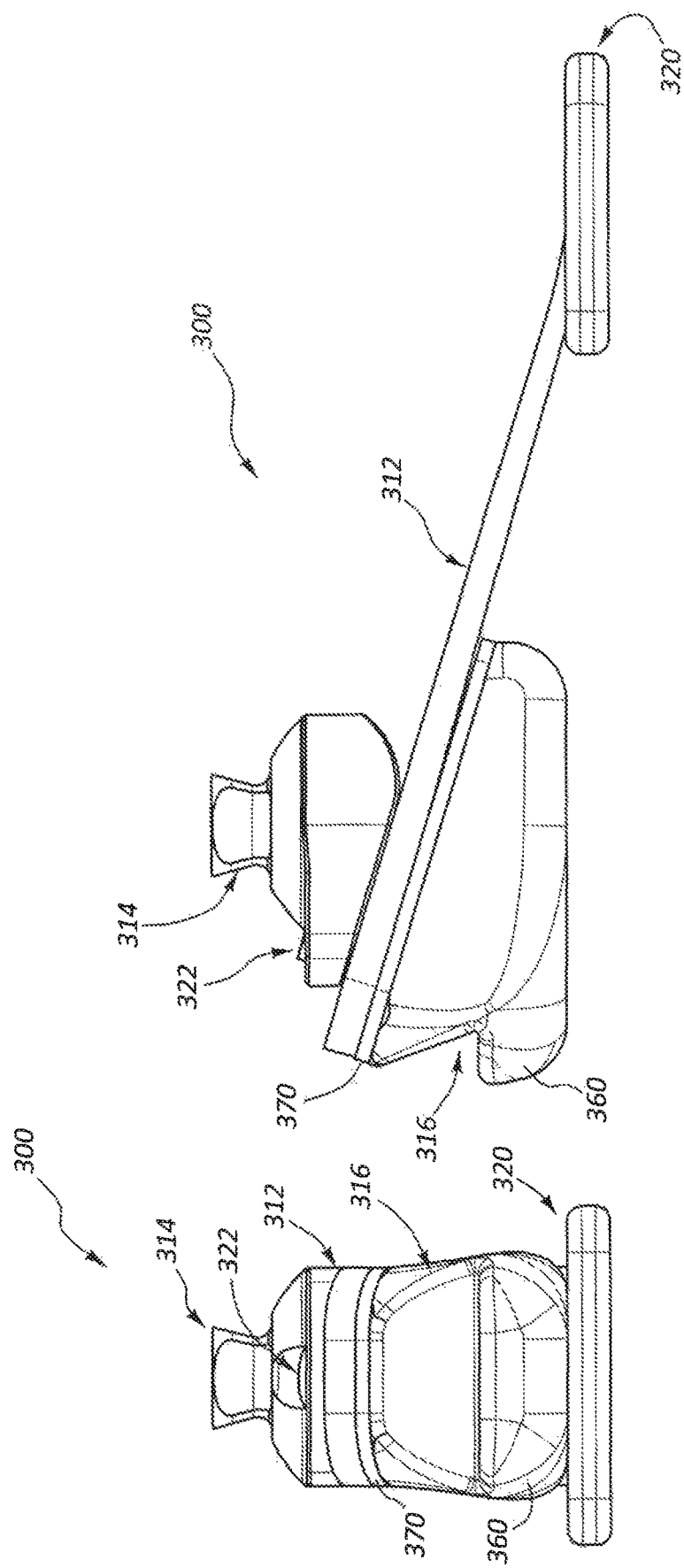

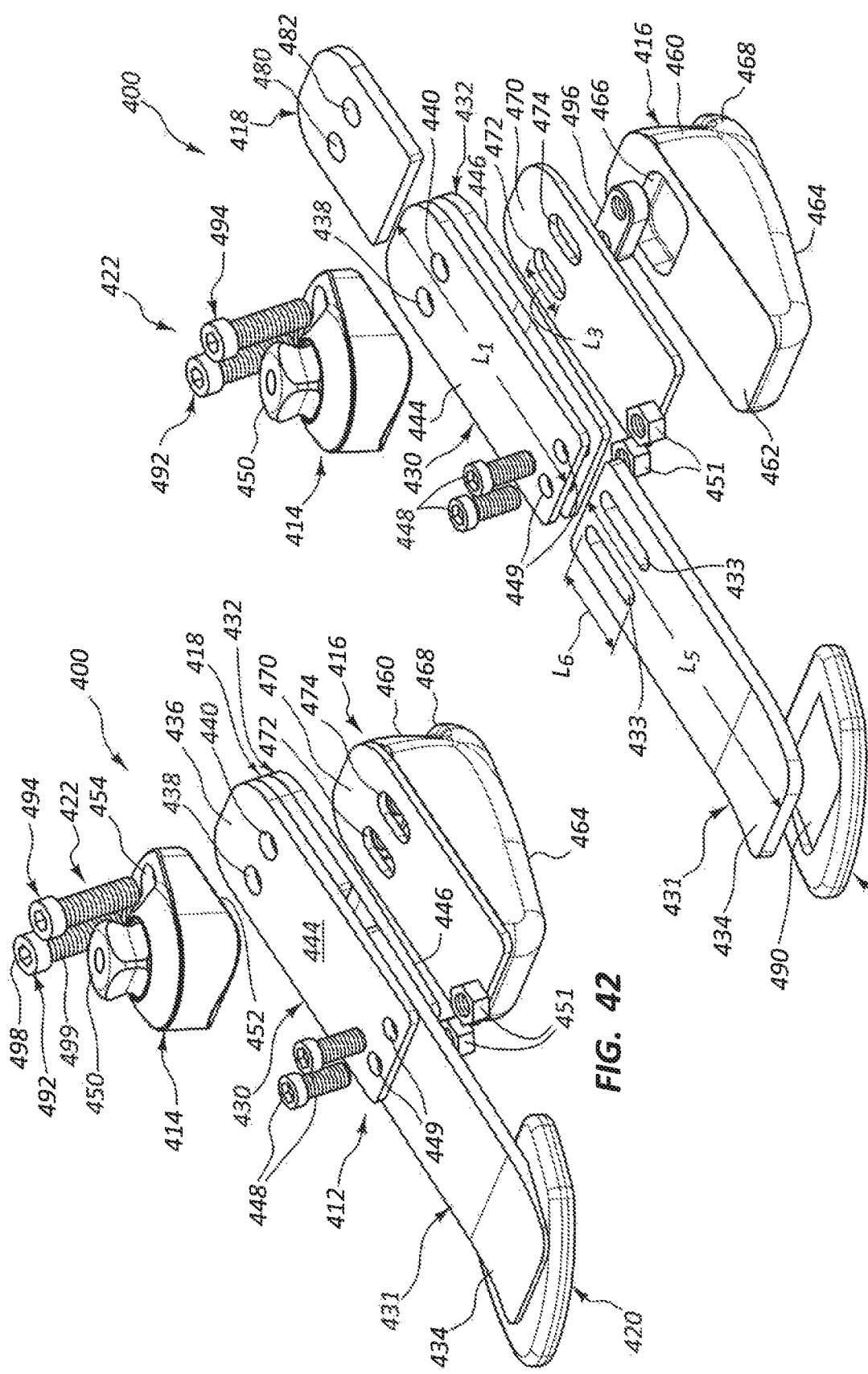

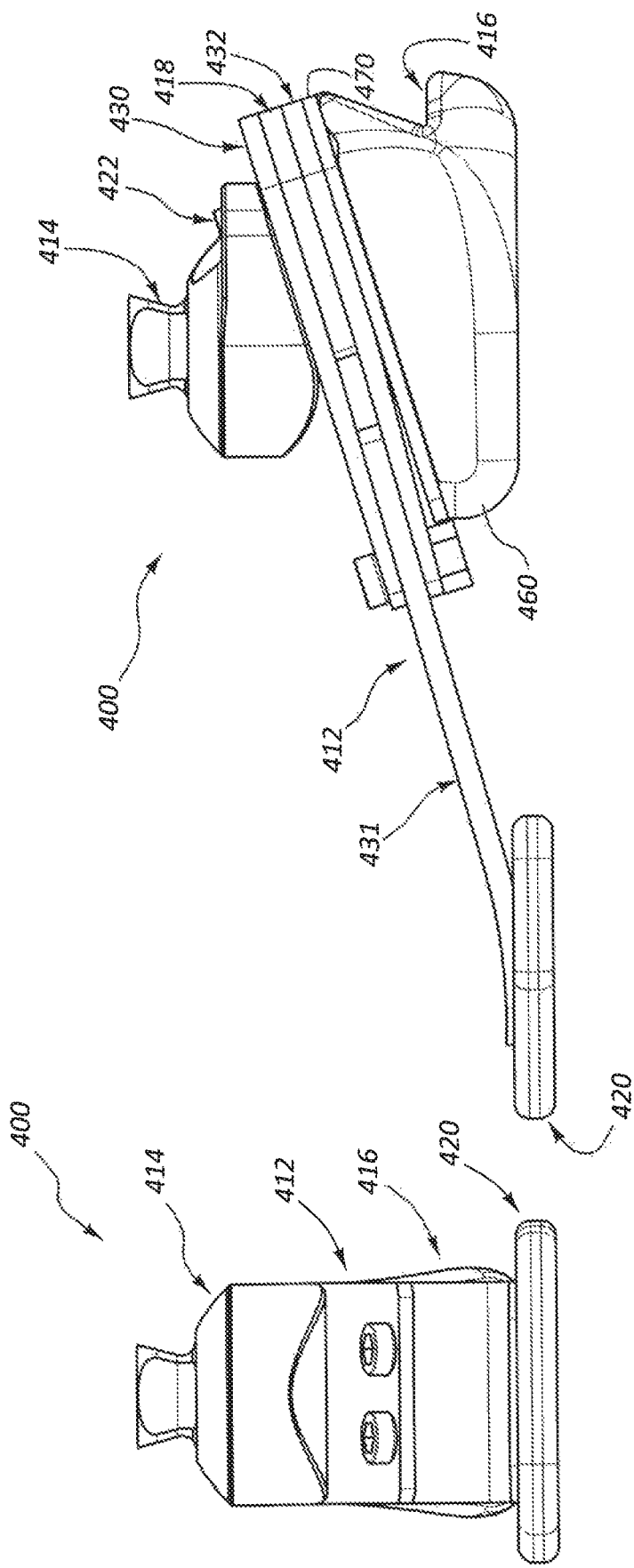

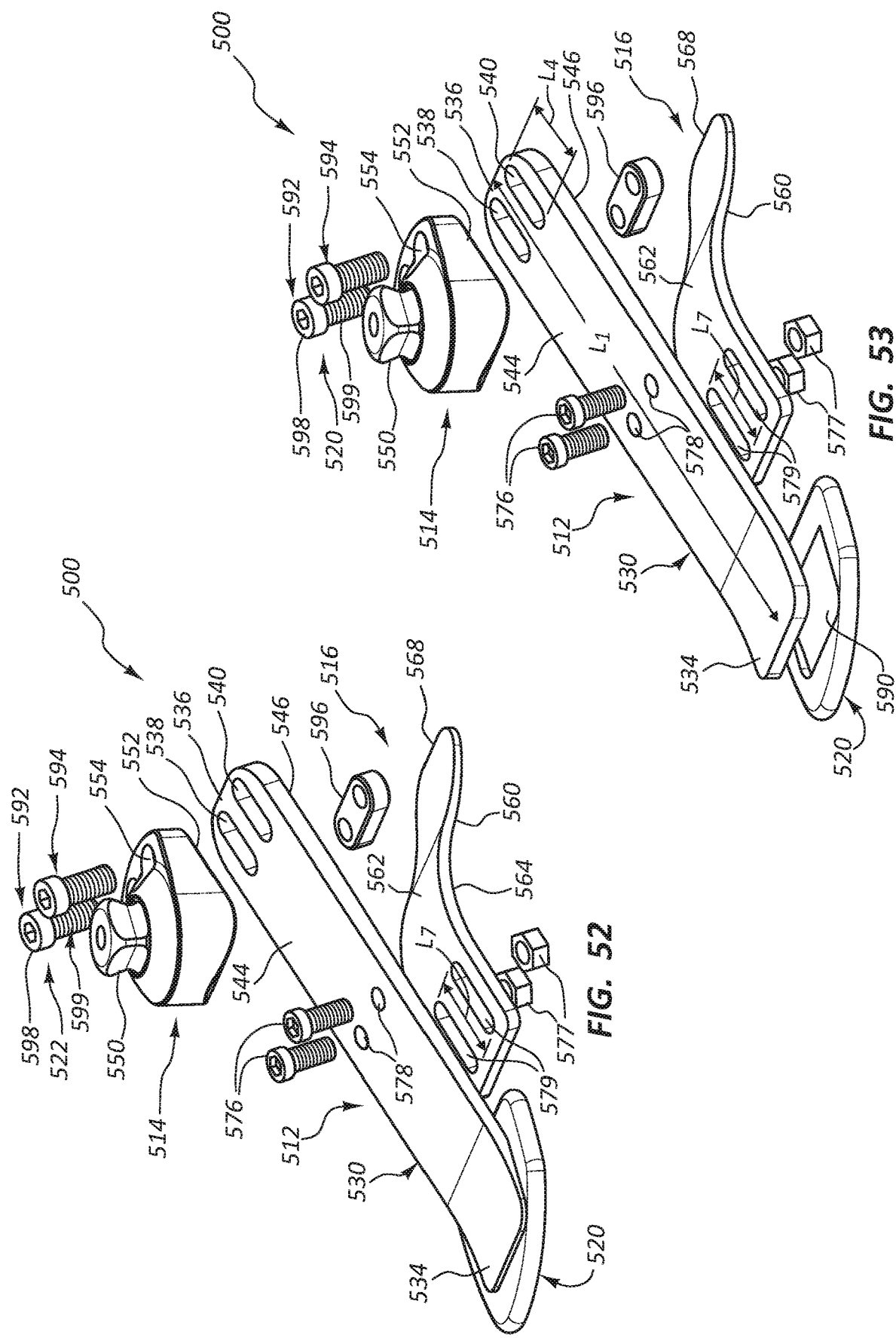

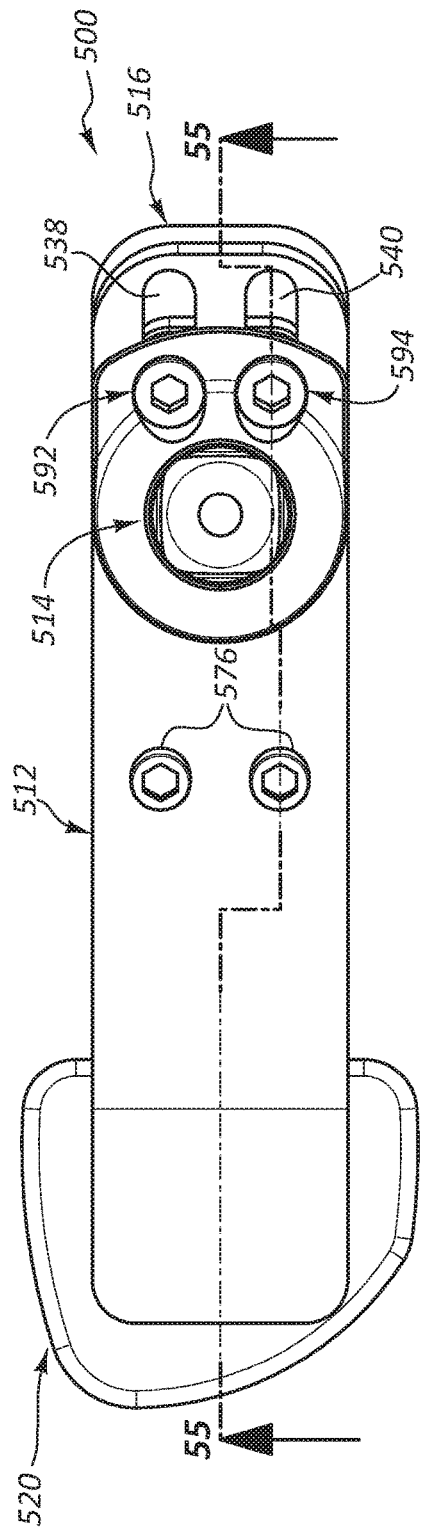
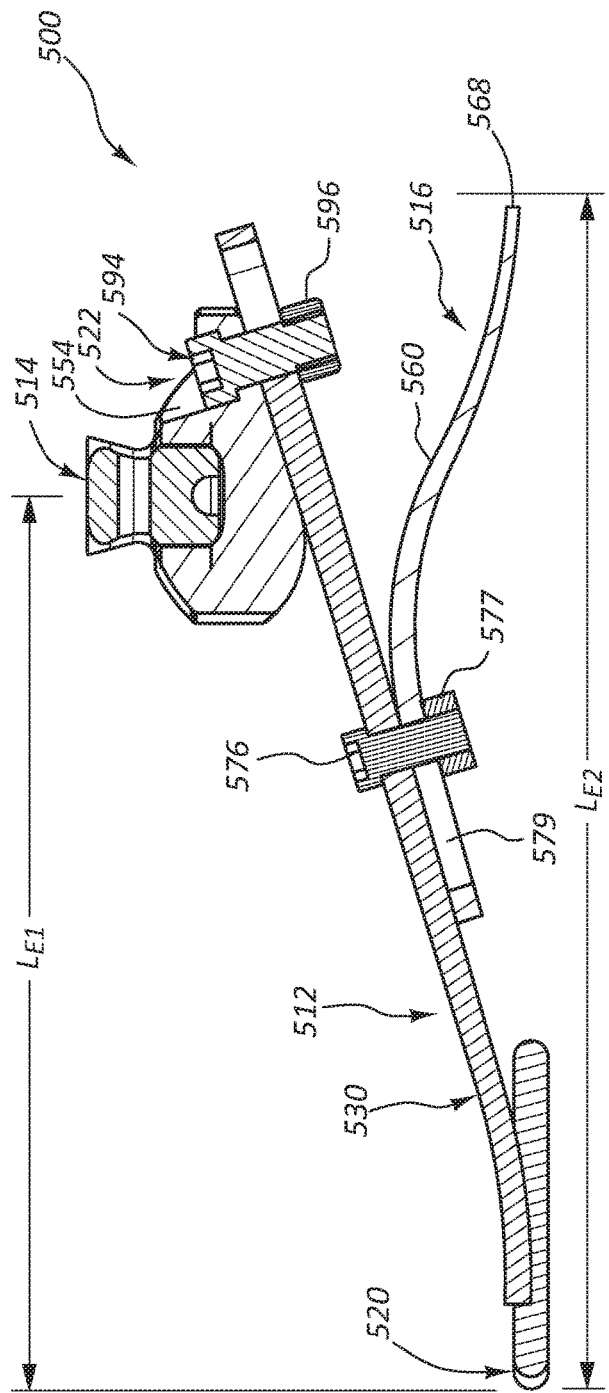
FIG. 54
FIG. 55

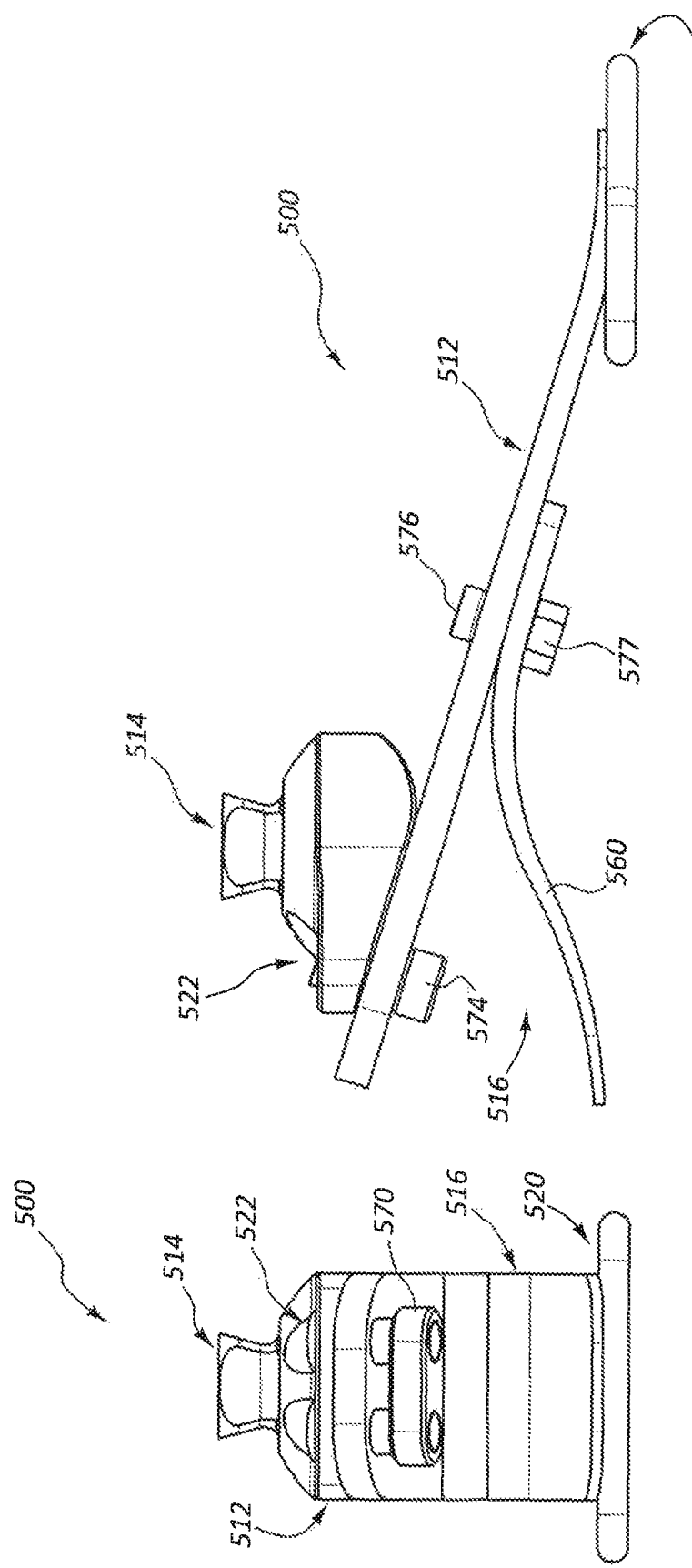

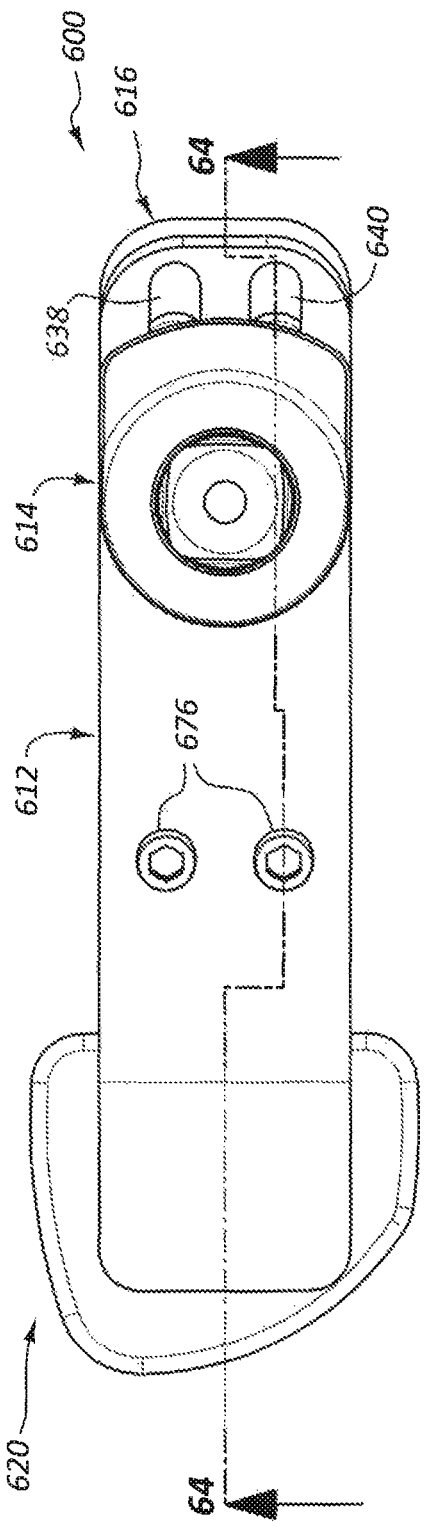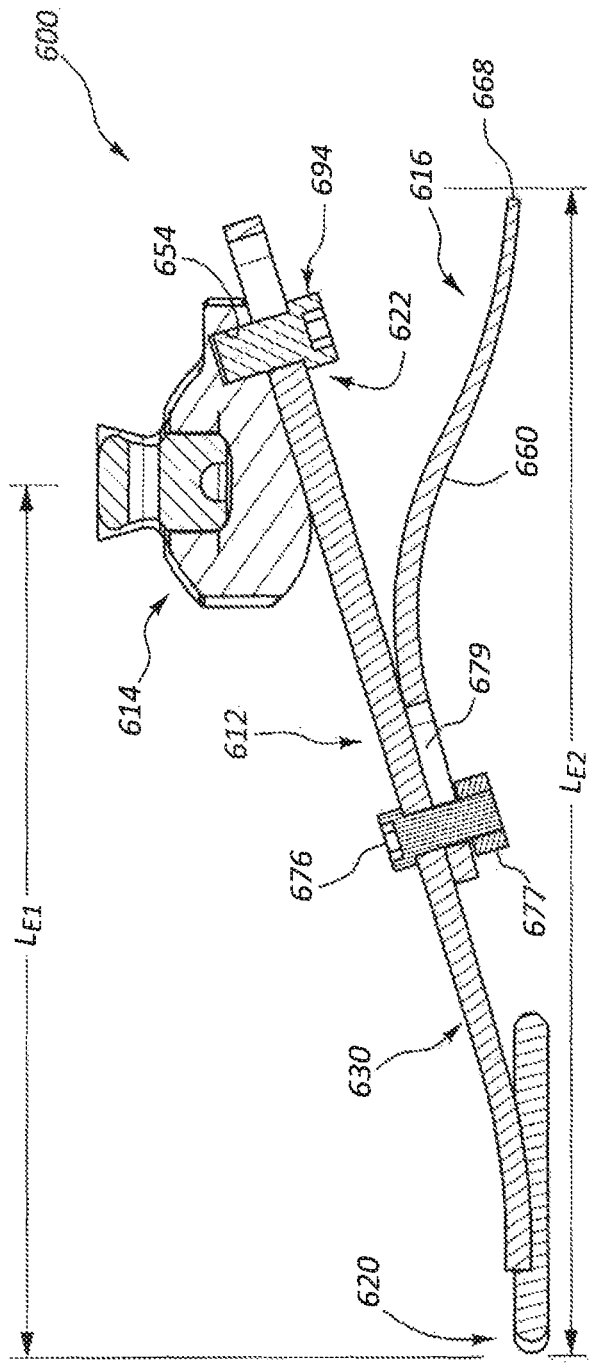

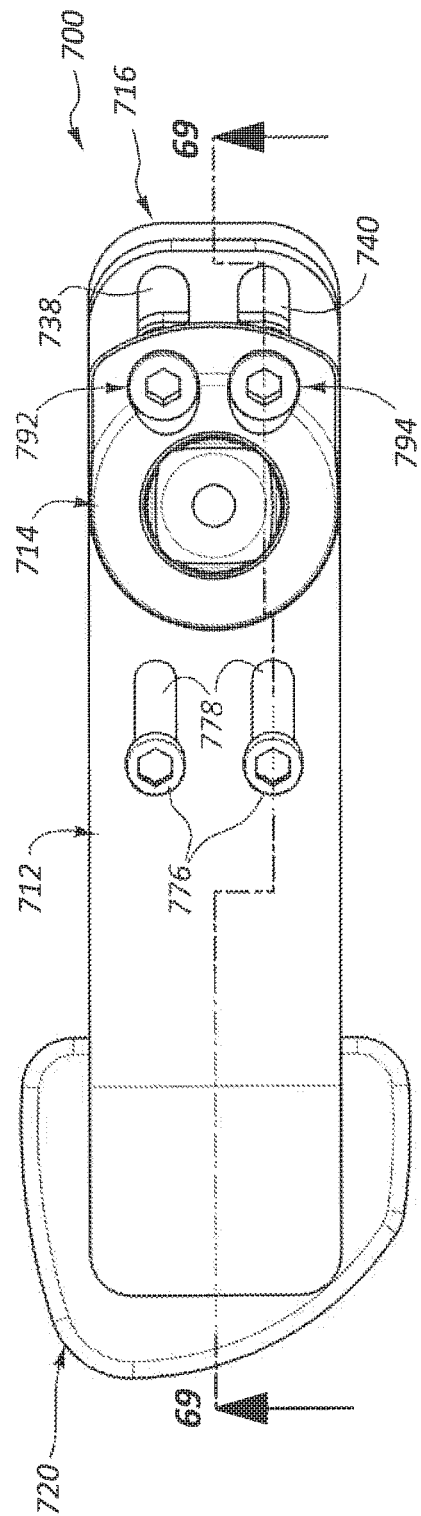
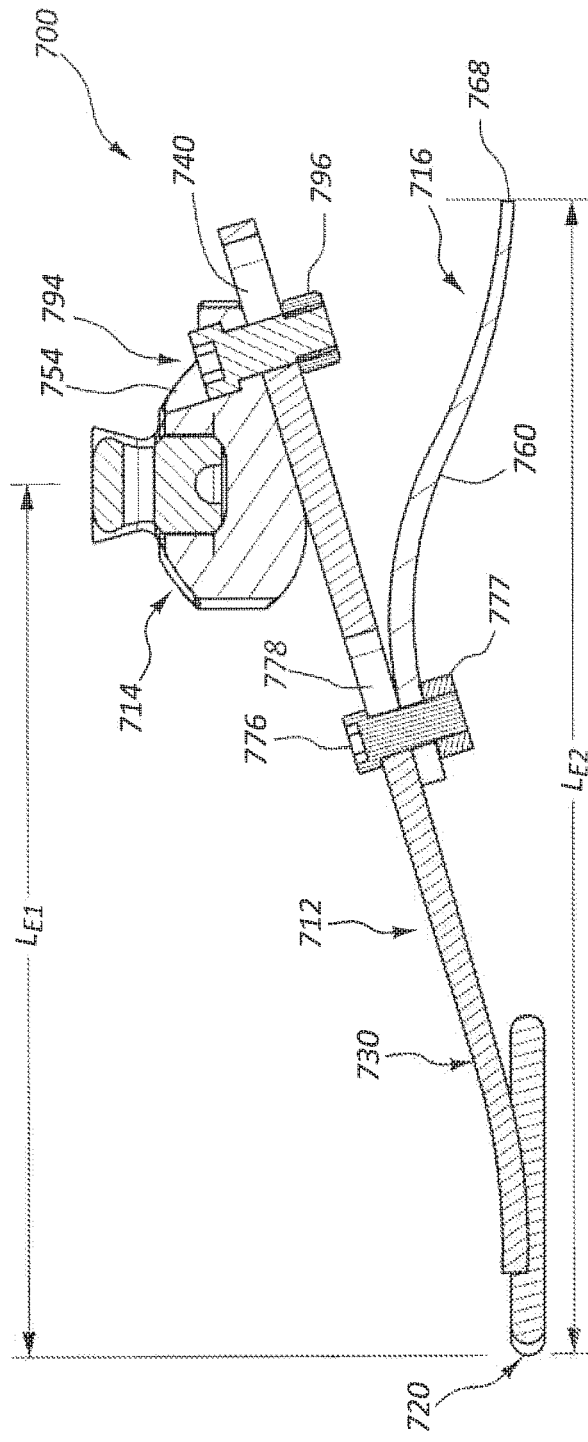

ADJUSTABLE STIFFNESS PROSTHETIC FOOT

RELATED APPLICATIONS

This is a continuation application of U.S. patent application Ser. No. 14/686,460 filed 14 Apr. 2015 and entitled ADJUSTABLE LENGTH PROSTHETIC FOOT, now U.S. Pat. No. 10,098,762, which claims the benefit of U.S. Provisional Application No. 61/979,485, filed 14 Apr. 2014 and entitled ADJUSTABLE LENGTH PROSTHETIC FOOT, the disclosures of which are incorporated, in their entireties, by this reference.

TECHNICAL FIELD

The present disclosure relates generally to prosthetic devices, and more particularly relates to prosthetic feet and adjustment features for prosthetic feet.

BACKGROUND

Amputees are typically fitted with prosthetic devices that meet specific criteria for that particular amputee. For example, the size, shape, stiffness, and other properties of a prosthetic device are selected to match the size, shape, strength, and other physical properties and functionality of the given amputee. Changes in the size, shape, strength, and other physical properties of a given amputee may influence whether or not a particular prosthetic device will perform properly and according to expectations for the amputee. It is common for an amputee to change his/her prosthetic device when, for example, the amputee grows in height, weight, strength, or balance capability.

The rapid physical changes in child amputees pose a number of challenges related to maintaining a properly operable prosthetic device for the child. Frequent changes in prosthetic devices as the child amputee's body changes is time consuming and costly, and creates challenges for providing comfort and performance associated with the prosthetic device.

Opportunities exist for providing prosthetic devices for amputees that account for changes in the amputee's body and capabilities.

SUMMARY

One aspect of the present disclosure relates to a foot prosthesis that includes at least one spring element, an attachment member, and a heel member. The at least one spring element has a toe end portion, a heel end portion, an upper surface, and a lower surface. The attachment member is mounted to the upper surface, and a position of the attachment member is adjustable along a length of the at least one spring element. The attachment member is configured to connect the foot prosthesis to a lower limb prosthesis component. The heel member is mounted below the lower surface of the at least one spring element, and a position of the heel member is adjustable along the length of the at least one spring element.

The at least one spring element may include first and second spring elements. The first and second spring elements may be fixed to each other at the toe end portion. The foot prosthesis may include a spacer positioned between the first and second spring elements and adjustable relative to the first and second spring elements to change a stiffness of the foot prosthesis. The foot prosthesis may include at least one fastener that connects the attachment member and the heel member to the at least one spring element. The at least one spring element may include at least one slot arranged longitudinally, and the at least one fastener may extend through the at least one slot. The at least one fastener may include at least two threadable bolts or screws. The heel member may include a foam member and a plate mounted to a top surface of the foam member, wherein the at least one fastener may extend through the plate. The attachment member and the heel member may maintain alignment with each other when being adjusted along the length of the at least one spring element.

Another aspect of the present disclosure relates to a length adjustable prosthetic foot that includes a spring assembly, a prosthetic attachment member, and a heel member. The spring assembly has a heel end portion and a toe end portion. The prosthetic attachment member is adjustably mounted to the spring assembly. The heel member is adjustably mounted to the spring assembly. At least one of the prosthetic attachment member and the heel member are adjustable along a length of the spring assembly to adjust a functional length of the prosthetic foot.

The prosthetic attachment member and the heel member may move in tandem relative to the spring assembly. The spring assembly may include first and second spring elements fixed to each other at the toe end portion. The prosthetic foot may include a spacer positioned between the first and second spring elements and adjustable along at least a portion of a length of the first and second spring elements to adjust a stiffness of the length adjustable prosthetic foot. The spring assembly may include at least first and second slots receptive of at least first and second fasteners, wherein the at least first and second fasteners may be configured to connect the prosthetic attachment member and the heel member to the spring assembly at variable positions along the length of the spring assembly. The spring assembly may include at least first and second spring elements and a spacer positioned between the first and second spring elements, wherein the spacer includes at least first and second slots aligned with the at least first and second slots of the first and second spring elements.

A further aspect of the present disclosure relates to a prosthetic foot that includes a spring assembly, a prosthetic attachment member, a heel member, and a connection assembly. The spring assembly includes a top spring element and a bottom spring element positioned vertically below the top spring element. The prosthetic attachment member is positioned vertically above the top spring element. The heel member is positioned vertically below the bottom spring element. The connection assembly is configured to adjustably connect the prosthetic attachment member and the heel member to the spring assembly at variable positions along a length of the spring assembly.

The prosthetic foot may include a spacer positioned between the top and bottom spring elements, wherein the spacer is replaceable by spacers of different lengths to alter a stiffness of the spring assembly. The connection assembly may include at least one fastener that extends through the spring assembly and is connected to the prosthetic attachment member and the heel member. The heel member may include at least one heel spring member.

Another aspect of the present disclosure relates to a method of adjusting an effective length of a foot prosthesis. The method includes providing at least one spring element, a prosthetic attachment member, and a heel member, mounting the prosthetic attachment member to an upper surface of the at least one spring element, mounting the heel member to a lower surface of the at least one spring element, and adjusting a position of at least one of the prosthetic attachment member and the heel member along a length of the at least one spring element to adjust an effective length of the foot prosthesis.

The method may also include providing at least one fastener configured to adjustably secure the prosthetic attachment member and the heel member to the at least one spring element at each position along the length of the at least one spring element. The at least one spring element may include at least first and second spring elements, and the method may include providing a spacer positioned between the first and second spring elements and adjustable to alter a stiffness of the foot prosthesis. The at least one spring element may include at least one slot extending longitudinally, and the method may include extending at least one fastener through the at least one slot and connecting the at least one fastener to the prosthetic attachment member and the heel member. Adjusting a position of at least one of the prosthetic attachment member and the heel member along a length of the at least one spring element may include loosening at least one fastener, sliding the prosthetic attachment member and the heel member along the length of the at least one spring element, and tightening the at least one fastener.

A further aspect of the present disclosure is directed to an adjustable prosthetic foot that includes at least one heel member, at least one spring element, and a prosthetic pyramid connector. The at least one spring element includes a toe end portion, a heel end portion, and an upper surface. The prosthetic pyramid connector is configured to connect the prosthetic foot to a lower limb prosthetic component and is slidably mounted along the upper surface of the at least one spring element.

The at least one heel member may be independently adjustable relative to the prosthetic pyramid connector in a lengthwise direction of the foot prosthesis. The prosthetic pyramid connector may be adjustable along a lengthwise direction of the foot prosthesis relative to the at least one spring element.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the spirit and scope of the appended claims. Features which are believed to be characteristic of the concepts disclosed herein, both as to their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the embodiments may be realized by reference to the following drawings. In the appended figures, similar components or features may have the same reference label.

FIG. 2 is an exploded isometric view of the prosthetic foot of FIG. 1.

FIG. 3 is another exploded isometric view of the prosthetic foot of FIG. 1.

FIG. 6 is a left side view of the prosthetic foot of FIG. 1.

FIG. 7 is a front view of the prosthetic foot of FIG. 1.

FIG. 8 is a right side view of the prosthetic foot of FIG. 1.

FIG. 9 is a rear view of the prosthetic foot of FIG. 1.

FIG. 12 is an exploded isometric view of the prosthetic foot of FIG. 11.

FIG. 13 is another exploded isometric view of the prosthetic foot of FIG. 11.

FIG. 14 is a top view of the prosthetic foot of FIG. 11.

FIG. 15 is a cross-sectional view of the prosthetic foot shown in FIG. 14, taken along cross-section indicators 15-15.

FIG. 18 is a right side view of the prosthetic foot of FIG. 11.

FIG. 19 is a rear view of the prosthetic foot of FIG. 11.

FIG. 22 is an exploded isometric view of the prosthetic foot of FIG. 21.

FIG. 23 is another exploded isometric view of the prosthetic foot of FIG. 21.

FIG. 24 is a top view of the prosthetic foot of FIG. 21.

FIG. 25 is a cross-sectional view of the prosthetic foot shown in FIG. 24, taken along cross-section indicators 25-25.

FIG. 28 is a right side view of the prosthetic foot of FIG. 21.

FIG. 29 is a rear view of the prosthetic foot of FIG. 21.

FIG. 32 is an exploded isometric view of the prosthetic foot of FIG. 31.

FIG. 33 is another exploded isometric view of the prosthetic foot of FIG. 31.

FIG. 38 is a right side view of the prosthetic foot of FIG. 31.

FIG. 39 is a rear view of the prosthetic foot of FIG. 31.

FIG. 42 is an exploded isometric view of the prosthetic foot of FIG. 41.

FIG. 43 is another exploded isometric view of the prosthetic foot of FIG. 41.

FIG. 46 is a left side view of the prosthetic foot of FIG. 41.

FIG. 47 is a front view of the prosthetic foot of FIG. 41.

FIG. 52 is an exploded isometric view of the prosthetic foot of FIG. 51.

FIG. 53 is another exploded isometric view of the prosthetic foot of FIG. 51.

FIG. 54 is a top view of the prosthetic foot of FIG. 51.

FIG. 55 is a cross-sectional view of the prosthetic foot shown in FIG. 54, taken along cross-section indicators 55-55.

FIG. 58 is a right side view of the prosthetic foot of FIG. 51.

FIG. 59 is a rear view of the prosthetic foot of FIG. 51.

FIG. 63 is a top view of the prosthetic foot of FIG. 61.

FIG. 64 is a cross-sectional view of the prosthetic foot shown in FIG. 63, taken along cross-section indicators 64-64.

FIG. 68 is a top view of the prosthetic foot of FIG. 66.

FIG. 69 is a cross-sectional view of the prosthetic foot shown in FIG. 68, taken along cross-section indicators 69-69.

Figure 1:
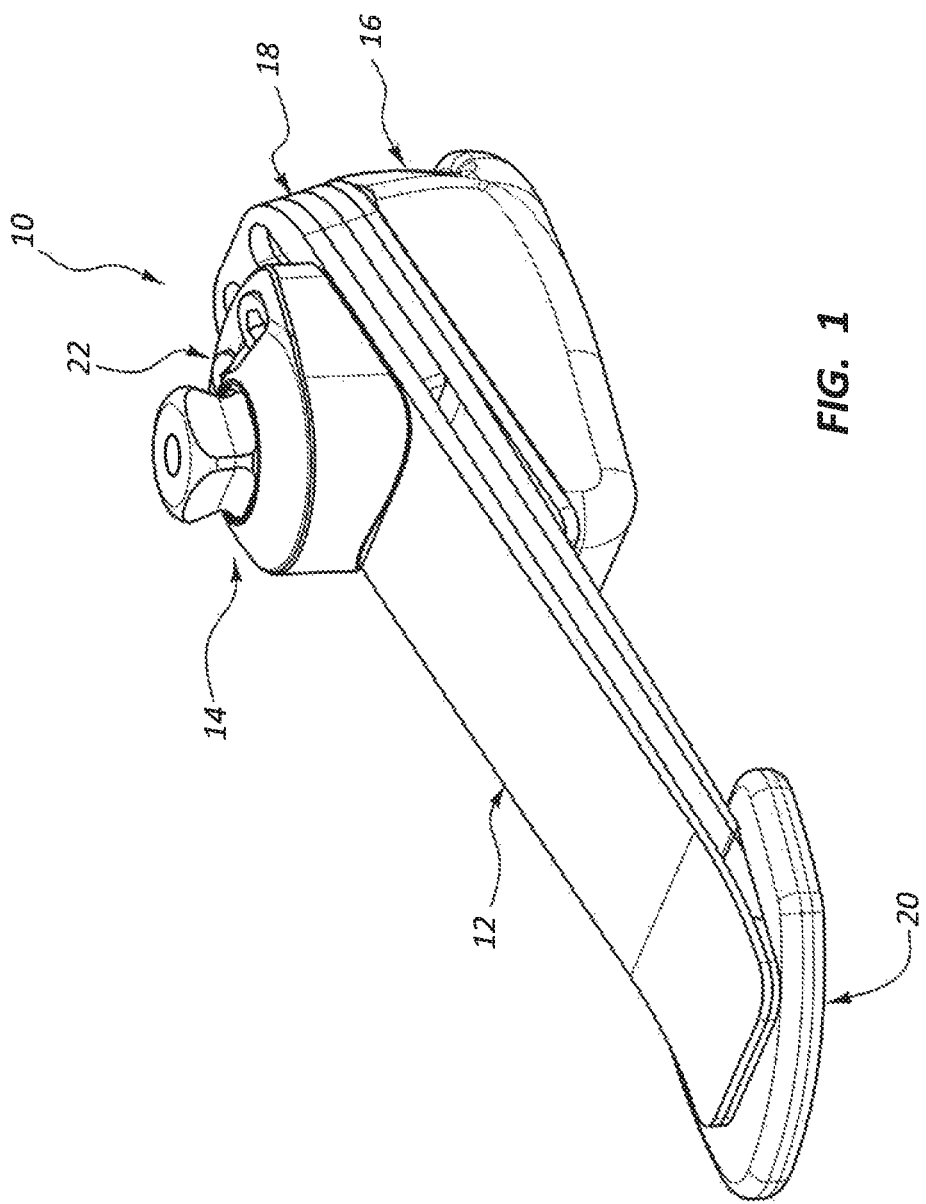
FIG. 1 is an isometric view of an example prosthetic foot in accordance with the present disclosure.
Figure 4:
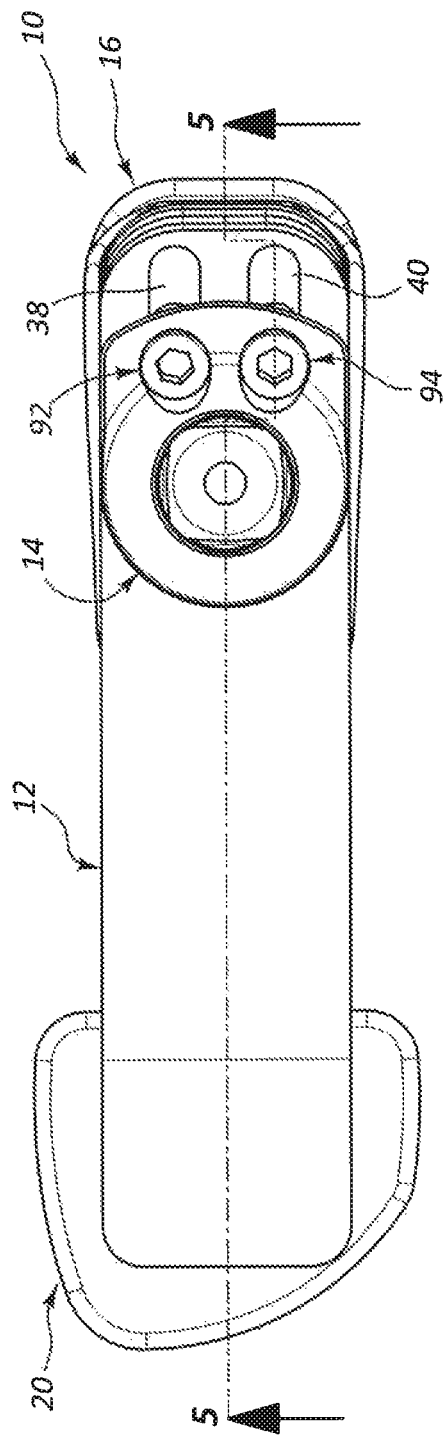
FIG. 4 is a top view of the prosthetic foot of FIG. 1.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

The present disclosure is generally directed to prosthetic devices, and more particularly relates to prosthetic foot devices, which are also referred to as a foot prostheses. The foot prosthesis embodiments disclosed herein have an adjustable length, wherein the length may be referred to as an effective length or a functional length, and the prosthetic foot may be referred to as an adjustable prosthetic foot, an adjustable length foot prosthesis, or variations thereof. The effective length is measured longitudinally along the prosthetic foot from an anterior-most toe portion to either a location of an attachment member (which is used to attach the prosthetic foot to another prosthetic device and may be referred to as a prosthetic attachment member, a prosthetic connector, a pyramid connector, a prosthetic pyramid connector, or variations thereof) or to an posterior-most point of a heel member of the prosthetic foot. The length adjustability may be provided by adjustability of the attachment member relative to a spring element of the prosthetic foot, by adjustability of a heel member relative to the spring element of the prosthetic foot, or a combination thereof. In other embodiments, the length adjustability may be provided by relative adjustability between one or more spring elements of the prosthetic foot. Providing the prosthetic foot with length adjustability permits the user (e.g., amputee) to adjust the properties of the prosthetic foot for any of a variety of reasons including, for example, changes in the user's body.

One particularly useful application for the disclosed adjustable length foot prosthesis is with children (pediatric) amputees. The foot prosthesis is able to be adjusted in length as the child grows in height and/or weight. The foot prosthesis might include other adjustability features, such as adjustments in stiffness of the foot prosthesis to counterbalance the effects of changing the effective length of the foot prosthesis. The adjustment features of the foot prosthesis embodiments disclosed herein may make it possible to use a single foot prosthesis for several years of a child amputee's life during which time it is otherwise typical for the child amputee to use several different sized foot prostheses to accommodate his/her growing body.

FIGS. 1-10 show an example prosthetic foot 10 that incorporates at least some of the length adjustment and other adjustability features mentioned above. The prosthetic foot 10 includes a spring assembly 12, an attachment member 14, a heel assembly 16, a spacer 18, a toe pad 20, and a connection assembly 22, as shown in at least the exploded isometric views of FIGS. 2 and 3. When assembled, as shown in at least FIG. 1, prosthetic foot 10 provides for an adjustment in at least one of the effective lengths $L_{E1}$, $L_{E2}$ of the prosthetic foot 10 (see FIG. 5). For purposes of the present disclosure, the effective length $L_{E1}$ is measured from an anterior-most point defined by toe pad 20 to a central axis (e.g., vertical axis) of connector 50 of attachment member 14. The effective length $L_{E2}$ is measured from an anterior-most point defined by the toe pad 20 to a posterior-most point defined by heel assembly 16 (e.g., posterior edge 68).

Typically, the attachment member 14 and heel assembly 16 move together in a longitudinal direction along a length of the spring assembly 12 to adjust the effective lengths $L_{E1}$, $L_{E2}$. In other embodiments, the attachment member 14 and heel assembly 16 are independently movable longitudinally relative to spring assembly 12 to adjust the effective lengths $L_{E1}$, $L_{E2}$ or provide other adjustability for prosthetic foot 10, such as adjusting a center of gravity location applied to prosthetic foot 10 via attachment member 14.

Referring primarily to FIGS. 2 and 3, spring assembly 12 includes first and second spring elements 30, 32, a toe end portion 34, a heel end portion 36, first and second slots 38, 40, a bond region 42, and top and bottom surfaces 44, 46.

Figure 5:
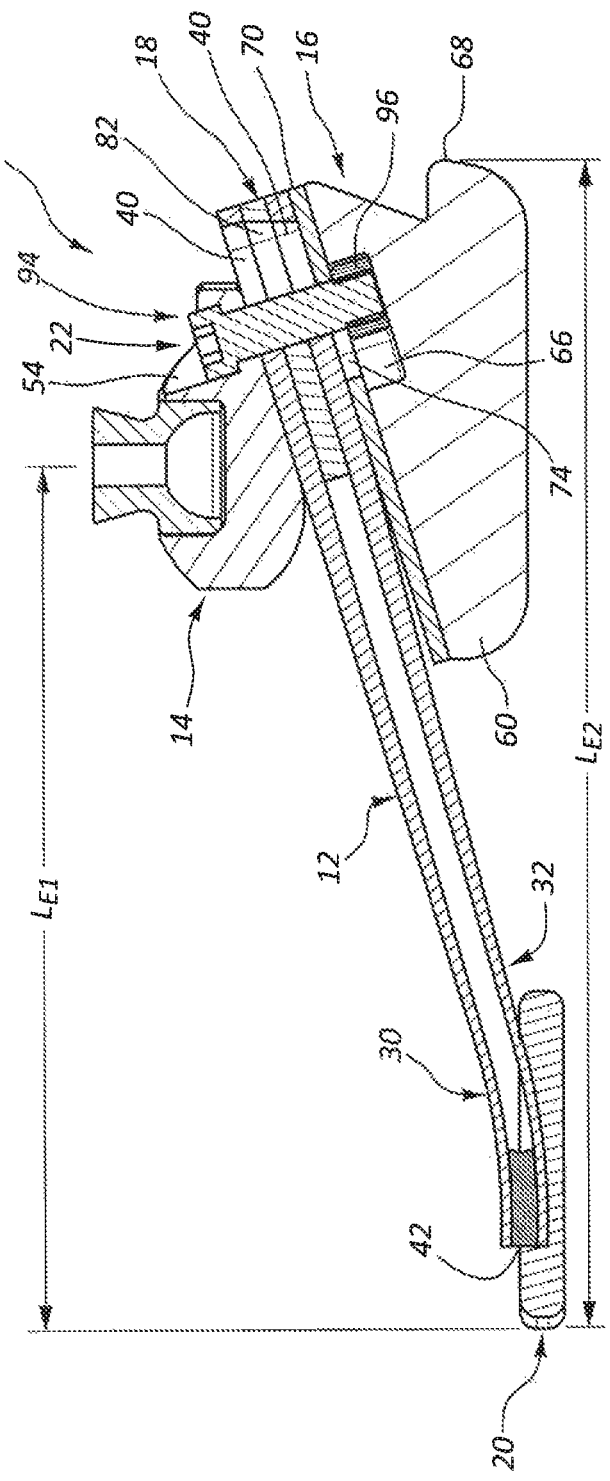
FIG. 5 is a cross-sectional view of the prosthetic foot shown in FIG. 4, taken along cross-section indicators 5-5.
Figure 10:
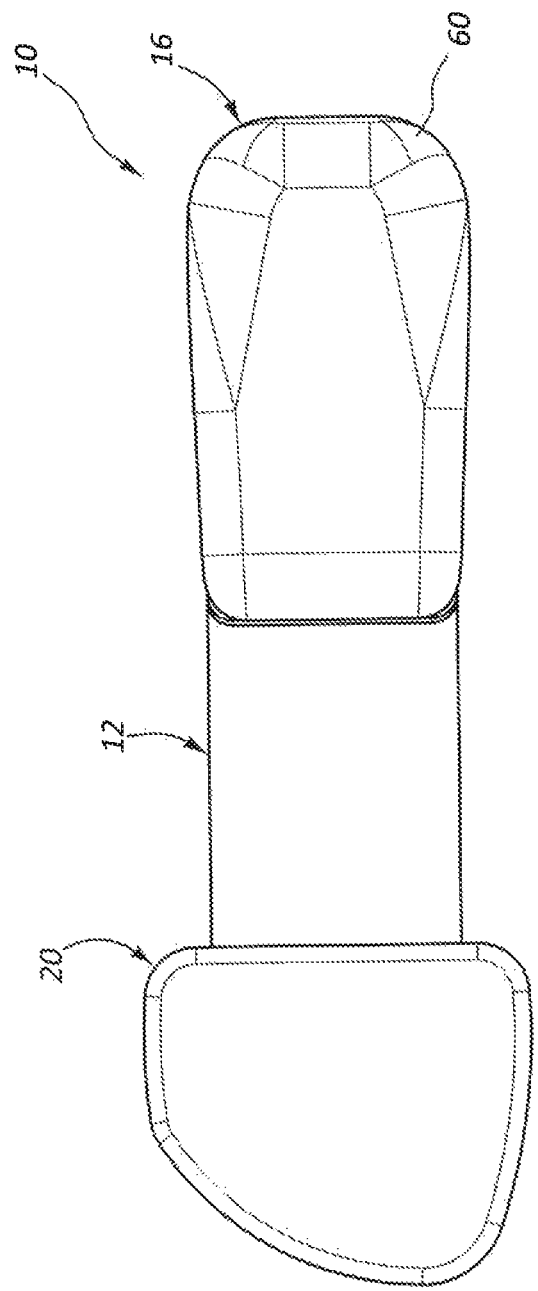
FIG. 10 is a bottom view of the prosthetic foot of FIG. 1.
Figure 11:
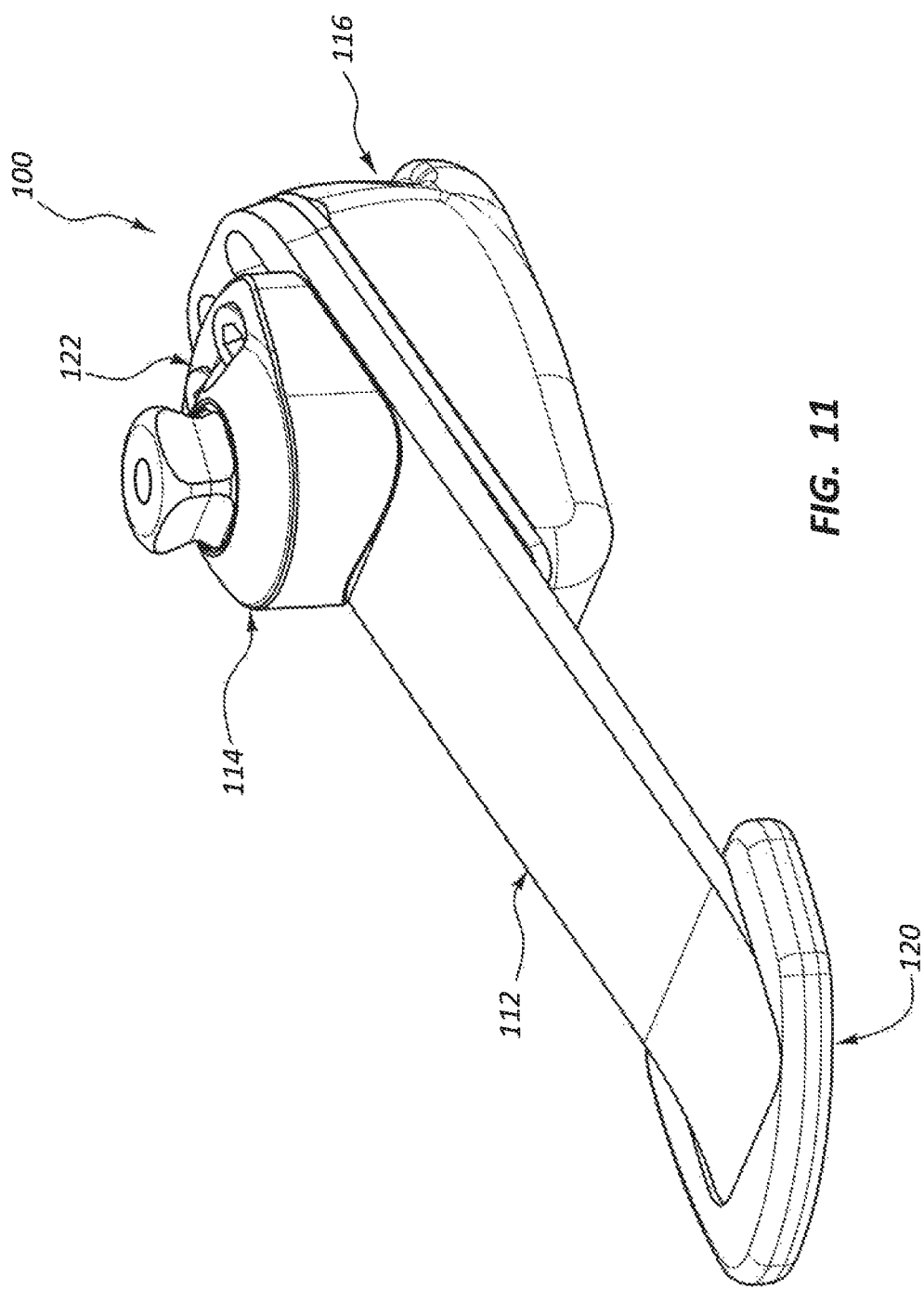
FIG. 11 is an isometric view of an example prosthetic foot in accordance with the present disclosure.
Figure 16:
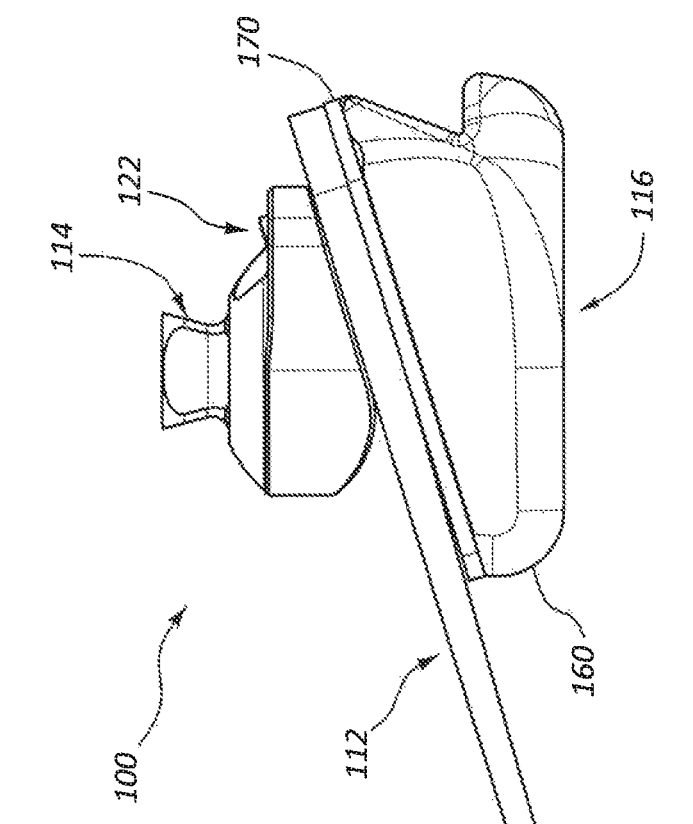
FIG. 16 is a left side view of the prosthetic foot of FIG. 11.
Figure 17:
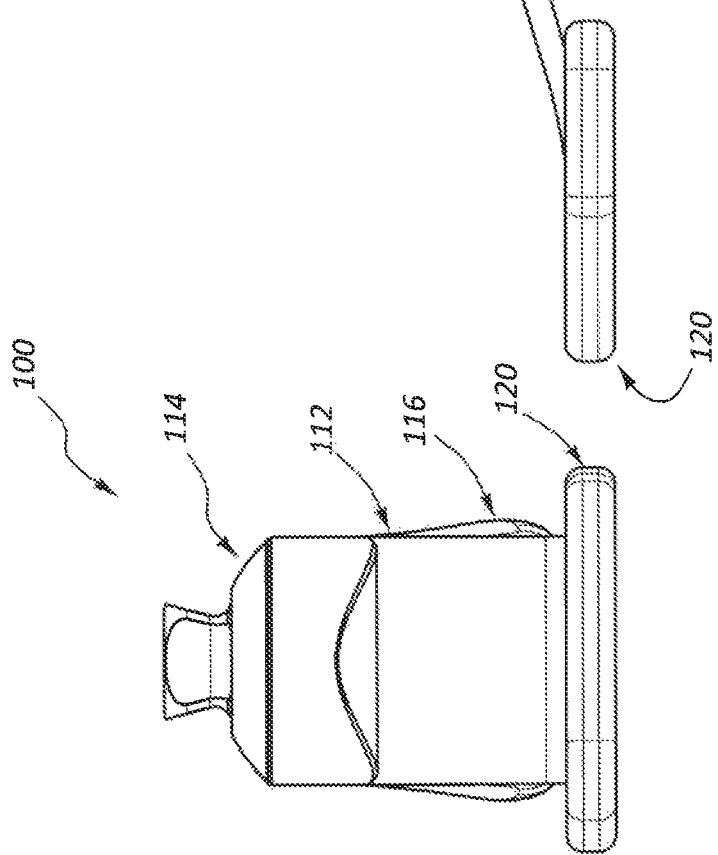
FIG. 17 is a front view of the prosthetic foot of FIG. 11.
Figure 20:
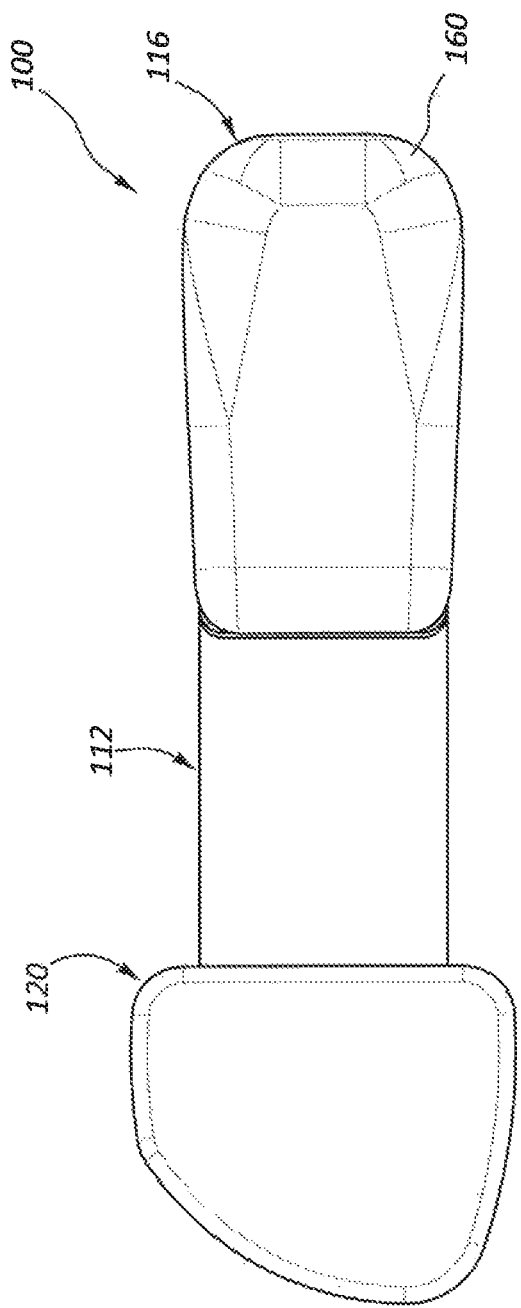
FIG. 20 is a bottom view of the prosthetic foot of FIG. 11.
Figure 21:
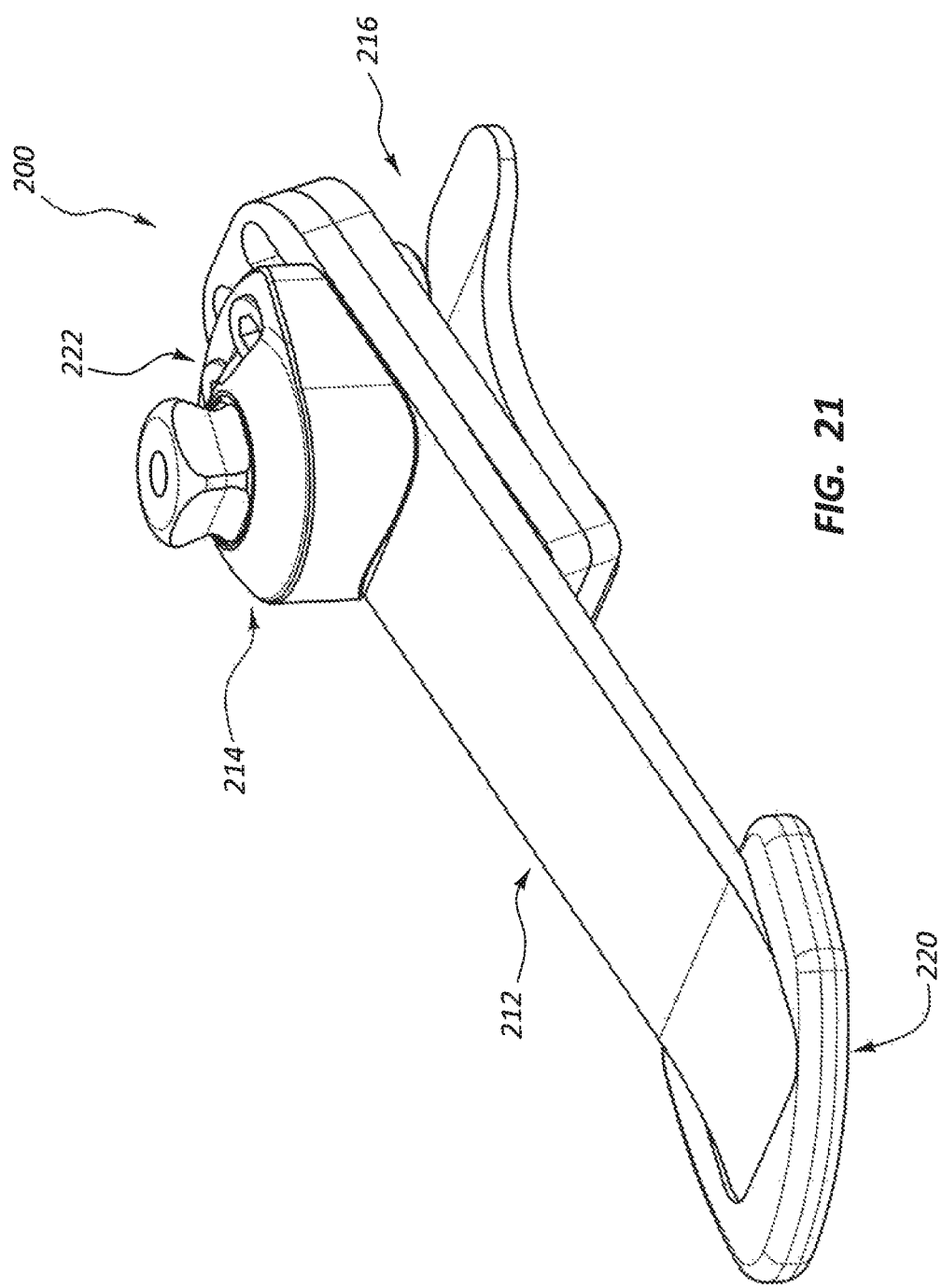
FIG. 21 is an isometric view of an example prosthetic foot in accordance with the present disclosure.
Figures 26, 27:
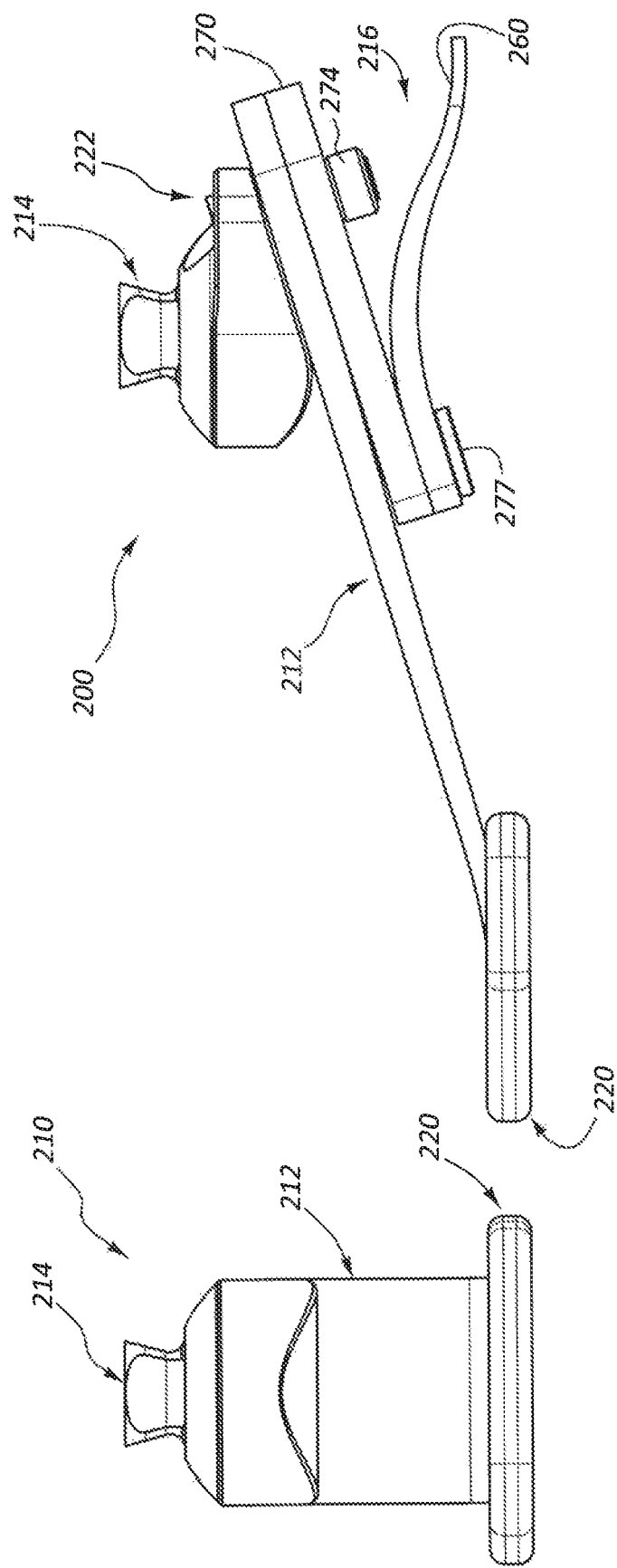
FIG. 26 is a left side view of the prosthetic foot of FIG. 21.
FIG. 27 is a front view of the prosthetic foot of FIG. 21.
Figure 30:
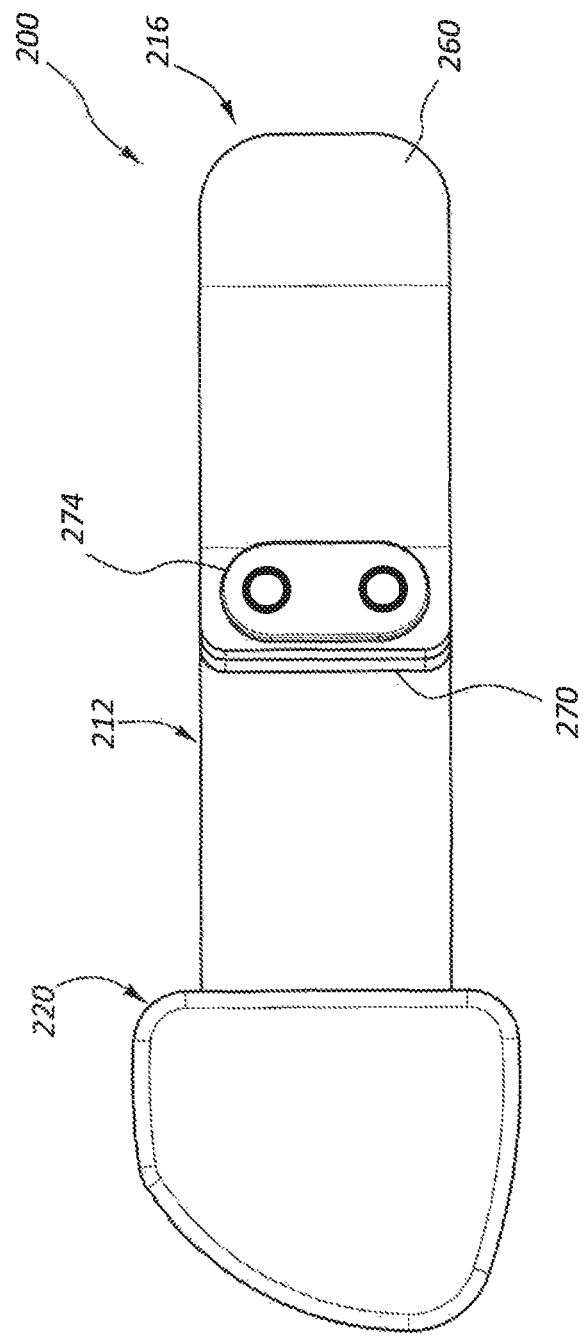
FIG. 30 is a bottom view of the prosthetic foot of FIG. 21.
Figure 31:
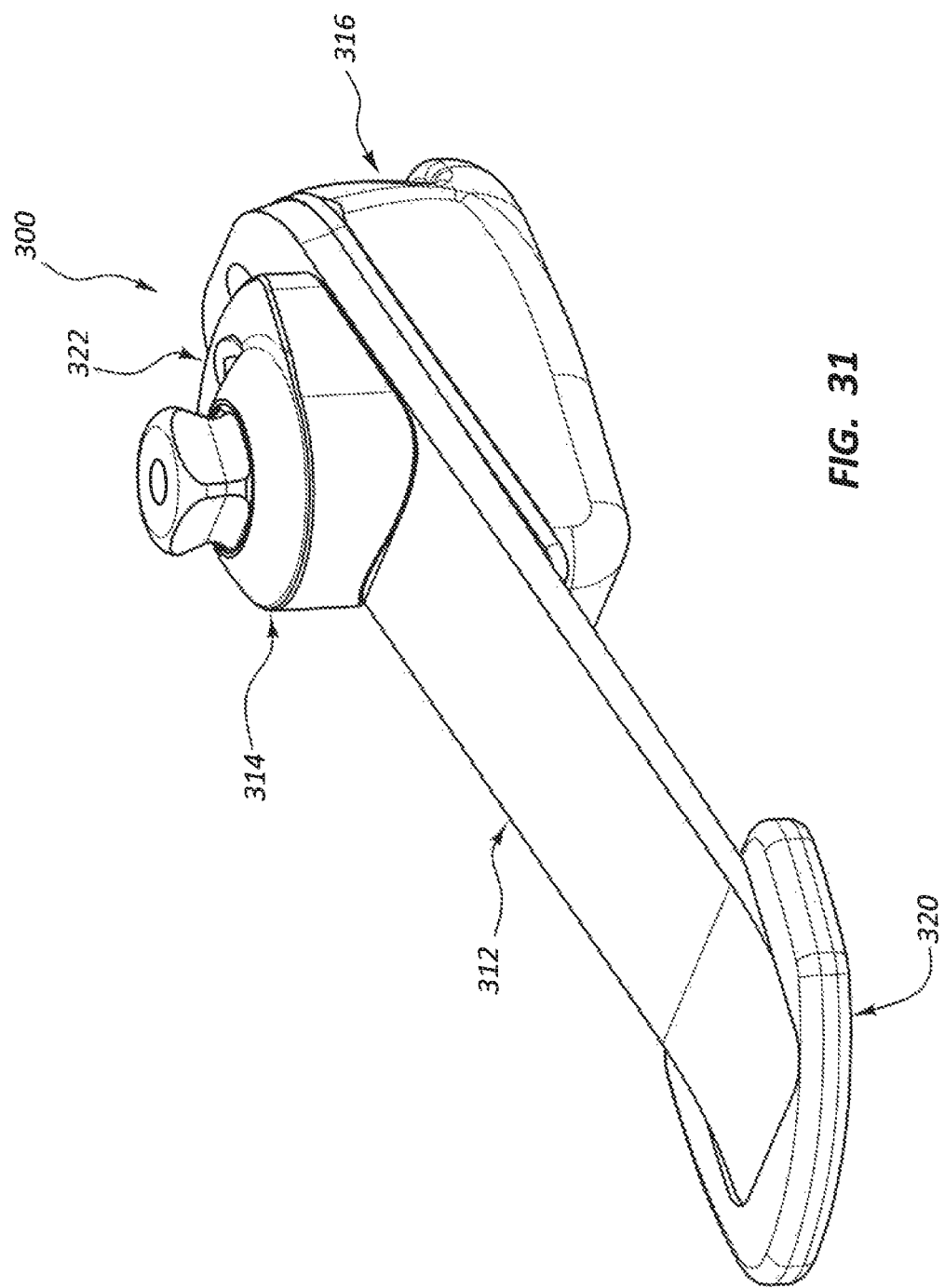
FIG. 31 is an isometric view of an example prosthetic foot in accordance with the present disclosure.
Figure 34:
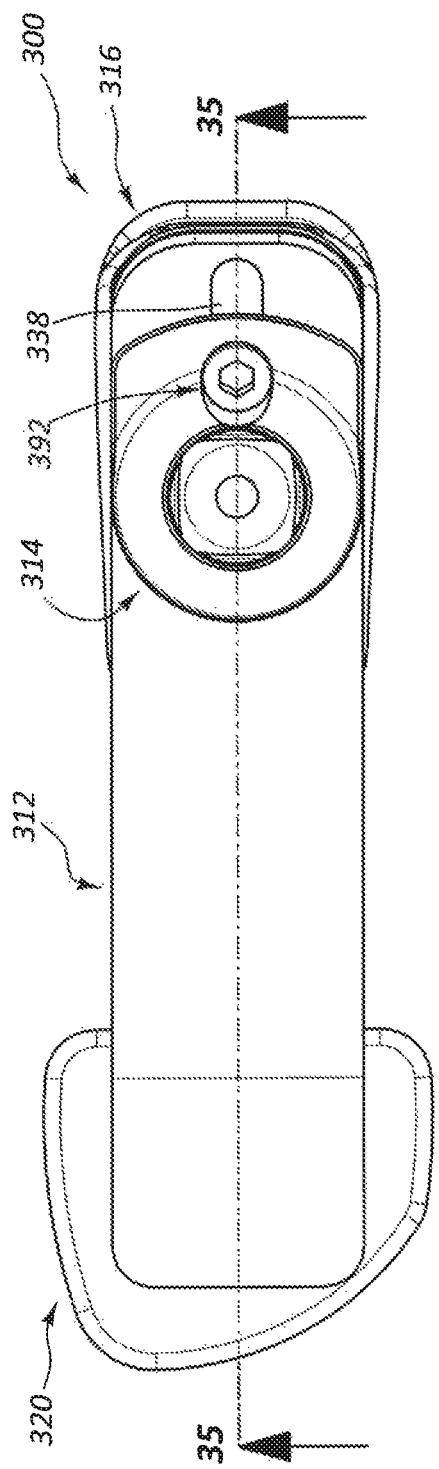
FIG. 34 is a top view of the prosthetic foot of FIG. 31.
Figure 35:
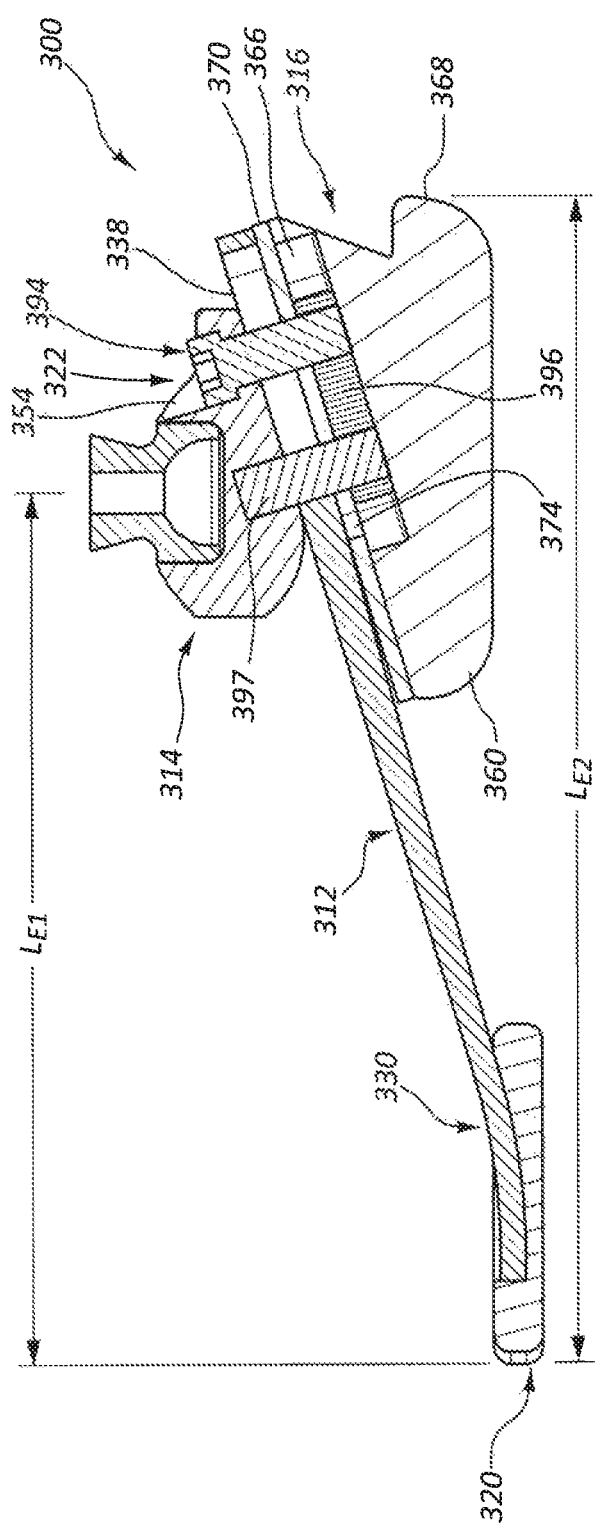
FIG. 35 is a cross-sectional view of the prosthetic foot shown in FIG. 34, taken along cross-section indicators 35-35.
Figure 36:
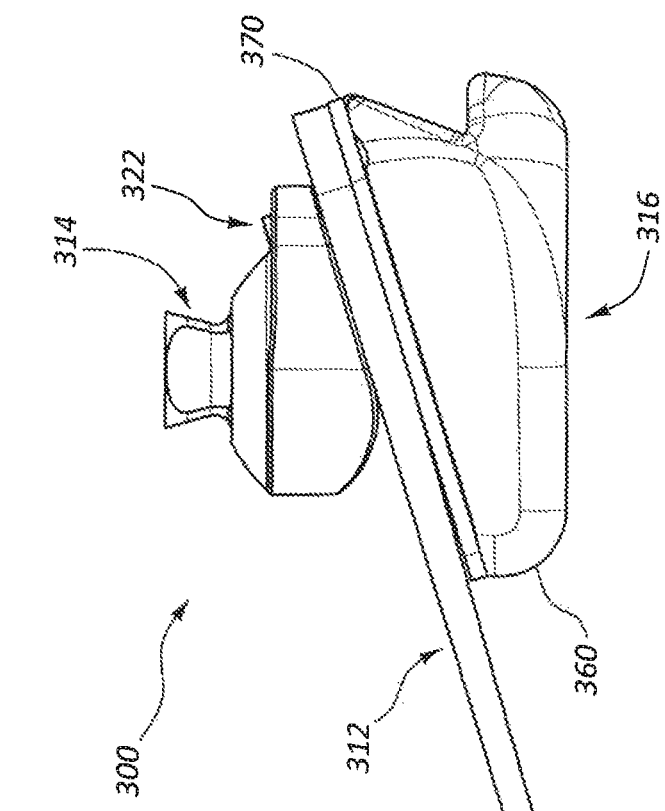
FIG. 36 is a left side view of the prosthetic foot of FIG. 31.
Figure 37:
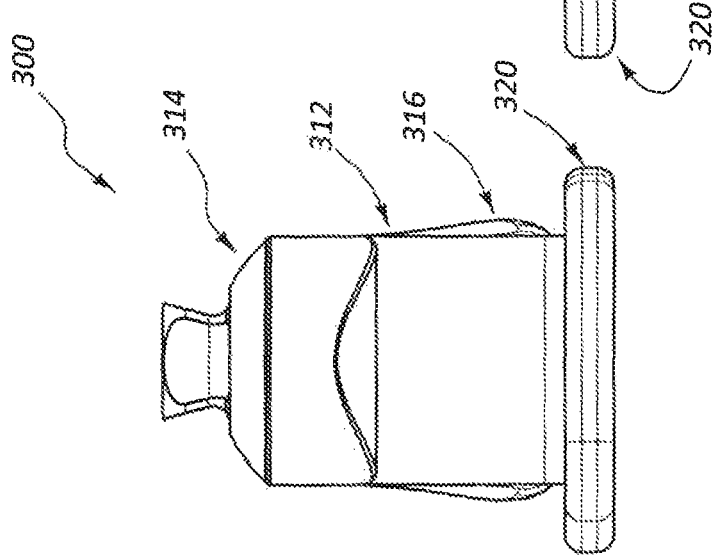
FIG. 37 is a front view of the prosthetic foot of FIG. 31.
Figure 40:
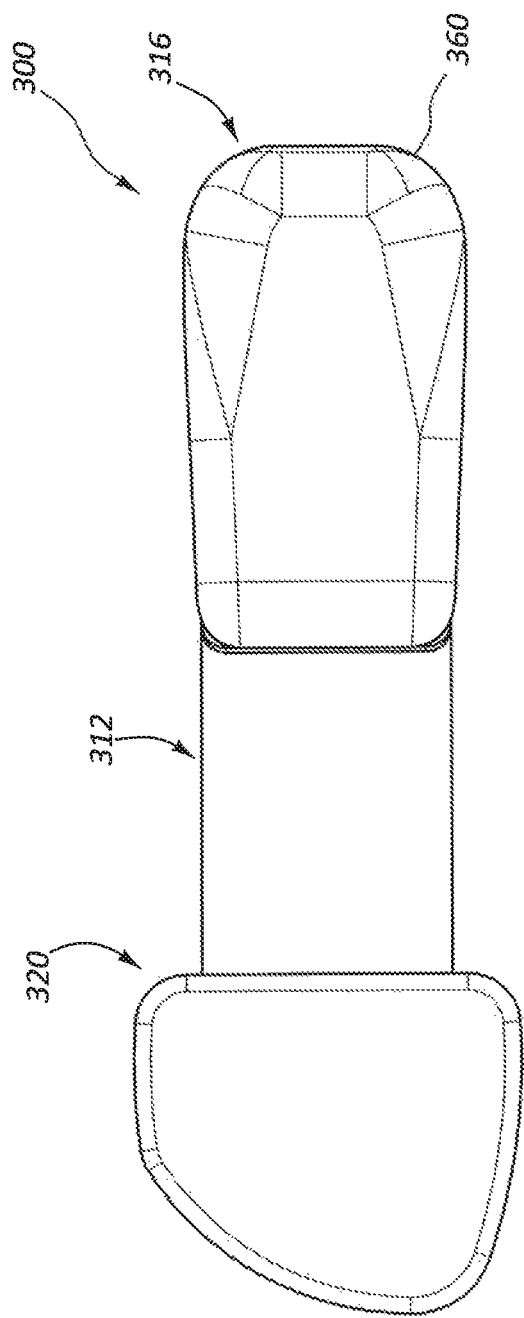
FIG. 40 is a bottom view of the prosthetic foot of FIG. 31.
Figure 41:
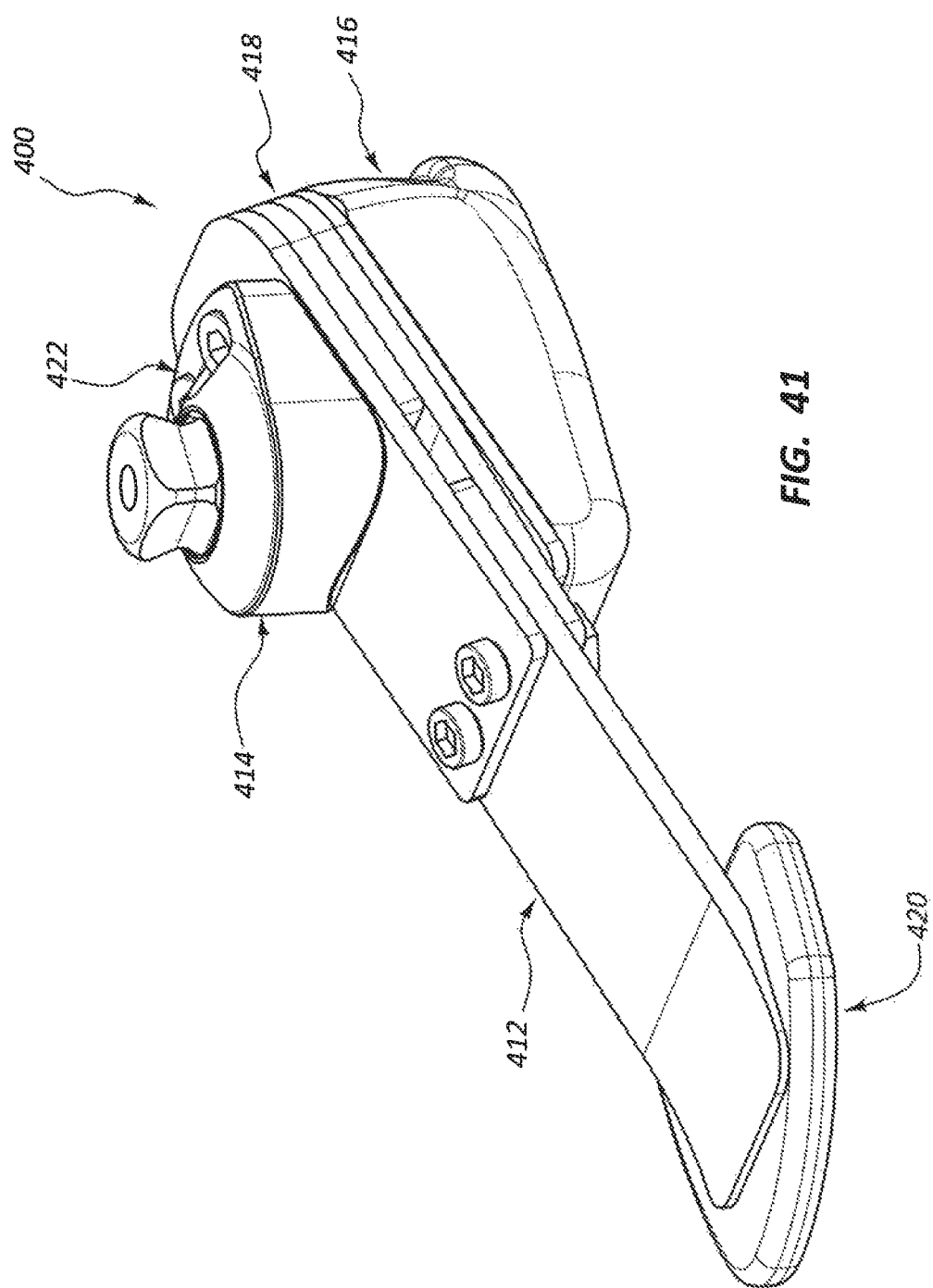
FIG. 41 is an isometric view of an example prosthetic foot in accordance with the present disclosure.
Figure 44:
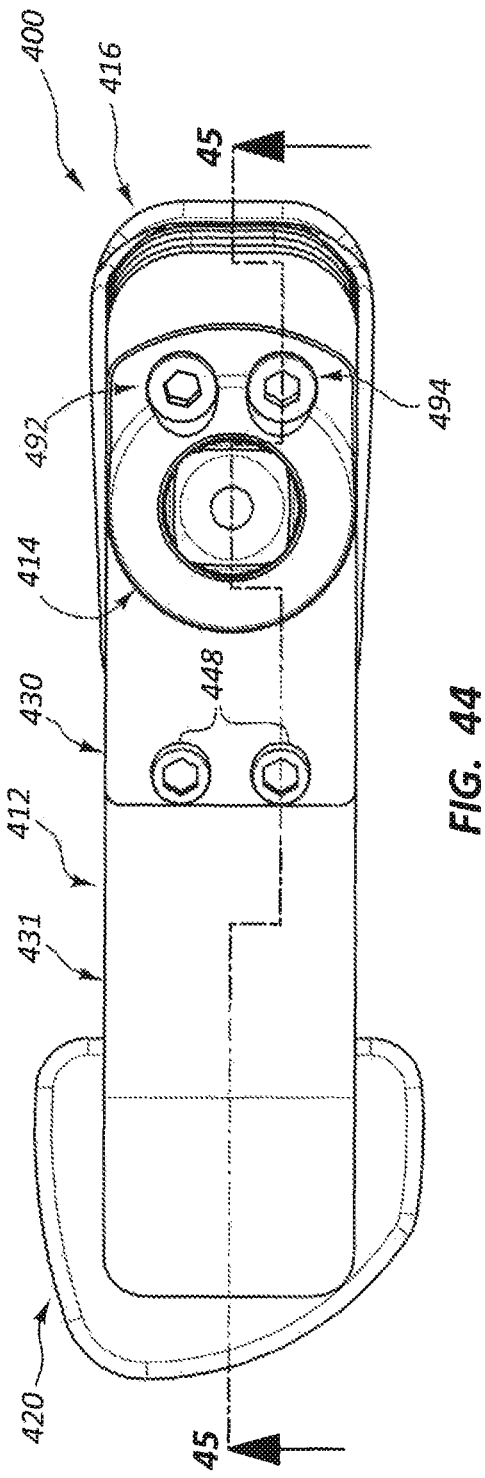
FIG. 44 is a top view of the prosthetic foot of FIG. 41.
Figure 45:
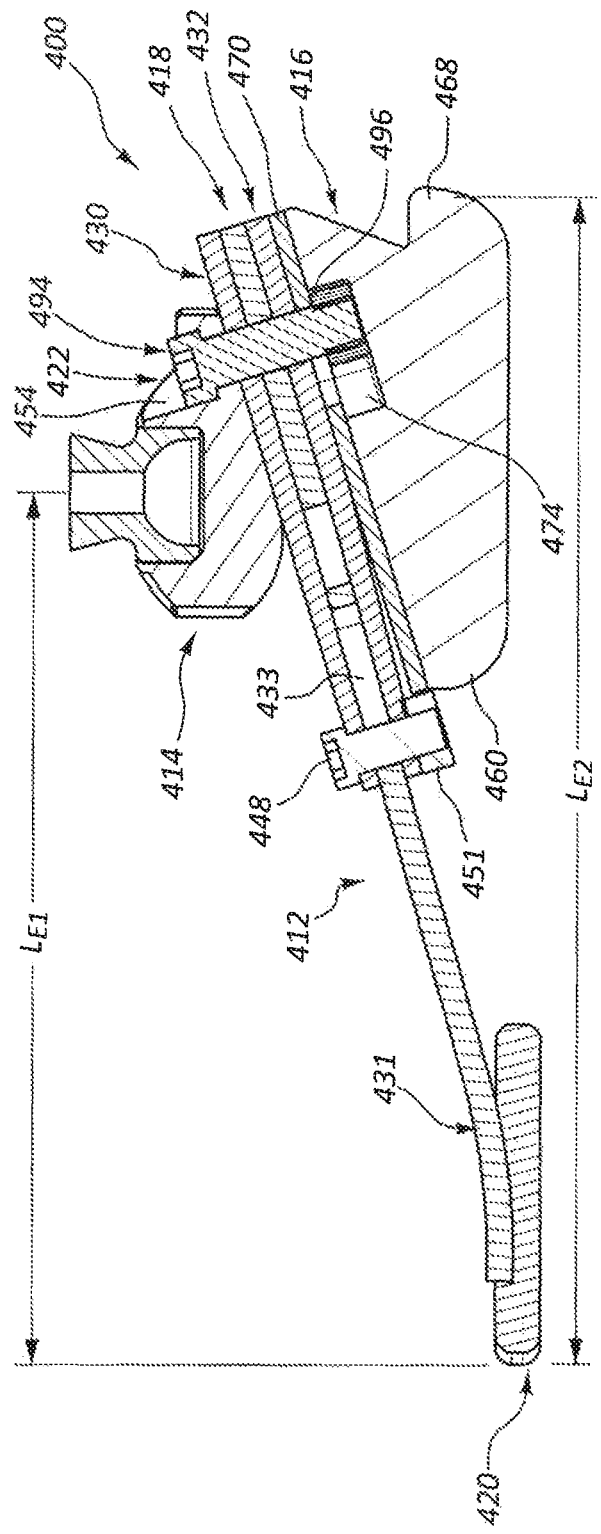
FIG. 45 is a cross-sectional view of the prosthetic foot shown in FIG. 44, taken along cross-section indicators 45-45.
Figures 48, 49:
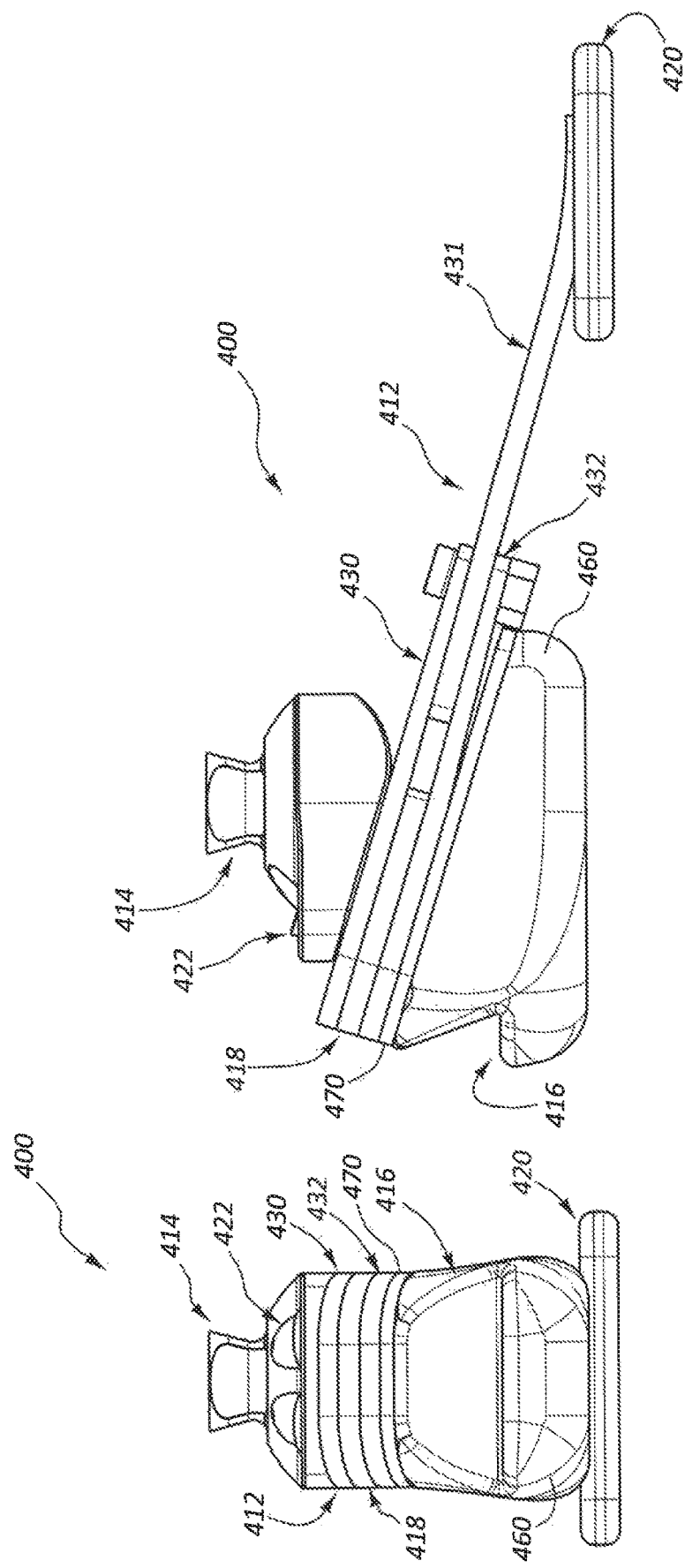
FIG. 48 is a right side view of the prosthetic foot of FIG. 41.
FIG. 49 is a rear view of the prosthetic foot of FIG. 41.
Figure 50:
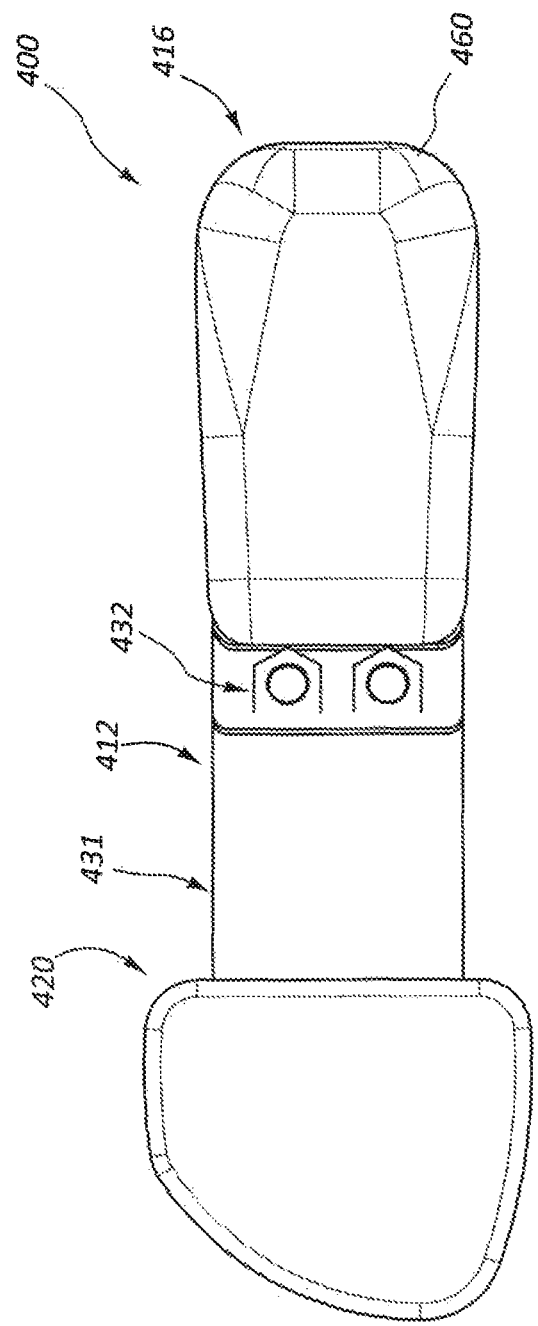
FIG. 50 is a bottom view of the prosthetic foot of FIG. 41.
Figure 51:
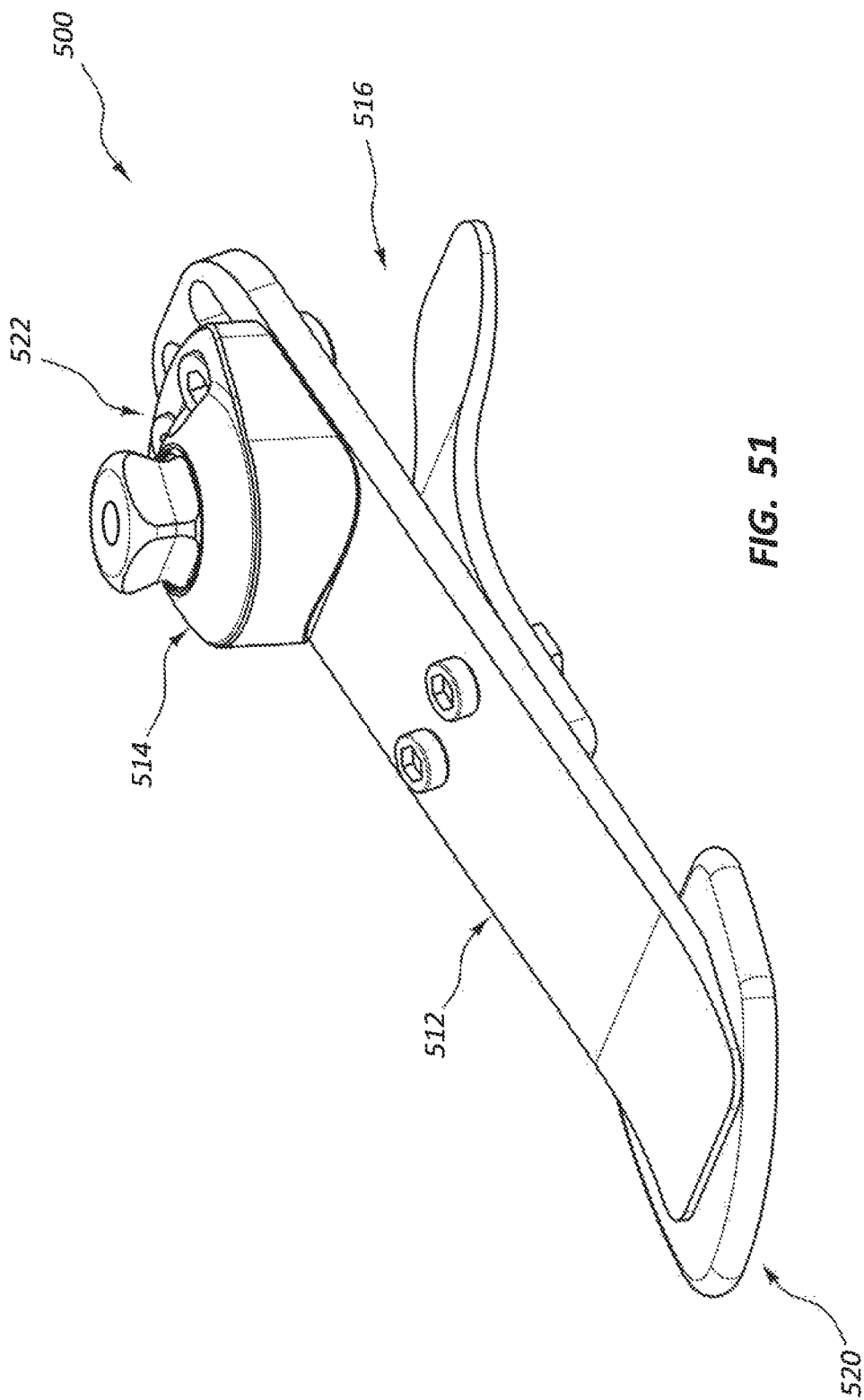
FIG. 51 is an isometric view of an example prosthetic foot in accordance with the present disclosure.
Figure 56:
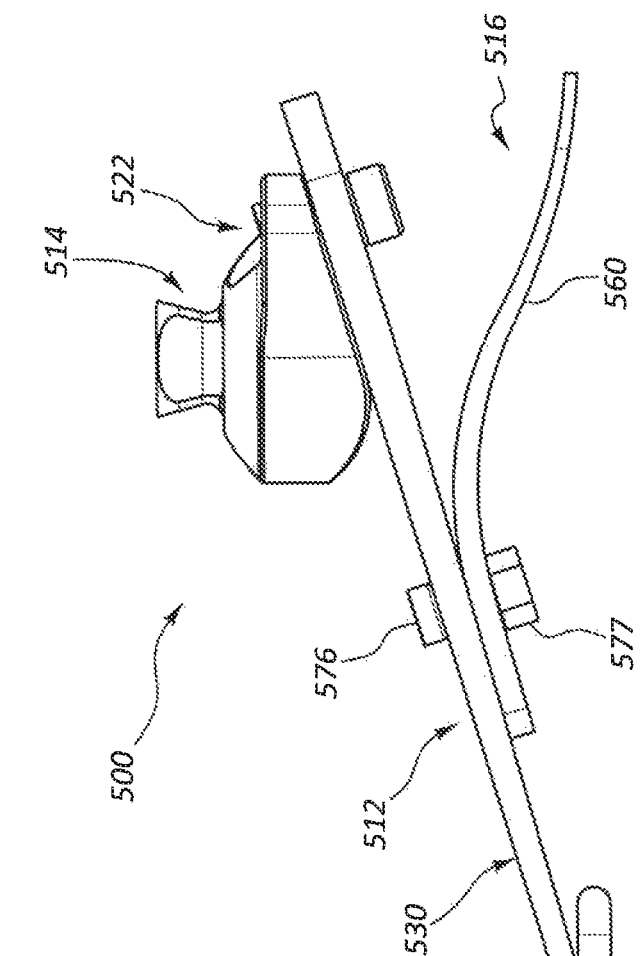
FIG. 56 is a left side view of the prosthetic foot of FIG. 51.
Figure 57:
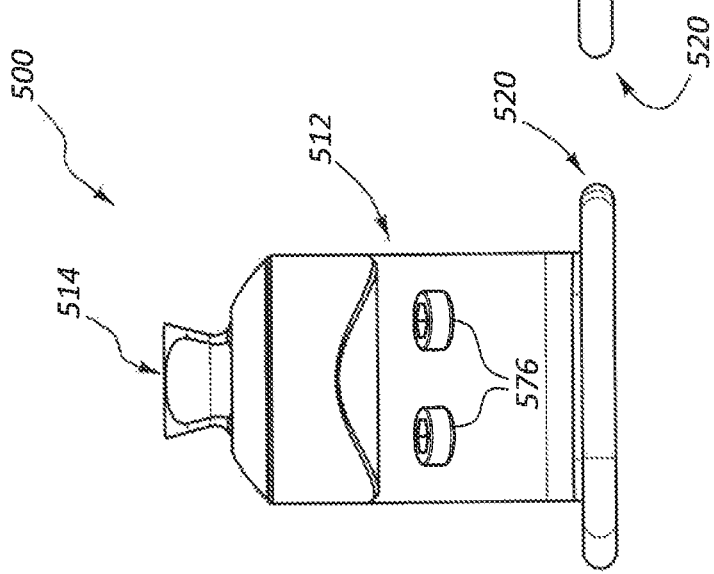
FIG. 57 is a front view of the prosthetic foot of FIG. 51.
Figure 60:
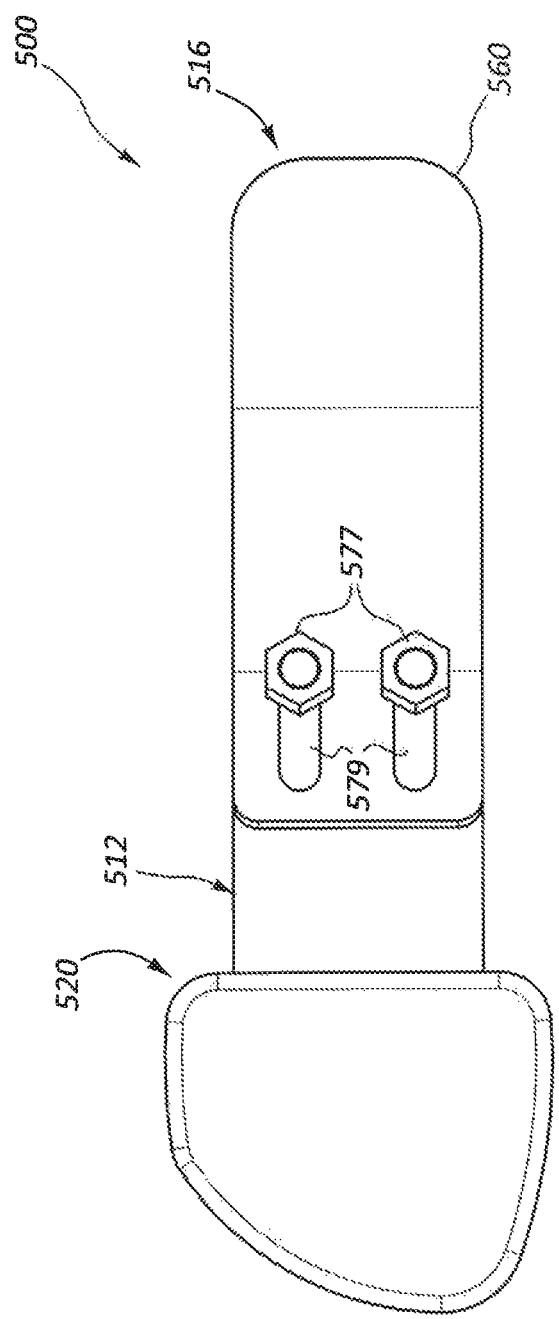
FIG. 60 is a bottom view of the prosthetic foot of FIG. 51.
Figure 61:
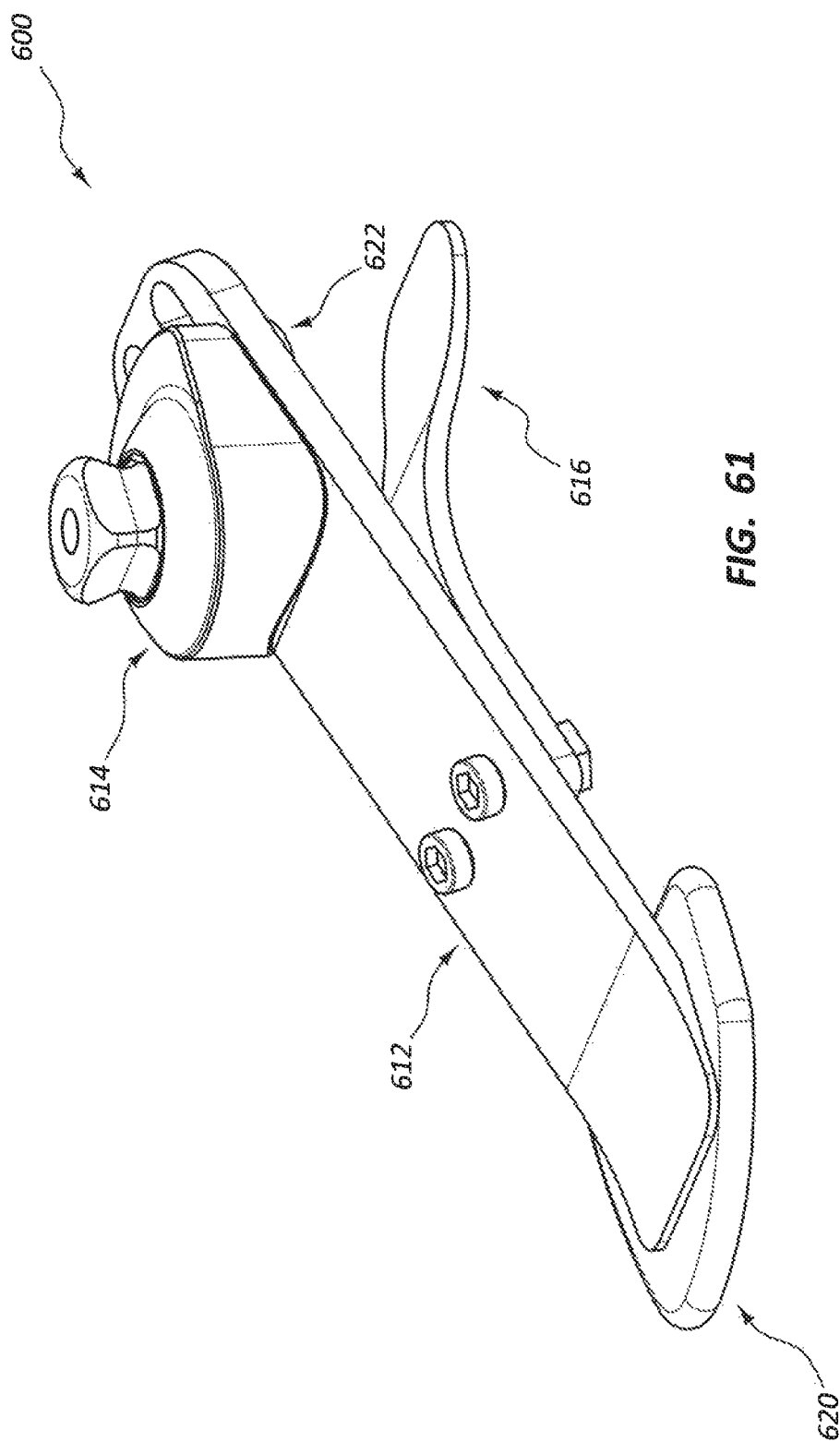
FIG. 61 is an isometric view of an example prosthetic foot in accordance with the present disclosure.

The first and second spring elements 30, 32 are shown having substantially the same length $L_1$ (see FIG. 5).

The first and second spring elements 30, 32 may be fixed together at the bond region 42, which is positioned at the toe end portion 34. The bond region 42 may comprise, for example, an adhesive. Other types of connections may be used to fix the toe end portion 34 first and second spring elements 30, 32 together at toe region 34. In some examples, the bond region 42 may be defined using, for example, one or more fasteners, clips, brackets, welding, heat bonding, co-molding, etc. The toe end portion 34 of the first and second spring elements 30, 32 are connected to the toe pad 20. Toe pad 20 may include a channel 90 receptive of the toe end portion 34 of the first and second spring elements 30, 32. Toe pad 20 may provide additional stability and weight distribution during use of prosthetic foot 10.

The first and second spring elements 30, 32 may comprise a fiber reinforced material. The first and second spring elements 30, 32 may be spaced apart along their length from the toe end portion 34 towards the heel end portion 36. Spacer 18 may be interposed between the first and second spring elements 30, 32 to maintain the spaced apart arrangement of the first and second spring elements 30, 32 at locations posterior of toe end portion 34.

The first and second slots 38, 40 are positioned at the heel end portion 36 and extend from the top surface 44 to the bottom surface 46 of each of the first and second spring elements 30, 32. The first and second slots 38, 40 are arranged longitudinally and in parallel with a longitudinal axis of the prosthetic foot 10. The first and second slots 38, 40 may have any desired length $L_4$. In one example, the length $L_4$ is in the range of about 0.2 centimeters to about 10 centimeters, and more particularly in the range of about 1 centimeter to about 3 centimeters. In one example, the length $L_4$ is about 2 centimeters. The first and second slots 38, 40 may also have a width $W_1$. Typically, the width $W_1$ is about the same as the diameter of the structure extending through the first and second slots 38, 40, as described in further detail below. In one example, width $W_1$ is in the range of about 0.1 centimeters to about 1 centimeter, and more particularly in the range of about 0.1 centimeters to about 0.5 centimeters. The width and length dimensions of any aperture and/or slot shown and described with reference to FIGS. 1-71 may have the dimensions of length $L_1$ and width $W_1$, or other dimensions to accommodate whatever sized or shaped fasteners, alignment rods, or other connection features that are used for a particular embodiment.

The attachment member 14 comprises a connector 50, a bottom surface 52, and a pair of apertures 54. The connector 50 comprises a male connector feature. The connector 50 may comprise a male pyramid comprised of an industry standard dome and pyramid configuration. In at least some examples, connector 50 provides for alignment changes between about 10° to about 20° in an anterior/posterior direction and about 10° to about 20° in a medial/lateral direction.

The attachment member 14 may be oriented with the bottom surface 52 facing the top surface 44 for spring element 30. The apertures 54 are aligned with the first and second slots 38, 40. The apertures 54 are typically sized to receive fasteners of the connection assembly 22 as fully described above. Typically, the apertures 54 have a diameter that is substantially the same as the width $W_1$ of the first and second slots 38, 40. The attachment member 14 typically has a shape for bottom surface 52 that arranges the connector 50 substantially vertically when attachment member 14 is positioned along top surface 44 of spring member 30, as shown in at least FIG. 5.

Heel assembly 16 includes a first member 60 having top and bottom surfaces 62, 64. A nut recess 66 may be formed on top surface 62. A posterior edge 68 may be positioned along the bottom surface 64. In at least some arrangements, posterior edge 68 defines a posterior-most point for purposes of defining the effective length $L_{E2}$.

In at least some arrangements, the first member 60 comprises a foam material or other relatively elastic material. First member 60 may comprise other materials and have other constructions in other embodiments. Although first member 60 comprises a substantially solid construction with exception of the nut recess 66, other embodiments may include a plate-like structure having spring properties.

Heel assembly 16 may also include a mounting plate 70 having first and second slots 72, 74 formed therein. Mounting plate 70 may be positioned along top surface 62 of first member 60. Mounting plate 70 may, in at least some embodiments, be permanently fixed to top surface 62 using, for example, adhesives or other bonding agents, welding, fasteners, or the like. The first and second slots 72, 74 may have a similar size and shape as the first and second slots 38, 40 of the first and second spring elements 30, 32. In other arrangements, the first and second slots 72, 74 may have a shape and size similar to the apertures 54 of the attachment member 14. In still further embodiments, the apertures 54 of attachment member 14 may have a shape and size similar to the first and second slots 72, 74. The shape and size of apertures 54 and first and second slots 72, 74 may influence adjustability of the attachment member 14 and heel assembly 16 relative to the spring assembly 12, and to each other.

The mounting plate 70 may comprise a fiber reinforced material. In other examples, mounting plate 70 may comprise a metal material. In at least some examples, the first and second slots 72, 74 may be threaded and sized to threadably receive a threaded fastener such as a threaded bolt. The shape and size of mounting plate 70 may influence a stiffness property of spring assembly 12. For example, moving the mounting plate 70 in an anterior direction may increase a stiffness property of spring assembly 12 as compared to moving mounting plate 70 in a posterior direction relative to spring assembly 12.

Spacer 18 may include a plate-like structure having first and second slots 80, 82 and a length $L_2$. The first and second slots 80, 82 may have a size and shape comparable to the size and shape of first and second slots 38, 40 and/or first and second slots 72, 74. The first and second slots 80, 82 are typically aligned with the first and second slots 38, 40 and first and second slots 72, 74, and arranged for receiving a structure such as a fastener extending there through. Spacer 18 may be replaced with spacers of different lengths. Spacers 18 of different lengths may influence a stiffness property of spring assembly 12. Typically, adjusting prosthetic foot 10 to have a greater effective length will decrease a stiffness property of spring assembly 12. Replacing spacer 18 with a similar spacer of different length $L_2$ will typically increase the stiffness property of spring assembly 12 to counteract the reduced stiffness provided by increasing at least one of the effective lengths $L_{E1}$, $L_{E2}$. In some embodiments, spacer 18 is movable axially along the length of spring assembly 12, which may also increase or decrease the stiffness property of spring assembly 12. First and second slots 80, 82 may permit some longitudinal movement of spacer 18 relative to spring assembly 12 to provide such adjustments in stiffness in spring assembly 12. In some examples, first and second slots 80, 82 have a greater length than the length $L_4$ of first and second slots 38, 40 to permit increased range of motion in a longitudinal direction relative to spring assembly 12.

Connection assembly 22 includes first and second fasteners 92, 94 and at least one nut 96. The first and second fasteners 92, 94 each include a head 98 and a shank 99. The shank 99 extends through the apertures 54, the first and second slots 38, 40, the first and second slots 80, 82, and the first and second slots 72, 74, and into threaded engagement with nut 96. In other embodiments, the fasteners 92, 94 may threadably connect to mounting plate 70 rather than to nut 96. Tightening the connection assembly 22 fixes a longitudinal position of the attachment member 14 and heel assembly 16 relative to spring assembly 12. The longitudinal arrangement of the first and second slots 72, 74 of heel assembly 16 may permit some relative longitudinal movement of heel assembly 16 compared to attachment member 14 for any given longitudinal position of attachment member 14. In at least some arrangements, connection assembly 22 fixes the attachment member 14 and heel assembly 16 to each other so that they move in tandem longitudinally relative to spring assembly 12.

The nut recess 66 formed in heel assembly 16 may be sized to receive nut 96. Nut recess 66 may be sized and shaped to permit at least some longitudinal movement of nut 96 relative to heel assembly 16.

Heads 98 of first and second fasteners 92, 94 may be sized to receive a tool such as, for example, an Allen wrench, a screwdriver, or the like. Heads 98 typically have a size greater than a size of apertures 54. In other embodiments, first and second fasteners 92, 94 may extend through prosthetic foot 10 in an opposite direction (e.g., from heel assembly 16 toward attachment member 14 with nut 96 positioned at attachment member 14).

In operation, attachment member 14 and heel assembly 16 may be fixed in a given longitudinal direction relative to spring assembly 12 by tightening first and second fasteners 92, 94 of connection assembly 22. If the effective length $L_{E1}$, $L_{E2}$ of prosthetic foot 10 needs to be increased (e.g., when the amputee grows taller), connection assembly 22 may be loosened, and at least one of attachment member 14 and heel assembly 16 may be moved in a posterior direction relative to spring assembly 12 by moving first and second fasteners 92, 94 within slots 38, 40; 72, 74; and 80, 82. Thereafter, the connection assembly 22 is tightened to fix the attachment member 14 and heel assembly 16 in the new longitudinally adjusted position relative to spring assembly 12. As discussed above, spacer 18 may also be adjusted longitudinally to increase or decrease the stiffness of spring assembly 12 to offset changes in effective length $L_{E1}$, $L_{E2}$. In some arrangements, spacer 18 may be replaced with a spacer of different length in order to provide the desired change in stiffness of spring assembly 12. Spacers 18 of different widths, thicknesses, and/or materials may also be used to adjust or modify other properties of prosthetic foot 10 such as, for example, stability.

Referring now to FIGS. 11-20, another example prosthetic foot 100 is shown and described. Prosthetic foot 100 includes a single spring element 130, and as such does not include a spacer to adjust for changes in stiffness as the effective length $L_{E1}$, $L_{E2}$ is changed. Prosthetic foot 100 includes a spring assembly 112, an attachment member 114, a heel assembly 116, a toe pad 120, and a connection assembly 122.

Referring primarily to FIGS. 12 and 13, spring assembly 112 includes a spring element 130, a toe end portion 134, a heel end portion 136, first and second slots 138, 140, top and bottom surfaces 144, 146, and a length $L_1$. Attachment member 114 includes a connector 150, a bottom surface 152, and apertures 154. Heel assembly 116 includes a spring member 160 having top and bottom surfaces 162, 164, and a posterior edge 168. Heel assembly 116 also includes a mounting plate 170 having first and second slots 172, 174. Posterior edge 168 of spring member 160 may be used to define the effective length $L_{E2}$.

Toe pad 120 may include a channel 190 receptive of the toe end portion 134 of spring element 130. Toe pad 120 may define an anterior-most portion of prosthetic foot 10 for the purposes of defining effective lengths $L_{E1}$, $L_{E2}$. Connection assembly 122 includes first and second fasteners 192, 194 and a nut 196. First and second fasteners 192, 194 each include a head 198 and a shank 199, wherein the shanks 199 extend through the apertures 154, first and second slots 138, 140, and first and second slots 172, 174, and into threaded engagement with nut 196.

In operation, at least one of the effective lengths $L_{E1}$, $L_{E2}$ of prosthetic foot 100 may be adjusted by loosening connection assembly 122, sliding at least one of attachment member 114 and heel assembly 116 relative to spring assembly 112, and retightening connection assembly 122. As discussed above, the first and second slots 172, 174 of heel assembly 116 may be replaced with circular apertures similar in size and shape to the apertures 54 of attachment member 14. In this arrangement, the attachment member 114 and heel assembly 116 would move in tandem longitudinally relative to spring assembly 112 as first and second fasteners 192, 194 move longitudinally within first and second slots 138, 140. In other arrangements, apertures 154 of attachment member 114 are formed as elongate slots, for example, similar in size and shape to first and second slots 172, 174. This construction for apertures 154 may permit additional longitudinal movement of attachment member 114 and heel assembly 116 relative to each other and to spring assembly 112.

FIGS. 21-30 illustrate another example prosthetic foot 200. Prosthetic foot 200 includes a spring assembly 212, an attachment member 214, a heel assembly 216, a toe pad 220, and a connection assembly 222. The prosthetic foot 200 may be referred to as a single toe spring prosthetic foot. The heel assembly 216 may be referred to as a heel spring assembly for a foot prosthesis.

Referring primarily to FIGS. 22 and 23, spring assembly 212 may include a spring element 230, having a toe end portion 234 and a heel end portion 236. First spring element 230 has first and second slots 238, 240 therein, having a length $L_4$ as shown in FIG. 23. Spring element 230 also includes top and bottom surfaces 244, 246, and has a length $L_1$. Attachment member 214 includes a connector 250, a bottom surface 252 arranged facing the top surface 244 of spring element 230, and apertures 254.

Heel assembly 216 includes a spring member 260 having top and bottom surfaces 262, 264 and a posterior edge 268. Heel assembly 216 also includes a mounting plate 270 having first and second slots 272, 274, each having a length $L_3$. The spring member 260 and mounting plate 270 are connected to each other with fasteners 276 that extend through joint apertures formed in mounting plate 270 and joint apertures 279 formed in spring member 260. Fasteners 276 may threadably engage with nuts 277. Toe pad 220 includes a channel 290 that receives the toe end portion 234 of spring element 230.

Connection assembly 222 includes first and second fasteners 292, 294 that threadably mate with a nut 296. Each fastener 292, 294 includes a head 298 and shank 299.

Fasteners 292, 294 extend through apertures 254, attachment member 214, slots 238, 240 of spring element 230, and slots 272, 274 of mounting plate 270, and into threaded engagement with nut 296.

Referring to FIG. 25, at least one of the effective lengths $L_{E1}$, $L_{E2}$ of prosthetic foot 200 may be adjusted by longitudinally moving fasteners 292, 294 within slots 238, 240 and slots 272, 274. The position of attachment member 214 may be adjusted at least partially in a longitudinal direction independent of longitudinal movement of heel assembly 216. The at least partial independent longitudinal movement of the attachment member 214 relative to heel assembly 216 may be provided at least in part by the slots 272, 274 formed in mounting plate 270. In other arrangements, slots 272, 274 are replaced with apertures that limit relative longitudinal movement between attachment members 214 and heel assembly 216 and that result in concurrent longitudinal movement of attachment member 214 and heel assembly 216 relative to spring assembly 212.

Prosthetic foot 200 illustrates at least one heel spring assembly that may be used in place of the elastomeric (e.g., foam) heel assembly shown in FIGS. 1-20 for prosthetic feet 10, 100. Other types of heel spring assemblies are possible in place of the embodiment shown in FIGS. 21-30. At least some additional heel assembly embodiments are shown and described with reference to the remaining figures of the present application.

Referring now to FIGS. 31-40, another example prosthetic foot 300 is shown and described. Prosthetic foot 300 includes a spring assembly 312, an attachment member 314, a heel assembly 316, a toe pad 320, and a connection assembly 322. The spring assembly 312 includes a single spring element 330. Further, the connection assembly 322 includes a single fastener 392, as shown in at least FIGS. 32-35. Prosthetic foot 300 may include other alignment features (e.g., alignment post 397 shown in FIGS. 33 and 35) that help limit rotation and lateral movement between spring assembly 312 and attachment member 314 and heel assembly 316 while still providing the desired length adjustability for prosthetic foot 300.

Referring primarily to FIGS. 32 and 33, spring element 330 includes a toe end portion 334, a heel end portion 336, a single slot 338, top and bottom surfaces 344, 346, and a length $L_1$ (see FIG. 33). The attachment member 314 includes a connector 350, a bottom surface 352, and an aperture 354. Heel assembly 316 includes a spring member 360 having top and bottom surfaces 362, 364, a nut recess 366, and a posterior edge 368. A mounting plate 370 of heel assembly 316 includes a single slot 372 having a length $L_3$. Toe pad 320 includes a channel 390 receptive of the toe end portion 334 of spring element 330. Connection assembly 322 includes a single fastener 392 having a head 398 and shank 399.

In operation, prosthetic foot 300 is assembled by extending fastener 392 through aperture 354 of attachment member 314, slot 338 of spring element 330, and slot 372 of mounting plate 370, and into threaded engagement with nut 396. Alignment post 397 extends from attachment member 314, through slots 338, 372, and into engagement with nut 396. In at least some arrangements, the alignment post 397 does not threadably engage with nut 396 while still be connected to or at least partially retained by nut 396. Alignment post 397 may provide lateral and rotational stability between spring element 330 and the attachment member 314 and heel assembly 316. Loosening fastener 392 may permit relative longitudinal movement of at least one of attachment member 314 and heel assembly 316 relative to spring element 330 to adjust at least one of the effective lengths $L_{E1}$, $L_{E2}$ (see FIG. 35). Tightening fastener 392 fixes the adjusted effective length of the prosthetic foot 300.

Prosthetic foot 300 may be configured to permit at least some independent longitudinal movement of attachment member 314 and heel assembly 316 relative to spring assembly 312. The slot 372 formed in mounting plate 370 may permit such independent longitudinal movement. Replacing slot 372 with a pair of apertures (e.g., circular shaped apertures) sized to closely fit with fastener 392 and alignment post 397 may result in the attachment member 314 and heel assembly 316 being required to move in tandem (e.g., concurrently) in a longitudinal direction relative to spring assembly 312 as part of a length adjustment for prosthetic foot 300.

Other types of heel assembly configurations are possible in other embodiments that include the connection assembly features shown in FIGS. 31-40. For example, the heel spring embodiment of heel assembly 216 with reference to FIGS. 21-30 may be modified to include a single fastener and alignment post according to the connection assembly 322 shown in FIGS. 31-40.

FIGS. 41-50 illustrate another example prosthetic foot 400. Prosthetic foot 400 includes a plurality of toe spring elements that permit at least some length adjustability for prosthetic foot 400. Prosthetic foot 400 includes a spring assembly 412, an attachment member 414, a heel assembly 416, a spacer 418, a toe pad 420, and a connection assembly 422.

Referring primarily to FIGS. 42 and 43, spring assembly 412 includes a first spring element 430, a second spring element 432, and a third spring element 431. First and second spring elements 430, 432 include first and second posterior apertures 438, 440 and a pair of anterior apertures 449. First and second spring elements 430, 432 also define top and bottom surfaces 444, 446 and have a length $L_1$. Third spring element 431 includes a pair of slots of 433 positioned at a posterior end, has a toe end 434, and has a length $L_5$. Slots 433 have a length $L_6$. The slots 433 are aligned with the anterior apertures 449 when prosthetic foot 400 is assembled (see FIG. 45).

Attachment member 414 includes a connector 450, a bottom surface 452 that faces top surface 444 for spring element 430, and apertures 454. Heel assembly 416 includes a spring member 460 having top and bottom surfaces 462, 464, a nut recess 466, and a posterior edge 468. Heel assembly 416 also includes a mounting plate 470 having first and second slots 472, 474 that each have a length $L_3$. Spacer 418 includes first and second apertures 480, 482. Toe pad 420 includes a channel 490 receptive of a toe end portion of third spring element 431. Connection assembly 422 includes first and second fasteners 492, 494, each having a head 498 and shank 499. Connection assembly 422 also includes a nut 496 that threadably engages the first and second fasteners 492, 494.

When assembling prosthetic foot 400, the first and second fasteners 492, 494 extend through apertures 454 of attachment member 414, apertures 438, 440 of first and second spring elements 430, 432, and slots 472, 474 of mounting plate 470, and into threaded engagement with nut 496. Loosening first and second fasteners 492, 494 may permit at least some longitudinal movement of heel assembly 416 relative to spring assembly 412, which may adjust at least the effective length $L_{E2}$ of prosthetic foot 400.

Spring assembly 412 may be assembled by extending a pair of fasteners 448 through anterior apertures 449 of first and second spring elements 430, 432, and slots 433 of third spring element 431, and into threaded engagement with nuts 451. Loosening fasteners 448 may permit some relative longitudinal movement between third spring element 431 and the first and second spring elements 430, 432, which may alter at least one of the effective lengths $L_{E1}$ and $L_{E2}$ (see FIG. 45).

Prosthetic foot 400 provides multiple options for adjusting one of the effective lengths $L_{E1}$, $L_{E2}$ of prosthetic foot 400. A single feature is provided in prosthetic foot 400 for adjusting the effective length $L_{E1}$. Other embodiments may include additional or different features that permit additional ways to adjust effectively $L_{E1}$ such as, for example, providing slots in place of apertures 438, 440 in first and second spring elements 430, 432. Furthermore, in other embodiments the first and second spring elements 430, 432 are rearranged with the third spring element 431 such that the third spring element 431 extends to a posterior position on prosthetic foot 400 and first and second spring elements 430, 432 extend to an anterior portion of prosthetic foot 400 (e.g., connected with toe pad 420).

FIGS. 51-60 illustrate another example prosthetic foot 500. Prosthetic foot 500 includes a spring assembly 512 having a single spring element 530 (see FIGS. 52-55). Prosthetic foot 500 also includes an attachment member 514, a heel assembly 516, a toe pad 520, and a connection assembly 522. Heel assembly 516 is connected directly to spring assembly 512 at a location spaced between anterior and posterior ends of spring assembly 512. The connection point between heel assembly 516 and spring assembly 512 may provide the length adjustability features for prosthetic foot 500.

Referring primarily to FIGS. 52 and 53, the spring assembly 512 includes a first spring element 530 having toe and heel end portions 534, 536, first and second slots 538, 540, top and bottom surfaces 544, 546, a length $L_1$, and fastener apertures 578. Attachment member 514 includes a connector 550, a bottom surface 552 facing a top surface 544 of spring element of 530, and apertures 554. Heel assembly 516 includes a single spring member 560 having top and bottom surfaces 562, 564, a posterior edge 568, and fastener slots 579 each having a length $L_7$.

Toe pad 520 includes a channel 590 receptive of the toe end portion 534 of spring element 530. Connection assembly 522 includes first and second fasteners 592, 594, each having a head 598 and shank 599. Connection assembly 522 also includes a nut 596 that threadably engages with the first and second fasteners 592, 594.

Prosthetic foot 500 is assembled by extending the first and second fasteners 592, 594 through apertures 554 of attachment member 514, and slots 538, 540 of spring member 530, and into threaded engagement with nut 596. Heel assembly 516 is connected to spring assembly 512 by extending a pair of fasteners 576 through fastener apertures 578 of spring element 530, and slots 579 of heel spring member 560, and into threaded engagement with nuts 577.

The effective length $L_{E1}$ (see FIG. 55) may be adjusted by loosening fasteners 592, 594, sliding attachment member 514 longitudinally relative to spring assembly 512, and then tightening fasteners 592, 594 to maintain the adjusted effective length $L_{E1}$. Effective length $L_{E2}$ may be adjusted by loosening fasteners 576, sliding heel assembly 516 longitudinally relative to spring assembly 512, and then tightening fasteners 576 to maintain the adjusted effective length $L_{E2}$. In other embodiments, either one of the attachment member 514 and heel assembly 516 may have a fixed position relative to spring assembly 512 by changing the slots 538, 540 to circular apertures (e.g., to eliminate longitudinal movement of attachment member 514 relative to spring assembly 512) or change slots 579 to circular apertures (e.g., to eliminate longitudinal movement of heel assembly 516 relative to spring assembly 512).

Other types of heel assembly embodiments may be possible in place of the specific embodiments shown in FIGS. 51-60 while still taking advantage of the connection assembly provided by fasteners 576 and apertures 578, 579. Furthermore, the pairs of fasteners 592, 594 and 576 may be replaced with other types of fasteners or connection features including, for example, the single fastener and alignment post of prosthetic foot 300 described above.

FIGS. 61-65 show an alternative arrangement for connection of the attachment member to the spring member of a prosthetic foot. FIGS. 61-65 show a prosthetic foot 600 having a spring assembly 612, attachment member 614, heel assembly 616, toe pad 620, and connection assembly 622.

Figure 62:
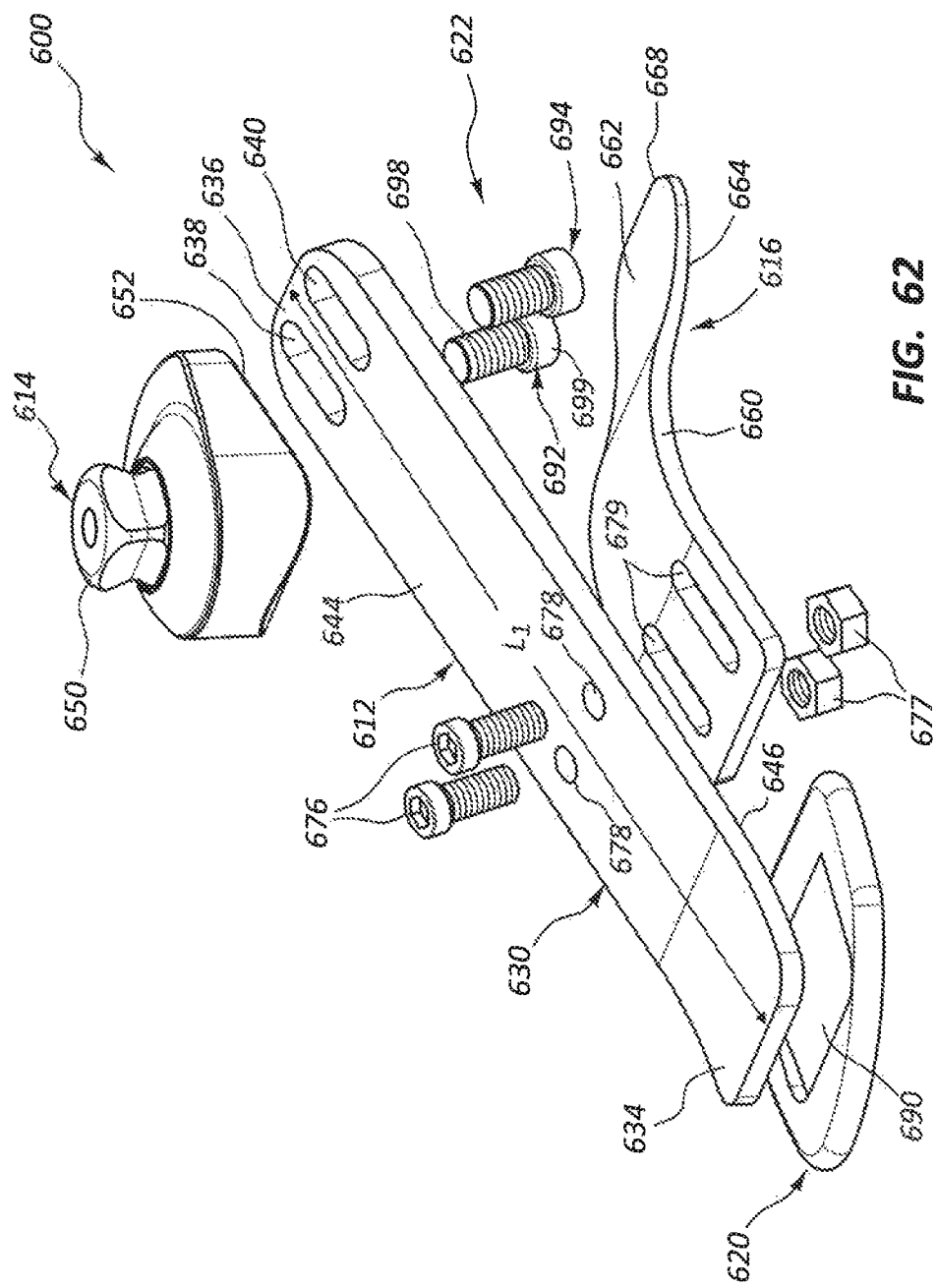
FIG. 62 is an exploded isometric view of the prosthetic foot of FIG. 61.
Figure 65:
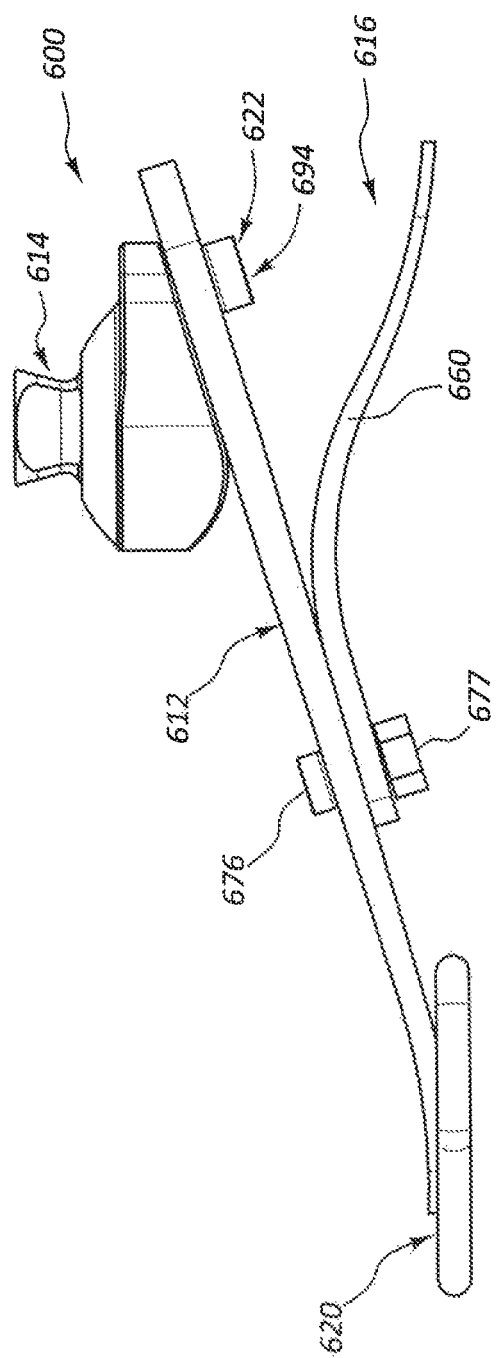
FIG. 65 is a left side view of the prosthetic foot of FIG. 61.
Figure 66:
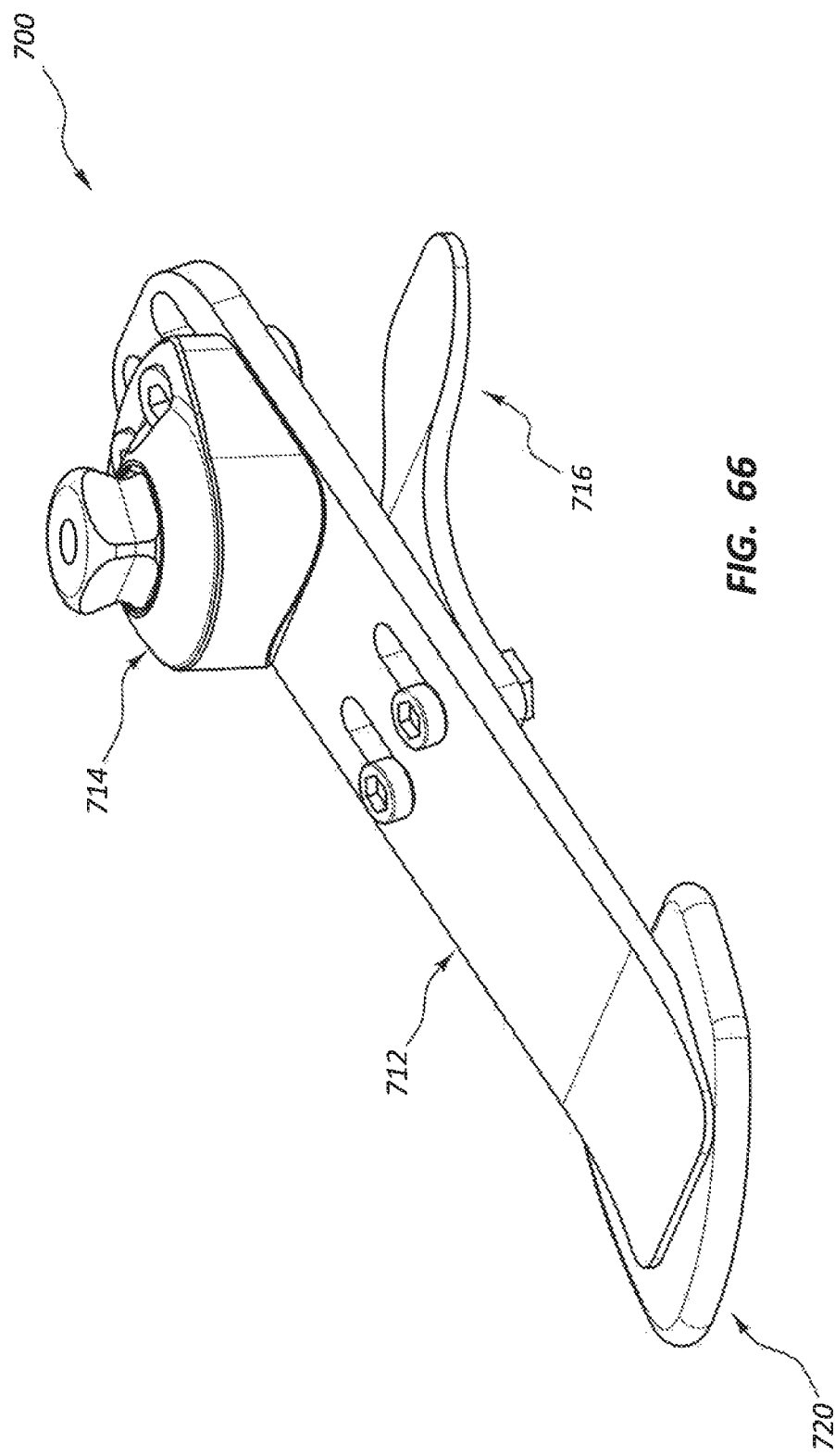
FIG. 66 is an isometric view of an example prosthetic foot in accordance with the present disclosure.

Referring primarily to FIG. 62, spring assembly 612 includes a spring element 630 having toe and heel end portions 634, 636, first and second slots 638, 640, top and bottom surfaces 644, 646, and a length $L_1$. Spring element 630 also includes a pair of apertures 678 positioned at a location spaced between the toe and heel end portions 634, 636.

Attachment member 614 includes a connector 650, a bottom surface 652, and a pair of apertures 654 formed in and accessible along bottom surface 652 (see FIG. 64). Heel assembly 616 includes a spring member 660 having top and bottom surfaces 662, 664, a posterior edge 668, and a pair of slots 679 that align with aperture 678 of spring element 630. Toe pad 620 includes a channel 690 receptive of the toe end portion 634 of spring element 630. Connection assembly 622 includes first and second fasteners 692, 694, each having a head 699 and shank 698. First and second fasteners 692, 694 threadably engage attachment member 614 to provide tightening and securement of attachment member 614 to springe assembly 612 without the use of a separate nut feature. In other embodiments, fasteners 692, 694 may threadably engage at least one nut positioned in or on attachment member 614. First and second fasteners 692, 694 may extend through slots 638, 640, through the bottom surface 646 of spring element 630, and into threaded engagement with apertures 654.

The effective length $L_{E1}$ of prosthetic foot 600 may be adjusted by loosening fasteners 692, 694 and moving attachment member 614 longitudinally relative to spring assembly 612. Effective length $L_{E2}$ may be adjusted by loosening fasteners 676, which extend through apertures 678 and slots 679 and into threaded engagement with nut 677. With fasteners 676 loosened, heel assembly 616 may be adjusted longitudinally relative to spring element 630 to adjust effective length $L_{E2}$. Tightening fasteners 676 fixes the adjusted effective length $L_{E2}$.

The arrangement of fasteners, slots, nuts, and threaded bores shown with reference to FIGS. 61-65 are just some examples of the many different ways in which the attachment member 614 and heel assembly 616 may be attached or otherwise mounted to spring assembly 612. The attachment features shown in FIGS. 61-65 may mount attachment member 614 and heel assembly 616 to spring assembly 612 while concurrently providing longitudinal adjustment of those features relative to spring assembly 612 to alter an effective length feature of prosthetic foot 600.

Referring now to FIGS. 66-70, another example prosthetic foot 700 is shown including many of the same or similar features to the prosthetic foot 500 shown and described with reference to FIGS. 51-60. Prosthetic foot 700 may have at least some features that are reversed in position as compared to prosthetic foot 500 for providing the longitudinal adjustment of the heel assembly relative to the spring assembly.

Figure 67:
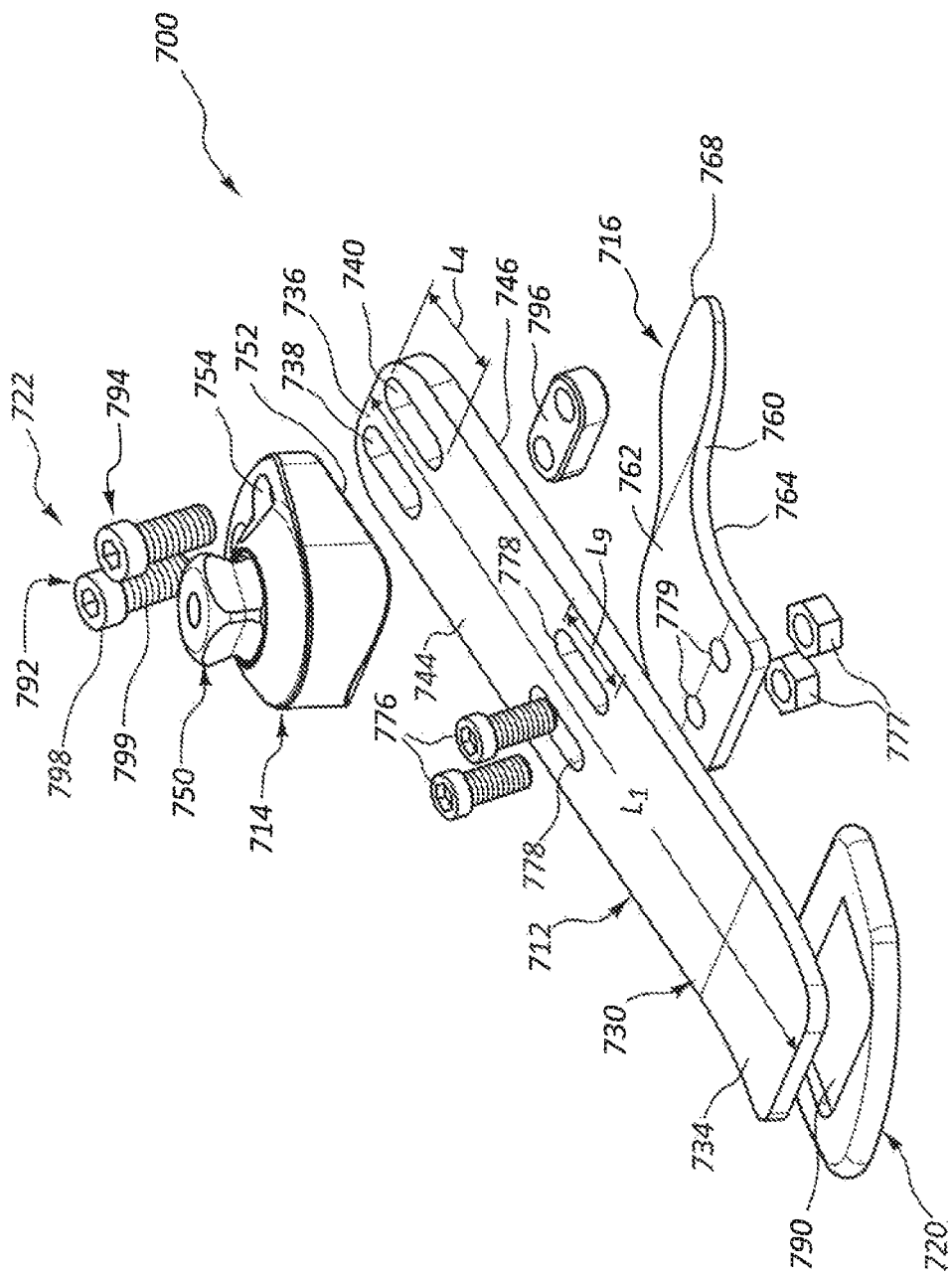
FIG. 67 is an exploded isometric view of the prosthetic foot of FIG. 66.
Figure 70:
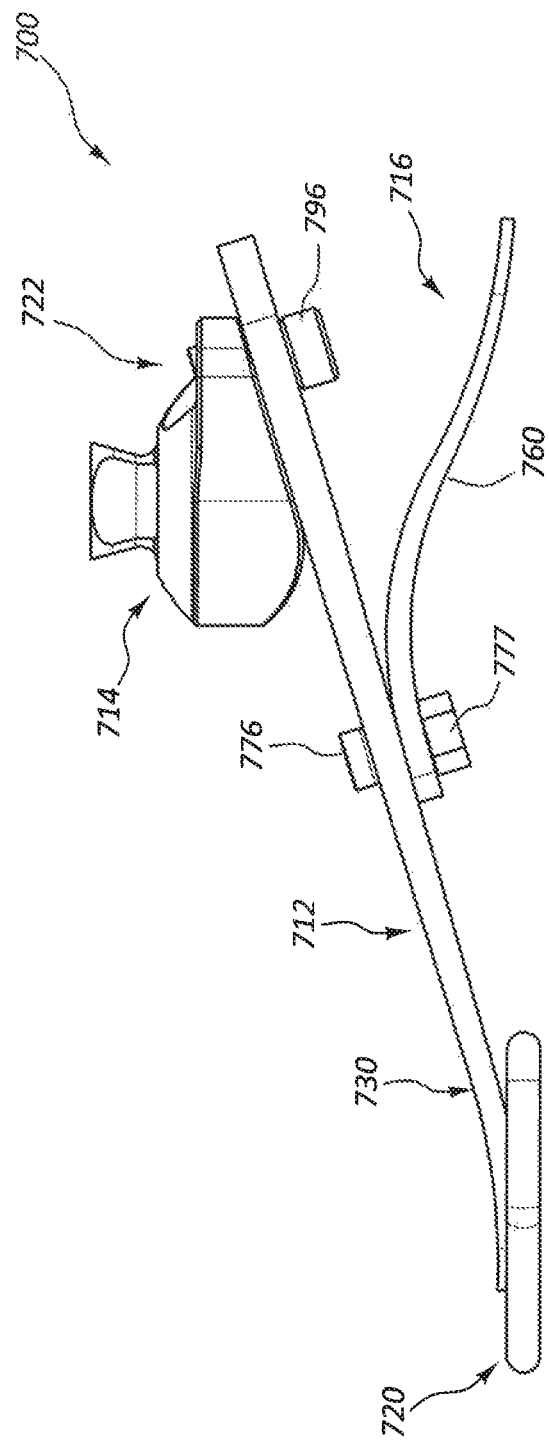
FIG. 70 is a left side view of the prosthetic foot of FIG. 66.

Referring primarily to FIG. 67, prosthetic foot 700 includes a spring assembly, 712, an attachment member 714, a heel assembly 716, a toe pad 720, and a connection assembly 722. Spring assembly 712 includes a spring element 730 having toe and heel end portions 734, 736, first and second slots 738, 740, top and bottom surfaces 744, 746, and a length $L_1$. Attachment member 714 includes a connector 750, a bottom surface 752, and apertures 754. Heel assembly 716 includes a spring member 760 having top and bottom surfaces 762, 764, a posterior edge 768, and mounting apertures 779. Toe pad 720 includes a channel 790 receptive of the toe end portion 734 of spring element 730. Connection assembly 722 includes first and second fasteners 792, 794, each having a head 798 and shank 799. First and second fasteners 792, 794 threadably engage nut 796.

The attachment member 714 may be connected to spring assembly 712 by extending fasteners 792, 794 through apertures 754 of attachment member 714, and slots 738, 740 of spring element 730, and into threaded engagement with nut 796. Heel assembly 716 may be mounted to spring assembly 712 by extending a pair of fasteners 776 through the slots 778 of spring element 730, and apertures 779 of spring member 760, and into threaded engagement with nut 777. Slots 778 may be positioned at a location that is spaced between the toe and heel end portions 734, 736 of spring element 730.

The prosthetic foot 700 may be adjustable in a longitudinal direction to alter at least one of the effective lengths $L_{E1}$, $L_{E2}$. The effective length $L_{E2}$ may be adjusted by loosening fasteners 792, 794 and sliding attachment member 714 longitudinally relative to spring element 730. The effective length $L_{E2}$ may be adjusted by loosening fastener 776 and sliding heel assembly 716 longitudinally relative to spring element 730. Many other embodiments are possible in which at least one of the attachment member 714 and heel assembly 716 is restricted from being adjusted longitudinally relative to spring assembly 712, thereby providing adjustment of at least one of the effective lengths $L_{E1}$, $L_{E2}$ (see FIG. 69). Further, the connection features used to attach attachment member 714 and heel assembly 716 to spring assembly 712 may be rearranged, modified, or replaced with other types of connection features to provide the same or similar length adjustability described with reference to FIGS. 66-70. In some embodiments, the prosthetic foot may include two or more toe spring elements (e.g., see prosthetic foot 100 in FIGS. 1-10) and integrate at least some of the attachment features and length adjustability features shown in FIGS. 66-70 related to prosthetic foot 700.

Figure 71:
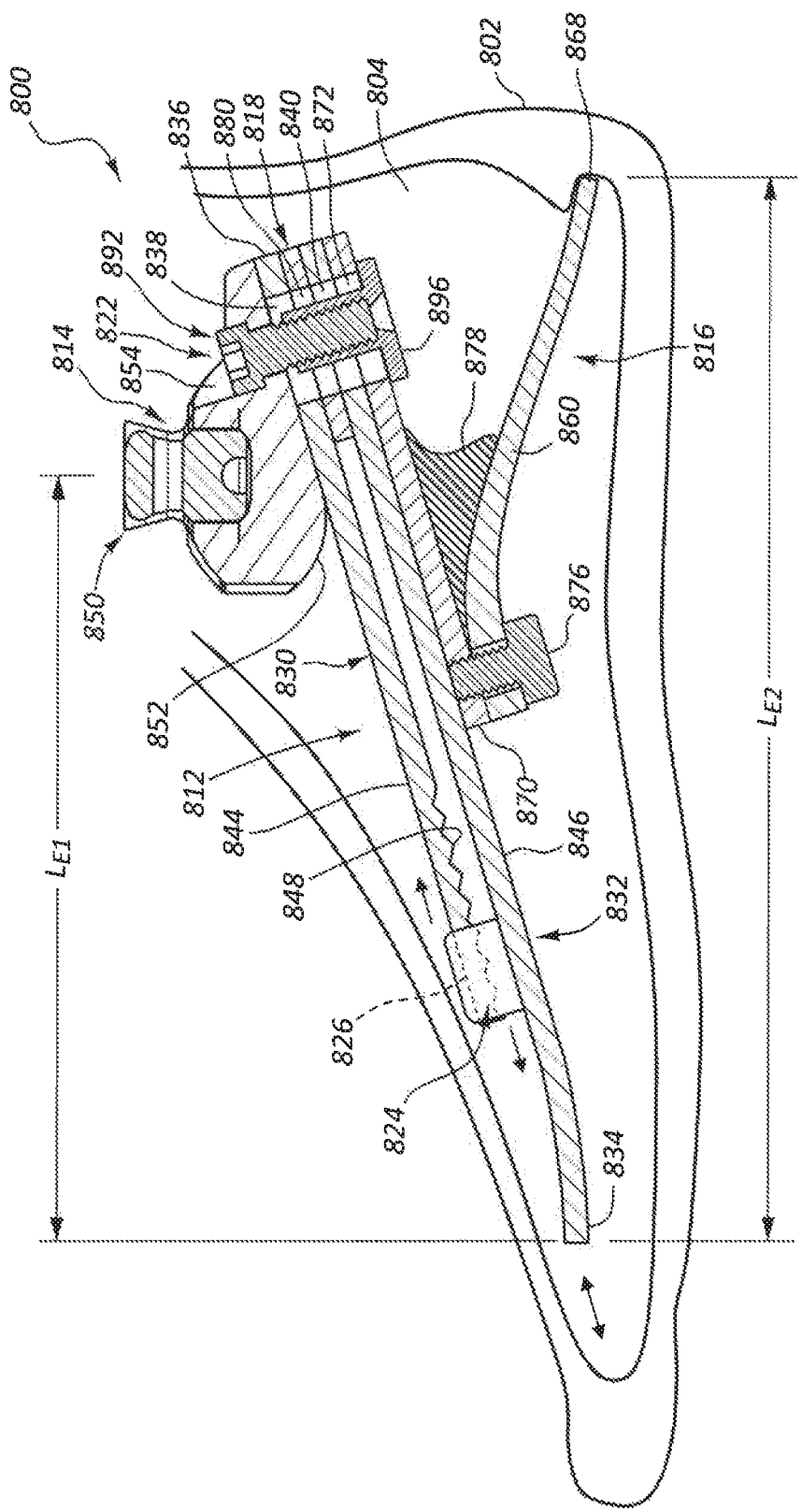
FIG. 71 is a cross-sectional view of an example prosthetic foot in accordance with the present disclosure.

Referring now to FIG. 71, another example prosthetic foot 800 is shown including a different dual toe spring embodiment. Prosthetic foot 800 includes a cover 802 having a cover interior 804, and a spring assembly 812, an attachment member 814, a heel assembly 816, a spacer 818, and a connection assembly 822 positioned within the cover interior 804. The cover 802 may comprise a flexible polymer material and may have the appearance of a nature foot.

Spring assembly 812 includes first and second spring elements 830, 832, toe and heel end portions 834, 836, at least one slot 838 formed in the first spring element 830, at least one slot 840 formed in the second spring element 832, and top and bottom surfaces 844, 846. The first and second spring elements 830, 832 may have different lengths (e.g., spring element 832 having a greater length than spring element 830).

Attachment member 814 includes a connector 850, a bottom surface 852, and at least one aperture 854. Attachment member 814 is arranged along top surface 844 for spring element 830. Apertures 854 may align with slot 838.

Heel assembly 816 includes a spring member 860 having a posterior edge 868. Heel assembly 816 may also include a mounting plate 870 with slot 872, at least one fastener 876, and a stiffening wedge 878 interposed between the spring member 860 and mounting plate 870. Fastener 876 may connect spring member 860 to mounting plate 870. Slots 872 may be aligned with slot 838 and aperture 854. Spacer 818 may include at least one slot 880. The slot 880 may be aligned with slot 838, aperture 854, and slot 872.

Connection assembly 822 includes at least one fastener 892, and at least one nut 896. Fastener 892 extends through aperture 854, slot 838, slot 880, and slot 872, and into threaded engagement with nut 896.

Prosthetic foot 800 may also include a spring spacer 824. Spring spacer 824 may be positioned at a toe end portion of spring element 830. Spring spacer 824 may include a channel 826 receptive of the toe end portion of spring element 830. Spring element 830 may include a plurality of positioning grooves 848 positioned along its length. Spring spacer 824 may be movable longitudinally along first spring element 830 and held in an adjusted longitudinal position with positioning grooves 848. Moving spring spacer 824 longitudinally relative to spring assembly 812 may adjust a stiffness of spring assembly 812. The adjustment in stiffness provided by longitudinal movement of spring spacer 824 may offset changes in stiffness of spring assembly 812 resulting from length adjustment in prosthetic foot 800 (e.g., moving at least one of attachment member 814 and heel assembly 816 longitudinally relative to spring assembly 812).

Adjusting at least one of the effective lengths $L_{E1}$, $L_{E2}$ of prosthetic foot 800 may be done by first loosening connection assembly 822, which permits longitudinal adjustment of at least one of attachment member 814 and heel assembly 816 relative to spring assembly 812. At least one of attachment member 814 and heel assembly 816 may be slid longitudinally relative to spring assembly 812, and then held in the adjusted longitudinal position by tightening connection assembly 822.

The prosthetic feet 10, 400, 800 may be referred as dual or multiple toe spring prosthetic feet. The prosthetic feet 100, 200, 300, 500, 600, 700 may be referred to as a single toe spring prosthetic feet. The heel assemblies, attachment assemblies, connection assemblies, and other features disclosed with reference to any single embodiment disclosed herein may be interchangeable with features of other prosthetic foot embodiments disclosed herein. Heel assemblies of different shapes, sizes, materials, etc., may be used in any of the prosthetic feet disclosed herein. At least some heel assemblies used may include features that permit longitudinal adjustment of the heel assembly relative to the spring assembly of the prosthetic foot.

Various features may be used to provide stiffness adjustability for a prosthetic foot in combination with the length adjustable features shown in any of the prosthetic foot embodiments of FIGS. 1-71. For example, the longitudinally adjusting spacer 18 shown in FIGS. 1-10, the spring spacer 824 shown in FIG. 71, or a similar feature, may be used to adjust stiffness of the toe spring element or other features of the spring assembly to counterbalance stiffness modifications resulting from adjusting either one of the effective lengths $L_{E1}$, $L_{E2}$ of a given prosthetic foot.

A potential advantage related to at least some of the prosthetic feet embodiments disclosed herein is the ability to shift the longitudinal position of the toe spring element(s), attachment member, and/or heel assembly relative to each other to adjust an effective length feature of the prosthetic foot. As mentioned above, various types of connection assemblies may be used. A connection assembly including two fasteners and mating nuts may provide stability in a lateral direction with limited relative rotation between the spring assembly, attachment member, heel assembly, and spacer. Other types of connection assemblies may be possible that include, for example, a single fastener, or three or more fasteners. Other types of alignment and adjustment features may be used in combination with the connection assembly to limit lateral and rotational movement of the spring assembly, attachment member, heel assembly, and spacer relative to each other while providing the desired fixing of those components when the connection assembly is tightened. For example, mating grooves, recesses, protrusions, and the like may be formed in any one of the spring assembly, attachment member, heel assembly, and spacer to limit such lateral and/or rotational movement while the connection assembly applies a compression force (e.g., in a vertical) direction when tightened.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the present systems and methods and their practical applications, to thereby enable others skilled in the art to best utilize the present systems and methods and various embodiments with various modifications as may be suited to the particular use contemplated.

Unless otherwise noted, the terms "a" or "an," as used in the specification and claims, are to be construed as meaning "at least one of." In addition, for ease of use, the words "including" and "having," as used in the specification and claims, are interchangeable with and have the same meaning as the word "comprising." In addition, the term "based on" as used in the specification and the claims is to be construed as meaning "based at least upon."

What is claimed is:

1. A foot prosthesis, comprising:
   a spring assembly, comprising:
      a top leaf spring;
      a bottom leaf spring spaced apart from and positioned vertically below the top leaf spring and arranged in parallel with the top leaf spring along an entire length of the top leaf spring;
      a heel end portion;
      a toe end portion;
      an adjustable stiffening member affixed to at least one of the top and bottom leaf springs and positioned in the toe end portion of the spring assembly, the adjustable stiffening member being movable along a length of the spring assembly to adjust a point of contact between the top and bottom leaf springs, a location of the point of contact determing a stiffness property of at least one of the top and bottom leaf springs; and
      a position fixing feature formed on one of the top and bottom leaf springs, wherein the position fixing feature comprises a plurality of positioning grooves that are configured to fix the adjustable stiffening member at a location along the length of the top and bottom leaf springs, wherein the plurality of positioning grooves are formed on a surface of one of the top and bottom leaf springs, and wherein the plurality of positioning grooves extend across the surface of one of the top and bottom leaf springs.

2. The foot prosthesis of claim 1, further comprising a heel spring member mounted to the bottom leaf spring and extending to a heel end of the foot prosthesis.

3. The foot prosthesis of claim 1, wherein at least one of the top and bottom leaf springs defines the toe end portion and extends to a toe end of the foot prosthesis.

4. The foot prosthesis of claim 1, further comprising a spacer positioned between the top leaf spring and the bottom leaf spring at at the heel end portion.

5. The foot prosthesis of claim 1, wherein a portion of the adjustable stiffening member is positioned between the top and bottom leaf springs and defines the point of contact.

6. The foot prosthesis of claim 1, further comprising:
   an attachment member mounted to the top leaf spring, the attachment member being configured to connect the foot prosthesis to a lower limb prosthesis component;
   a heel member mounted to and positioned below the bottom leaf spring, the heel member arranged to support ground reaction forces at heel strike.

7. The prosthetic foot of claim 1, wherein the top and bottom leaf springs are arranged in parallel with each other, are fixed to each other at the heel end portion, and are disconnected from each other at the toe end portion.

8. A prosthetic foot, comprising:
   a top leaf spring;
   a bottom leaf spring spaced apart from and positioned vertically below the top leaf spring and arranged in parallel with the top leaf spring along an entire length of the top leaf spring;
   a stiffness adjustment member affixed to one of the top and bottom leaf springs and adjustable along a length of the prosthetic foot to adjust a stiffness of the prosthetic foot;
   a position fixing feature formed on one of the top and bottom leaf springs, wherein the position fixing feature comprises a plurality of positioning grooves that are configured to fix the stiffness adjustment member at a location along the length of the top and bottom leaf springs, wherein the plurality of positioning grooves are formed on a surface of one of the top and bottom leaf springs, and wherein the plurality of positioning grooves extend across the surface of one of the top and bottom leaf springs; and
   a prosthetic attachment member mounted to the top leaf spring;
   wherein the top leaf spring and the bottom leaf spring are fixed to each other at a heel end of the prosthetic foot and disconnected from each other at a toe end of the prosthetic foot.

9. The prosthetic foot of claim 8, further comprising a heel member having a length that is less than a length of the top and bottom leaf springs.

10. The prosthetic foot of claim 8, further comprising a spacer positioned between the top and bottom leaf springs at a heel end of the prosthetic foot.

11. The prosthetic foot of claim 10, wherein the stiffness adjustment member includes a spacer portion arranged forward of the spacer.

12. The prosthetic foot of claim 8, wherein the top and bottom leaf springs are fixed to each other at a heel end of the prosthetic foot and are movable relative to each other at a toe end of the prosthetic foot.

13. The prosthetic foot of claim 8, wherein the stiffness adjustment member is adjustably mounted to one of the top and bottom leaf springs and movable along a length dimension of the prosthetic foot.

14. A prosthetic foot, comprising:
- a spring assembly, comprising:
  - a first leaf spring;
  - a second leaf spring spaced apart from and positioned vertically below the first leaf spring and arranged in parallel with the first leaf spring along an entire length of the first leaf spring and the second leaf spring;
  - a heel end portion;
  - a toe end portion;
  - a spacer positioned between the first leaf spring and second leaf spring at the heel end portion;
- a stiffness adjustment member positioned at the toe end portion and adjustable along a length dimension of the prosthetic foot to adjust a stiffness of the prosthetic foot;
- a position fixing feature formed on one of the first and second leaf springs, wherein the position fixing feature comprises a plurality of positioning grooves that are configured to fix the stiffness adjustment member at a location along the length of the first and second leaf springs, wherein the plurality of positioning grooves are formed on a surface of one of the first and second leaf springs, and wherein the plurality of positioning grooves extend across the surface of one of the first and second leaf springs,
- wherein the first leaf spring and the second leaf spring are fixed to each other at the heel end portion and disconnected from each other at the toe end portion;
- a prosthetic attachment member positioned vertically above the first leaf spring; and
- a heel member positioned vertically below the second leaf spring.

15. The prosthetic foot of claim 14, wherein the stiffness adjustment member includes a spacer portion positioned between the first leaf spring and the second leaf spring at a location spaced forward of the spacer.

16. The prosthetic foot of claim 15, wherein the spacer portion is affixed to the first leaf spring and is supported on and slidable relative to a top surface of the second leaf spring.

17. The prosthetic foot of claim 16, wherein the space portion is positioned forward of a midpoint between the toe and heel end portions.

18. A method of adjusting a stiffness of a foot prosthesis, the method comprising:
- providing at least first and second leaf springs spaced apart and arranged in parallel with each other along an entire length of the first leaf spring and the second leaf spring, a stiffness adjustment device, a prosthetic attachment member, and a heel member, wherein a positioning fixing feature comprising a plurality of positioning grooves formed on one of the first and second leaf springs, wherein the plurality of positioning grooves are formed on a surface of one of the first and second leaf springs, and wherein the plurality of positioning grooves extend across the surface of one of the first and second leaf springs;
- mounting the prosthetic attachment member to the first leaf spring, the prosthetic attachment member being configured to connect the foot prosthesis to a lower limb prosthesis;
- mounting the heel member to the second leaf spring, the heel member arranged to contact a ground surface at a heel area of the foot prosthesis;
- affixing the stiffness adjustment device to at least one of the first and seond leaf springs; and
- adjusting a position of the stiffness adjustment device relative to at least one of the first and second leaf springs to adjust a stiffness of the foot prosthesis, wherein the positioning fixing feature holds the stiffness adjustment device in an adjusted position along a length of the foot prosthesis.

\* \* \* \* \*